US012544270B2

(12) United States Patent
Deibel

(10) Patent No.: US 12,544,270 B2
(45) Date of Patent: Feb. 10, 2026

(54) VENTILATION TUBES

(71) Applicant: Preceptis Medical, Inc., Golden Valley, MN (US)

(72) Inventor: Rudolf Andreas Deibel, Eden Prairie, MN (US)

(73) Assignee: Preceptis Medical, Inc., Golden Valley, MN (US)

( * ) Notice: Subject to any disclaimer, the term of this patent is extended or adjusted under 35 U.S.C. 154(b) by 301 days.

(21) Appl. No.: 18/299,154

(22) Filed: Apr. 12, 2023

(65) Prior Publication Data

US 2023/0329914 A1 Oct. 19, 2023

Related U.S. Application Data

(60) Provisional application No. 63/330,915, filed on Apr. 14, 2022.

(51) Int. Cl.
*A61F 11/20* (2022.01)

(52) U.S. Cl.
CPC .................................. *A61F 11/202* (2022.01)

(58) Field of Classification Search
CPC ..................................................... A61F 11/202
See application file for complete search history.

(56) References Cited

U.S. PATENT DOCUMENTS 3,530,860 A 9/1970 Majoros
3,662,754 A 5/1972 Halloran
3,807,409 A 4/1974 Paparella et al.
3,871,380 A 3/1975 Heros
3,888,258 A 6/1975 Akiyama
3,897,786 A 8/1975 Garnett et al.
3,913,584 A 10/1975 Walcle
3,948,271 A 4/1976 Akiyama
4,174,716 A 11/1979 Treace
(Continued)

FOREIGN PATENT DOCUMENTS

CN 102014795 A 4/2011
GB 2437708 A 11/2007
(Continued)

OTHER PUBLICATIONS

Australian Examination Report dated Jul. 18, 2013 for Australian patent application No. 2009215468, 4 pages.
(Continued)

*Primary Examiner* — Richard G Louis
(74) *Attorney, Agent, or Firm* — Leanne Taveggia Farrell; Westman, Champlin & Koehler, P.A.

(57) ABSTRACT

A ventilation tube comprising a hollow body oriented along a central axis and having an inner facing wall, an outer facing wall, a medial end and a lateral end. The hollow body including a length that extends from the medial end to the lateral end. A lateral tab includes a base end coupled to the outer facing wall of the hollow body and extends outwardly from the outer facing wall to a free end. The lateral tab is located between and spaced apart from the medial end and the lateral end. The base end includes a first length that extends lengthwise along the hollow body and the free end includes a second length. The first length of the base end of the lateral tab is greater than the second length of the free end of the lateral tab.

20 Claims, 29 Drawing Sheets

(56) References Cited

U.S. PATENT DOCUMENTS

| | | | |
|---|---|---|---|
| 4,334,538 | A | 6/1982 | Juhn |
| 4,445,517 | A | 5/1984 | Field |
| 4,468,218 | A | 8/1984 | Armstrong |
| 4,473,073 | A | 9/1984 | Darnell |
| 4,580,568 | A | 4/1986 | Gianturco |
| 4,695,275 | A | 9/1987 | Bruce et al. |
| 4,744,792 | A | 5/1988 | Sander et al. |
| 4,964,850 | A | 10/1990 | Bouton et al. |
| 5,026,378 | A | 6/1991 | Goldsmith, III |
| 5,053,040 | A | 10/1991 | Goldsmith, III |
| 5,073,166 | A | 12/1991 | Parks et al. |
| 5,139,502 | A | 8/1992 | Berg et al. |
| 5,178,623 | A | 1/1993 | Cinberg et al. |
| 5,207,685 | A | 5/1993 | Cinberg et al. |
| 5,254,120 | A | 10/1993 | Cinberg et al. |
| 5,466,239 | A | 11/1995 | Cinberg et al. |
| 5,484,434 | A | 1/1996 | Cartmell et al. |
| 5,496,329 | A | 3/1996 | Reisinger |
| 5,566,094 | A | 10/1996 | Kojima et al. |
| 5,578,053 | A | 11/1996 | Yoon |
| 5,601,568 | A | 2/1997 | Chevillon et al. |
| 5,643,280 | A | 7/1997 | Del Rio et al. |
| 5,645,584 | A | 7/1997 | Suyama |
| 5,665,094 | A | 9/1997 | Goldenberg |
| 5,693,065 | A | 12/1997 | Rains, III |
| D389,915 | S | 1/1998 | Emerson et al. |
| 5,709,677 | A | 1/1998 | Slatkine |
| 5,711,309 | A | 1/1998 | Goldenberg |
| 5,916,150 | A | 6/1999 | Sillman |
| 5,976,151 | A | 11/1999 | Siegbahn |
| 6,027,532 | A | 2/2000 | Hobeika |
| 6,156,064 | A | 12/2000 | Chouinard |
| D439,337 | S | 3/2001 | Jones |
| 6,238,402 | B1 | 5/2001 | Sullivan, III et al. |
| 6,245,077 | B1 | 6/2001 | East et al. |
| 6,258,067 | B1 | 7/2001 | Hill |
| 6,292,702 | B1 | 9/2001 | King et al. |
| D453,833 | S | 2/2002 | Hess |
| 6,361,526 | B1 | 3/2002 | Reisdorf et al. |
| 6,390,975 | B1 | 5/2002 | Walls et al. |
| 6,406,453 | B1 | 6/2002 | Goode et al. |
| 6,443,970 | B1 | 9/2002 | Schulze et al. |
| 6,450,937 | B1 | 9/2002 | Mercereau et al. |
| 6,527,780 | B1 | 3/2003 | Wallace et al. |
| 6,692,455 | B2 | 2/2004 | Goode et al. |
| 6,695,861 | B1 | 2/2004 | Rosenberg et al. |
| D490,152 | S | 5/2004 | Myall et al. |
| 6,730,056 | B1 | 5/2004 | Ghaem et al. |
| 6,770,080 | B2 | 8/2004 | Kaplan et al. |
| 6,776,797 | B1 | 8/2004 | Blom et al. |
| 6,936,023 | B2 | 8/2005 | Goode et al. |
| 6,939,494 | B2 | 9/2005 | Goode et al. |
| D521,641 | S | 5/2006 | Reschke et al. |
| D538,936 | S | 3/2007 | Böhmel et al. |
| 7,235,099 | B1 | 6/2007 | Duncavage et al. |
| 7,410,480 | B2 | 8/2008 | Muni et al. |
| 7,419,497 | B2 | 9/2008 | Muni et al. |
| 7,704,259 | B2 | 4/2010 | Kaplan et al. |
| D619,579 | S | 7/2010 | Vieira |
| 7,879,033 | B2 | 2/2011 | Sartor et al. |
| 8,052,693 | B2 | 11/2011 | Shahoian |
| D664,657 | S | 7/2012 | Vieira et al. |
| D673,676 | S | 1/2013 | Goudreau et al. |
| 8,864,774 | B2 | 10/2014 | Liu et al. |
| 8,979,868 | B2 | 3/2015 | Loushin et al. |
| 9,011,363 | B2 | 4/2015 | Clopp et al. |
| 9,023,059 | B2 | 5/2015 | Loushin et al. |
| 9,370,448 | B2 | 6/2016 | Loushin et al. |
| 9,782,298 | B2 | 10/2017 | Loushin et al. |
| 9,907,700 | B2 | 3/2018 | Clopp et al. |
| 10,624,792 | B2 | 4/2020 | Loushin et al. |
| 10,695,224 | B2 | 6/2020 | Loushin et al. |
| 10,792,189 | B2 | 10/2020 | Leland et al. |
| 2002/0058899 | A1 | 5/2002 | Goode et al. |
| 2003/0018291 | A1 | 1/2003 | Hill et al. |
| 2005/0004520 | A1 | 1/2005 | Lemoine et al. |
| 2005/0049675 | A1 | 3/2005 | Wallace |
| 2005/0256450 | A1 | 11/2005 | Palasis et al. |
| 2006/0025793 | A1 | 2/2006 | Gibson et al. |
| 2006/0116607 | A1 | 6/2006 | Nakamura et al. |
| 2008/0051804 | A1 | 2/2008 | Cottler et al. |
| 2008/0097295 | A1 | 4/2008 | Makower et al. |
| 2008/0234708 | A1 | 9/2008 | Houser et al. |
| 2008/0262468 | A1 | 10/2008 | Clifford et al. |
| 2008/0262505 | A1 | 10/2008 | Shahoian |
| 2008/0262508 | A1 | 10/2008 | Clifford et al. |
| 2008/0262509 | A1 | 10/2008 | Clifford et al. |
| 2008/0262510 | A1 | 10/2008 | Clifford |
| 2009/0275955 | A1 | 11/2009 | Kutluhan |
| 2009/0299141 | A1 | 12/2009 | Downey et al. |
| 2009/0299379 | A1 | 12/2009 | Katz et al. |
| 2010/0174290 | A1 | 7/2010 | Wuebbeling et al. |
| 2010/0256653 | A1 | 10/2010 | Kaplan et al. |
| 2011/0015645 | A1 | 1/2011 | Liu et al. |
| 2011/0282190 | A1 | 11/2011 | Caffey et al. |
| 2011/0288559 | A1 | 11/2011 | Shahoian |
| 2012/0179187 | A1 | 7/2012 | Loushin et al. |
| 2013/0338678 | A1* | 12/2013 | Loushin ................ A61F 11/202 606/109 |
| 2020/0237559 | A1 | 7/2020 | Loushin |
| 2020/0281772 | A1 | 9/2020 | Loushin |

FOREIGN PATENT DOCUMENTS

| | | | |
|---|---|---|---|
| WO | 2003057082 | A1 | 7/2003 |
| WO | 2008131195 | A2 | 10/2008 |
| WO | 2009105619 | A2 | 8/2009 |
| WO | 2012094666 | A1 | 7/2012 |
| WO | 2014075949 | A1 | 5/2014 |
| WO | 2016025310 | A1 | 2/2016 |

OTHER PUBLICATIONS

Canadian Office Action dated Feb. 3, 2015 for Canadian patent application No. 2,716,040, 5 pages.

Canadian Office Action dated Apr. 5, 2019 for Canadian application No. 2,876,865, 4 pages.

Canadian Office Action dated Nov. 12, 2019 for Canadian application No. 2,876,865, 5 pages.

Canadian Office Action dated Apr. 16, 2020 for corresponding Canadian application Serial No. 2,876,865, 5 pages.

Chinese Office Action dated Jul. 7, 2016 for Chinese application No. 201380031471.2, with English translation, 13 pages.

Chinese Office Action dated Dec. 4, 2012 from Chinese patent application No. 200980113954.0, with English translation, 7 pages.

Chinese Office Action dated Jul. 22, 2013 for Chinese patent application No. 200980113954.0, with English translation, 9 pages.

Chinese Office Action dated Jan. 28, 2014 for Chinese patent application No. 200980113954.0, with English translation, 16 pages.

Chinese Office Action dated Jul. 11, 2014 for Chinese patent application No. 200980113954.0, with English translation, 9 pages.

Chinese First Office Action dated Nov. 18, 2015 for Chinese Patent Application No. 20130031471.2, 14 pages.

European Extended Search Report dated Aug. 25, 2011 for European patent application No. 09713274.0, 7 pages.

European Commuication dated Sep. 13, 2011 for European patent application No. 09713274.0, 1 page.

European Communication dated Apr. 18, 2017 for European patent application No. 09713274.0, 5 pages.

European Office Action dated Feb. 24, 2016 for European patent application No. 09713274.0, 4 pages.

European Office Action dated May 25, 2018 for Europeaan patent application No. 13733138.5, 4 pages.

European Communication dated Apr. 29, 2015 for European Patent Application Serial No. 13733138.5, 2 pages.

European Summons to attend oral proceedings pursuant to Rule 115(1) EPC dated Jul. 1, 2021, 6 pages.

European Communication dated Aug. 23, 2022 for corresponding European application Serial No. 13733138.5, 4 pages.

Indian First Examination Report dated Jun. 26, 2020 for corre-

(56) References Cited

OTHER PUBLICATIONS sponding Indian application Serial No. 67/MUMNP/2015.
Indian Office Action dated Feb. 22, 2018 for Indian application No. 5199/CHENP/2010, with English translation, 6 pages.
Korean Office Action dated Jun. 20, 2019 for Korean application No. 10-2015-7000954, with English translation, 5 pages.
PCT Search Report and Written Opinion dated Oct. 1, 2009 from International application No. PCT/US2009/034648, 9 pages.
PCT Search Report and Written Opinion dated Sep. 18, 2013 from International application No. PCT/US2013/045082, 13 pages.
PCT Search Report and Written Opinion dated Apr. 25, 2012 from International application No. PCT/US2012/020629, 13 pages.
PCT Notification of Transmittal of the International Search Report and the Written Opinion of the International Searching Authority, or the Declaration and Search Report dated Sep. 18, 2023 for corresponding PCT application Serial No. PCT/US2023/018487, 7 pages.
PCT Written Opinion dated Sep. 18, 2023 for corresponding PCT application Serial No. PCT/US2023/018487, 7 pages.

* cited by examiner

VENTILATION TUBES

CROSS-REFERENCE TO RELATED APPLICATION

The present application is based on and claims the benefit of U.S. provisional patent application Ser. No. 63/330,915, filed Apr. 14, 2022, the content of which is hereby incorporated by reference in its entirety.

SUMMARY

A ventilation tube includes a hollow body oriented along a central axis and has an inner facing wall, an outer facing wall, a medial end and a lateral end. The hollow body includes a length that extends from the medial end to the lateral end. The ventilation tube also includes a lateral tab having a base end coupled to the outer facing wall of the hollow body and extending outwardly from the outer facing wall to a free end. The lateral tab is located between and spaced apart from the medial end and the lateral end and includes a lower portion having the base end and an upper portion having the free end. The upper portion of the lateral tab includes a first width that is greater than a second width of the lower portion of the lateral tab.

A ventilation tube includes a hollow body oriented along a central axis and has an inner facing wall, an outer facing wall, a medial end and a lateral end. The hollow body includes a length that extends from the medial end to the lateral end. The ventilation tube also includes a lateral tab having a base end coupled to the outer facing wall of the hollow body and extending outwardly from the outer facing wall to a free end. The lateral tab is located between and spaced apart from the medial end and the lateral end. The base end includes a first length that extends lengthwise along the hollow body and the free end includes a second length. The first length of the base end of the lateral tab is greater than the second length of the free end of the lateral tab.

A ventilation tube includes a hollow body oriented along a central axis and has an inner facing wall, an outer facing wall, a medial end and a lateral end. The hollow body includes a length that extends from the medial end to the lateral end. At least one medial flange is located at the medial end of the hollow body. The ventilation tube also includes a lateral tab having a base end coupled to the outer facing wall of the hollow body and extending outwardly from the outer facing wall to a free end and one or more lateral flanges located at the lateral end of the hollow body. In an undeployed state, the at least one medial flange and the plurality of lateral flanges are folded in towards the hollow body while the lateral tab protrudes outwardly from the outer facing surface of the hollow body. In a deployed state, the at least one medial flange and the one or more lateral flanges unfold so that at least portions of the medial flange and the plurality of lateral flanges extend outwardly from the outer facing surface of the hollow body and the lateral tab remains unchanged between the undeployed state and the deployed state.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Ventilation tubes, such as pressure equalization (PE) ear tubes or tympanostomy tubes, are tiny, hollow devices inserted into tissue or membranes of a human body to enable drainage and provide air flow. For example, an ear tube inserted into a tympanic membrane (eardrum) provides drainage of the middle ear, allows air to flow into the middle ear and prevents the buildup of fluids behind the eardrum. In one particular embodiment, a ventilation tube includes a material that allows the tube to remain in a deformed state during insertion into a body. After insertion through a target membrane, the tube is allowed to re-form and anchor in place. The deformed ear tube and the insertion device that places the ventilation tube in the membrane allows for minimally invasive ventilation tube placement, which reduces the pain, cost and risks associated with conventional procedures and devices.

Figure 1:
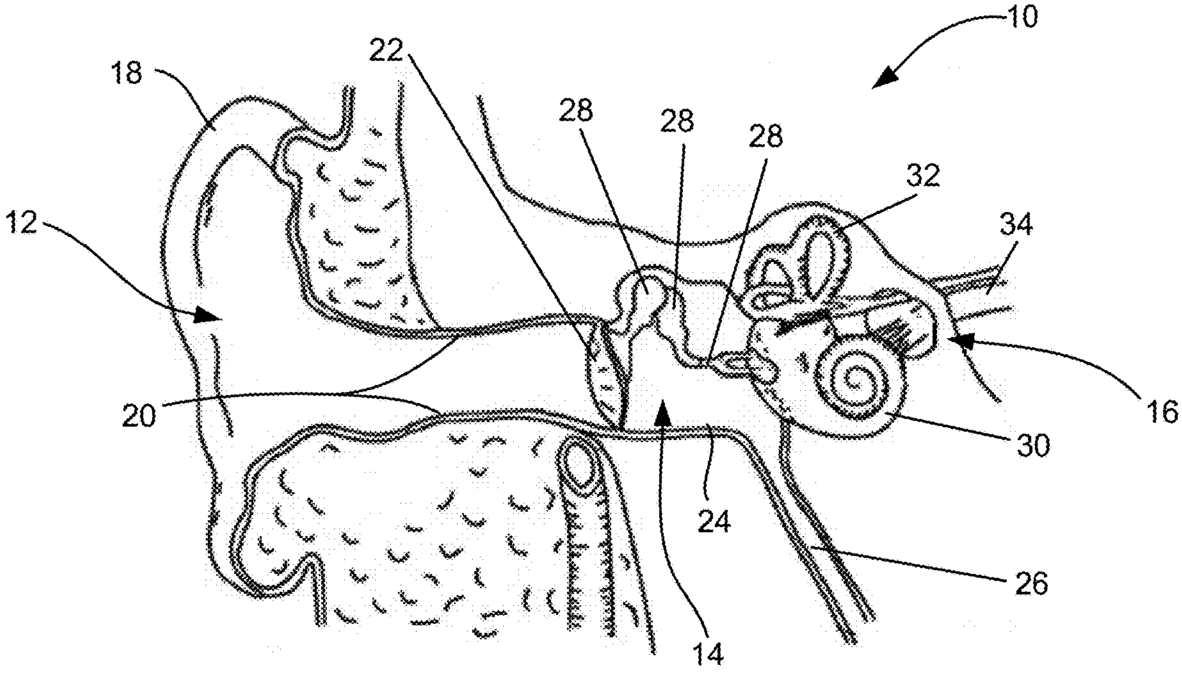
FIG. 1 is a simplified diagram of an ear.

FIG. 1 illustrates a system of organs in an ear 10 of a body that enables a person to detect sound. Ear 10 is able to change sound pressure waves into a signal of nerve impulses to be processed by the brain. Ear 10 includes an outer ear 12, a middle ear 14 and an inner ear 16. Outer ear 12 collects sound and includes the pinna 18, the ear canal 20 and an outer most layer of the ear drum or tympanic membrane (TM) 22. Pinna 18 helps direct sound through ear canal 20 to TM 22. Middle ear 14 includes an air-filled cavity 24 having an opening for the Eustachian tube 26 that is located behind TM 22. Middle ear 14 also includes ossicles 28. Inner ear 16 includes the fluid-filled cochlea 30 and the semicircular canals 32. Cochlea 30 is the auditory portion of the inner ear, while semicircular canals 32 are attuned to both gravity and motion. The ossicles bones 28 transmit sound from the tympanic membrane 22 to cochlea 30. Fluid in cochlea 30 moves in response to the vibrations coming from middle ear 14. The motion of the fluid is converted to electrical impulses, which travel along the auditory nerve 34 to structures in the brainstem for further processing. Eustachian tube 26 couples cavity 24 of middle ear 14 to the nose and mouth of a human. In a normal state, Eustachian tube 26 is collapsed. However, Eustachian tube 26 can open and close to equalize pressure in cavity 24.

An infection of the middle ear 14 can result in a buildup of fluid and increased pressure in cavity 24 causing severe pain. Children are often prone to infections of middle ear 14 because of their underdeveloped Eustachian tube 26. A myringotomy is a surgical procedure in which a tiny incision is created in TM 22 to relieve pressure caused by the excessive buildup of fluid due to an infection of the middle ear 14. If a patient requires a myringotomy, this generally suggests that Eustachian tube 26 is either partially or completely obstructed and is not able to perform its proper functions.

In some cases, besides making an incision in TM 22, a ventilation tube is inserted into the opening. Insertion of a ventilation tube or pressure equalizing (PE) ear tube can allow external ventilation of or drainage of middle ear 14 for an extended period of time. However, in the confined space of ear canal 20, especially an ear canal of a child, insertion of a ventilation tube may be difficult. In one example, the incision made in TM 22 is often made larger than the cross-section area of the ventilation tube. In such an example, the device will fall out much earlier than desired. In another example, the tube may be over inserted or placed too far inside middle ear 14 or not far enough. During manual insertion, it is important for clinicians to have visual and haptic feedback so as to confirm that the tube is properly inserted into the membrane. Ventilation tubes that alleviate these disadvantages can greatly enhance patient comfort as well as reduce procedural time and undue injury to TM 22, while simultaneously simplifying the procedure for physicians.

Figure 2:
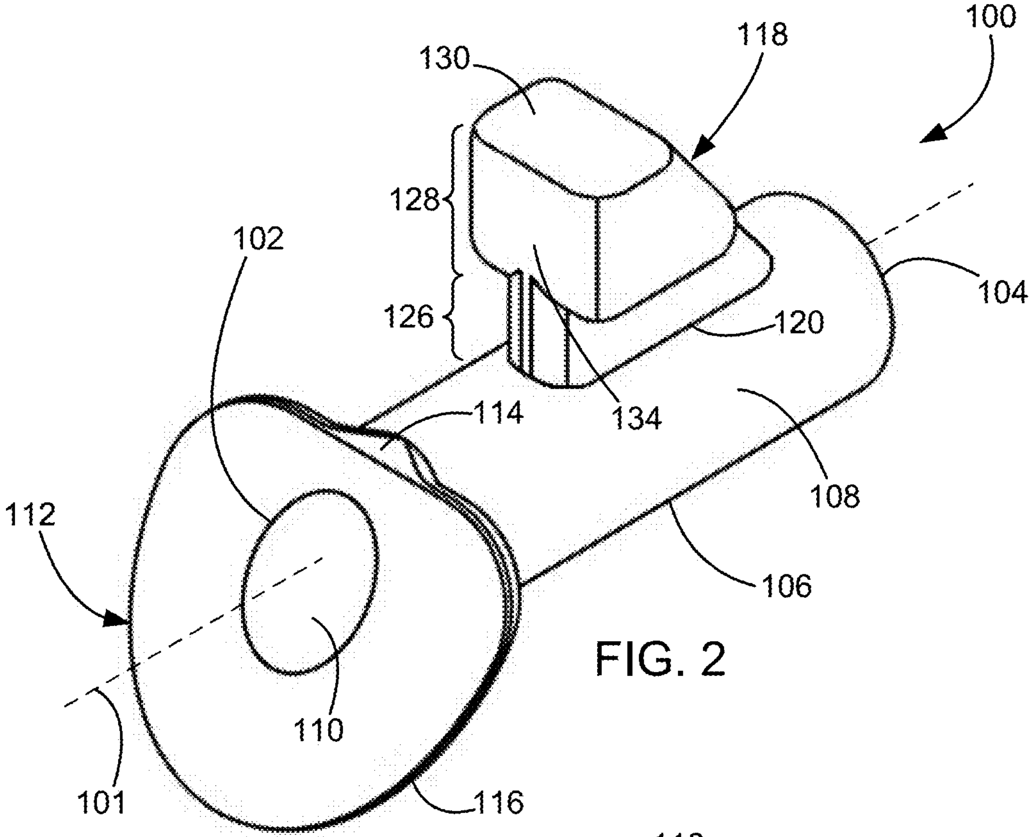
FIG. 2 illustrates a perspective view of a ventilation tube according to an embodiment.
Figure 3:
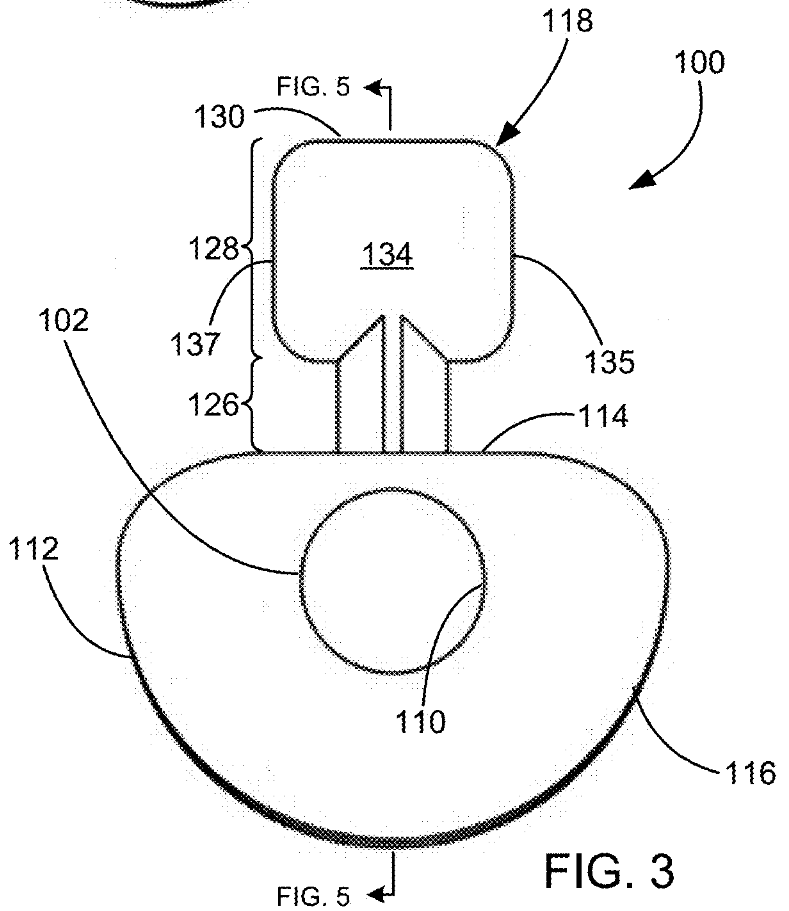
FIG. 3 illustrates a medial end view of FIG. 2.
Figure 4:
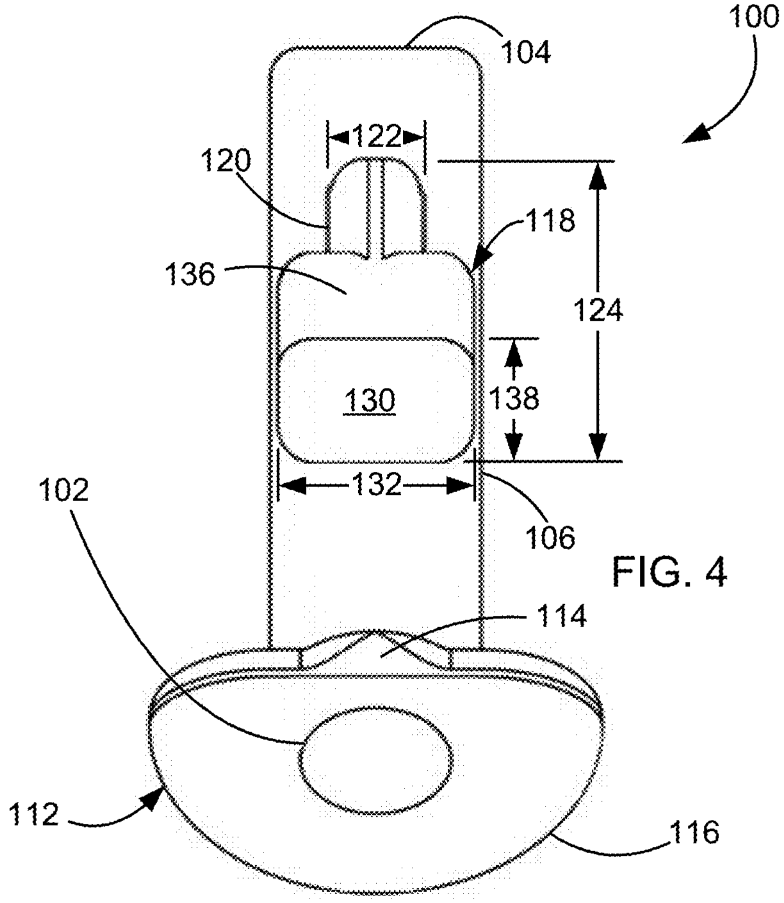
FIG. 4 illustrates a top view of FIG. 2.
Figure 5:
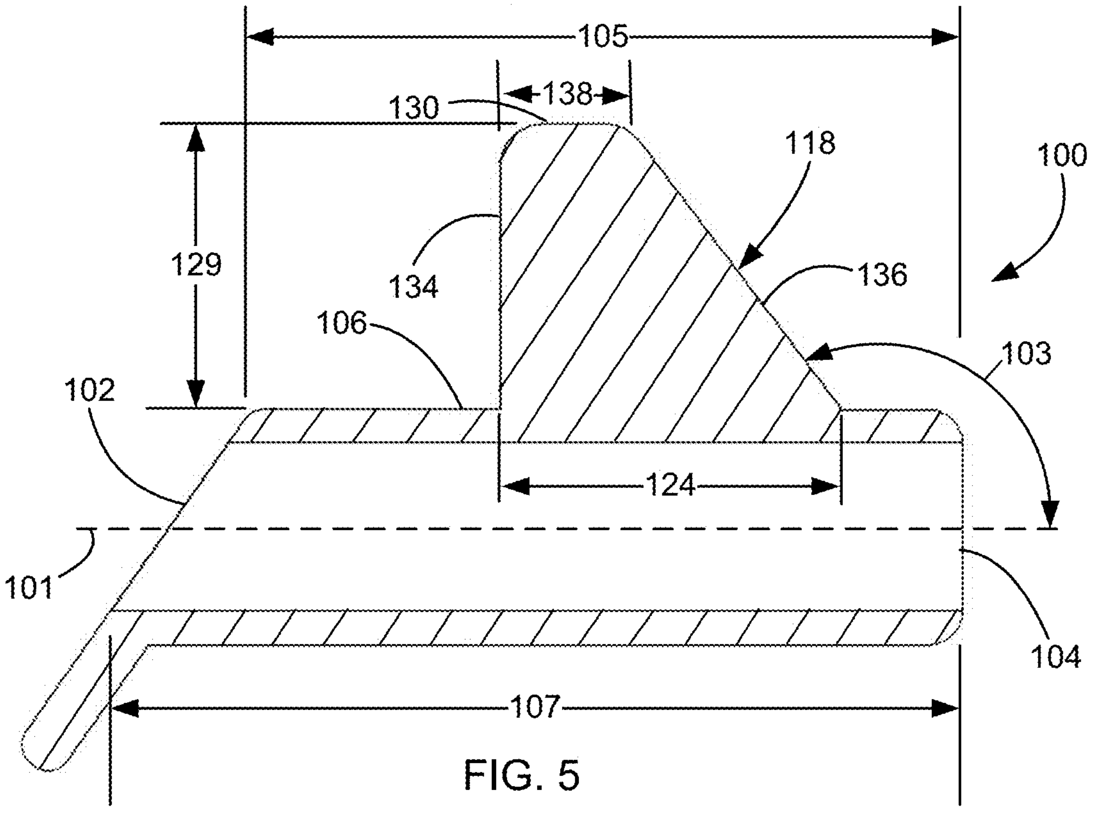
FIG. 5 illustrates a section view of FIG. 2 taken through the section line in FIG. 3.

FIG. 2 illustrates a perspective view of a ventilation tube 100 according to an embodiment. FIG. 3 illustrates a medial end view, FIG. 4 illustrates a top view and FIG. 5 illustrates a section view of ventilation tube 100 taken through the section line in FIG. 3. Ventilation tube 100 includes a medial end 102, a lateral end 104 and a hollow body 106 oriented along a central axis 101 that extends from medial end 102 to lateral end 104. Medial end 102 is configured to be positioned on a medial side of a membrane of the body or internal to the membrane, while lateral end 104 is configured to be positioned on a lateral side of the membrane or external to the membrane. Hollow body 106 is a cylindrical hollow body that includes an outer facing surface 108 and an inner facing surface 110. Medial end 102 of hollow body 106 includes a beveled end, while lateral end 104 of hollow body 106 includes a "squared" end. The beveled medial end 102 means that hollow body 106 varies in length from one longitudinal side to an opposing longitudinal side. As illustrated, a length 105 (FIG. 5) of a first longitudinal side is less than and a length 107 (FIG. 5) of an opposing second longitudinal side. It is possible that lateral end 104 may be not "squared" as long as lateral end 104 provides a complementary mating interface with a distal end of a positioning rod to support a consistent axial force on the tube while the cutting sheath is retracted to prevent the tube from deforming axially during deployment from inside a sheath. For example, if lateral end 104 is "squared," then a distal end of a positioning rod should also be "squared" so as to support a consistent axial force on the tube 100. See FIGS. 6A-6C.

In one embodiment, radially extending from medial end 102 is a medial flange 112 that follows the beveled angle of medial end 102. Medial flange 112 extends outwardly from both inner facing surface 110 of hollow body and from outer facing surface 108 of hollow body 106 about a portion of medial end 102. In another embodiment, medial end 102 of tube 100 may simply include the beveled angle of medial end 102, but may not include medial flange 112. Medial flange 112 extends between inner facing surface 110 of hollow body 106 and outer facing surface 108 of hollow body 106 about a remaining portion of medial end 102. In other words, a portion of medial flange 112 is in alignment with outer facing surface 108 of hollow body 106 while the remaining portion of medial flange 112 extends outwardly from outer facing surface 108. This gives medial flange 112 the appearance of having a flat edge 114 with the remaining of medial flange 112 having a curved edge 116. As illustrated, the flat edge 114 of medial flange 112 corresponds with the longitudinal side of hollow body 106 having length 105.

Protruding from outer facing surface 108 of hollow body 106 is a lateral tab 118. Lateral tab 118 extends from a base end 120 that is coupled to outer facing surface 108 and terminates at a free end 130. Base end 120 has a width 122 (FIG. 4) and extends lengthwise along outer facing surface 108 of hollow body 106 for a length 124 (FIG. 4). Base end 120 is located between and spaced apart from medial end 102 (and medial flange 112) and lateral end 104. Lateral tab 118 includes a lower portion 126 and an upper portion 128. Together lower and upper portions 126 and 128 encompass a height 129 (FIG. 5) of flange or tab 118, height 129 being the distance between base end 120 and free end 130. Lower portion 126 includes width 122 and upper portion 128 includes a width 132. Width 122 of lower portion is less than width 132 of upper portion 128 and width 132 of upper portion 128 is less than a width of hollow body 106. Still further, lateral tab 118 includes a medial-facing side 134, a lateral-facing side 136, a right side 135 and a left side 137. Lateral tab 118 forms a solid body defined by base end 120, free end 130, medial facing side 134, lateral-facing side 136, right side 135 and left side 137. Medial-facing side 134 may be substantially perpendicular to central axis 101 of hollow body 106, while lateral-facing side 136 may be angled from free end 130 to outer facing surface 108 of hollow body 106. In particular, free end 130 has a planar surface and includes a length 138 (FIG. 4) that may be less than length 124 of base end 120. Lateral-facing side 136 connects free end 130 to base end 120 and may be oriented at an angle 103 from central axis 101 that is greater than 90 degrees and less than 180 degrees. In one embodiment, angle 103 may be about 127 degrees.

Figure 6A:
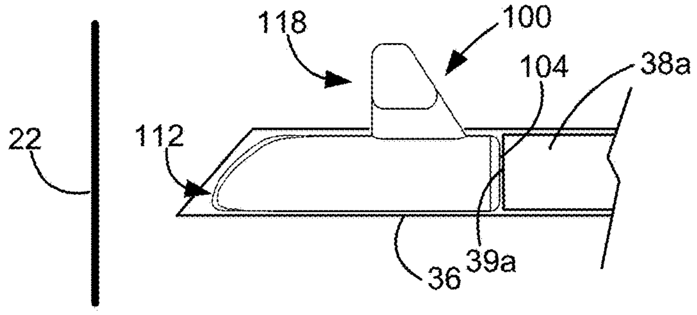
FIGS. 6A-6E illustrate the ventilation tube illustrated in FIGS. 2-5 being deployed in a membrane of a human body.

FIGS. 6A-6E illustrate ventilation tube 100 of FIGS. 2-5 being deployed in a membrane of a human body, such as tympanic membrane 22. While tympanic membrane 22 is illustrated as being perpendicular to central axis 22, it should be realized that this is for illustrative purposes only and that the tympanic membranes in humans are generally oriented at angles in the human ear canal. In FIG. 6A, ventilation tube 100 is positioned in a cutting sheath 36 in an undeployed state. In the undeployed state, medial flange 112 is folded or deformed inwardly towards outer facing surface 108 of hollow body 106 to reside inside cutting sheath 36 and lateral tab 118 protrudes through a slot in cutting sheath 36. Curved edge 116 of medial flange 112 includes a radius of curvature that is optimized to fold into cutting sheath 36 into the undeployed state to prevent medial flange 112 from sticking out of the slot in cutting sheath 36 or sticking to itself. For example, the two opposing corners between curved edge 116 and flat edge 114 may have a radii of curvatures be between 0.4 and 1.5 mm, more specifically between 0.6 and 1 mm. In other words, the two opposing corners between curved edge 116 and flat edge 114 have radii of curvatures that may be ⅙ to ⅓ of the width of medial flange 116. This radii keeps the two tips of the medial flange from pushing against one another and sticking together in the undeployed state. It is important to properly size the corners between flat edge 114 and curved edge 116 so that the corners do not wrap around each other and stick to each other and thereby cause the medial flange to not deploy correctly. The width of the slot in cutting sheath 36 is large enough to accommodate width 122 of lower portion 126 of lateral tab 118, while upper portion 128 of lateral tab 118 has a width 132 that is greater than the width of the slot in cutting sheath 36 and greater than width 122 of lower portion 126. However, width 132 of upper portion 128 may be less than a width of hollow body 106. A positioning rod 38*a* is also located inside cutting sheath 36. A distal end 39*a* of positioning rod 38*a* is positioned adjacent to lateral end 104 of ventilation tube 100.

Figure 6B:
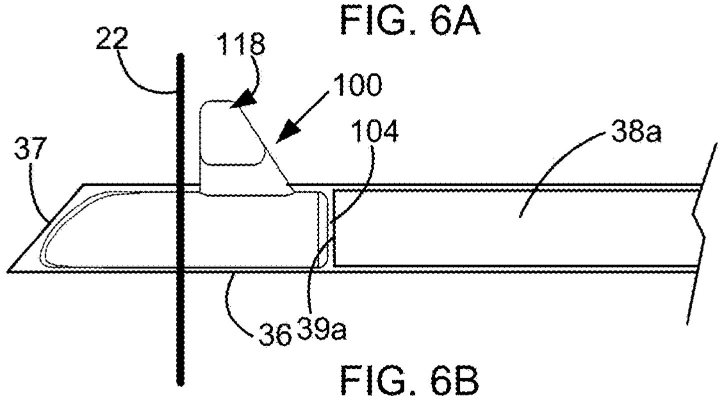

In FIG. 6B, a cutting edge 37 of cutting sheath 36 is advanced through membrane 22 by a clinician to make an incision. Distal end 39*a* of positioning rod 38*a* is held against lateral end 104 of tube 100 to keep tube 100 in an undeployed state inside of cutting sheath 36. While incising membrane 22, a clinician receives both visual and haptic feedback to ensure ventilation tube 100 is not being overly inserted or under inserted. In particular, a clinician may use lateral tab 118 as a visual indicator. As long as the clinician can visualize lateral tab 118, then tube 100 has not been overly inserted. As described above, upper portion 128 of lateral tab 118 is wider than lower portion 126 of lateral tab 118. A wider upper portion 128 improves the visibility of lateral tab 118 compared to a lateral tab that has a width that is similar to width 122 of lower portion 126. A clinician may also use lateral tab 118 as a haptic feedback indicator. Lateral tab 118 includes a geometry that has a high longitudinal stiffness or stiffness in a direction that is parallel with axis 101 of tube 100. In particular, the longer the length 124 of base end 120 of lateral tab 118 extends along hollow body 106 of tube 100 the greater the longitudinal stiffness. While the solid body that results from base end 120 having length 124 that is greater than length 138 of free end 130 loses very little stiffness because length 124 remains high, having length 138 of free end 130 be less than length 124 of base end 120 reduces the overall size and mass of tube 100, which provides additional benefits including minimizing the impact tube 100 has on how the eardrum behaves, provide less mechanical stress at the insertion site so that tube 100 does not fall out too soon and minimize irritation in the ear. This high mechanical resistance in the form of stiffness is felt by the clinician upon medial-facing side 134 contacting membrane 22 as illustrated in FIG. 6B. Such haptic feedback prevents over insertion and under insertion of tube 100.

Figure 6C:
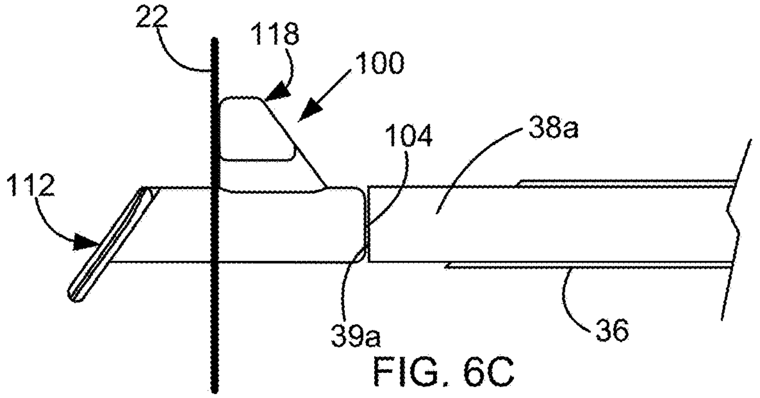
Figure 6D:
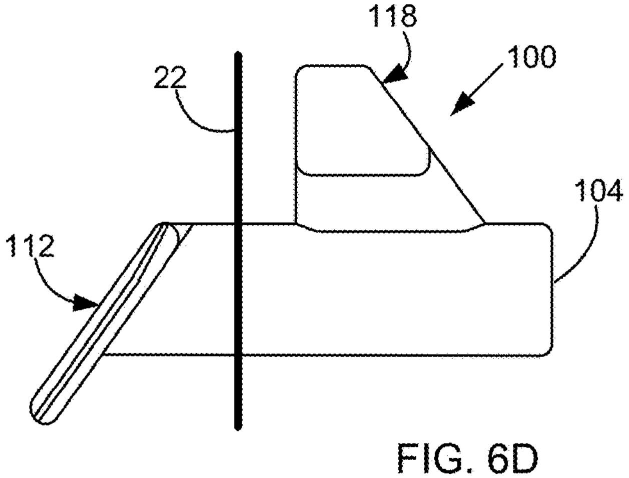
Figure 6E:
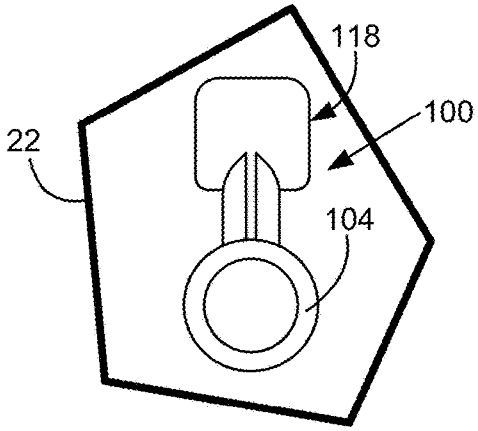

In FIG. 6C, cutting sheath 36 is retracted from around ventilation tube 100 to deploy tube 100 into a deployed state, while positioning rod 38*a* holds lateral end 104 of tube 100 in place. In a deployed state, as is illustrated in FIGS. 6D and 6E, medial flange 112 is unfolded and lateral tab 118 is located lateral to membrane 22. Both medial flange 112 and lateral tab 118 are configured to hold tube 100 in membrane 22. FIG. 6D illustrates ventilation tube 100 deployed in tympanic membrane 22, while FIG. 6E illustrates a lateral end view of ventilation tube 100 deployed in tympanic membrane 22.

Figure 7:
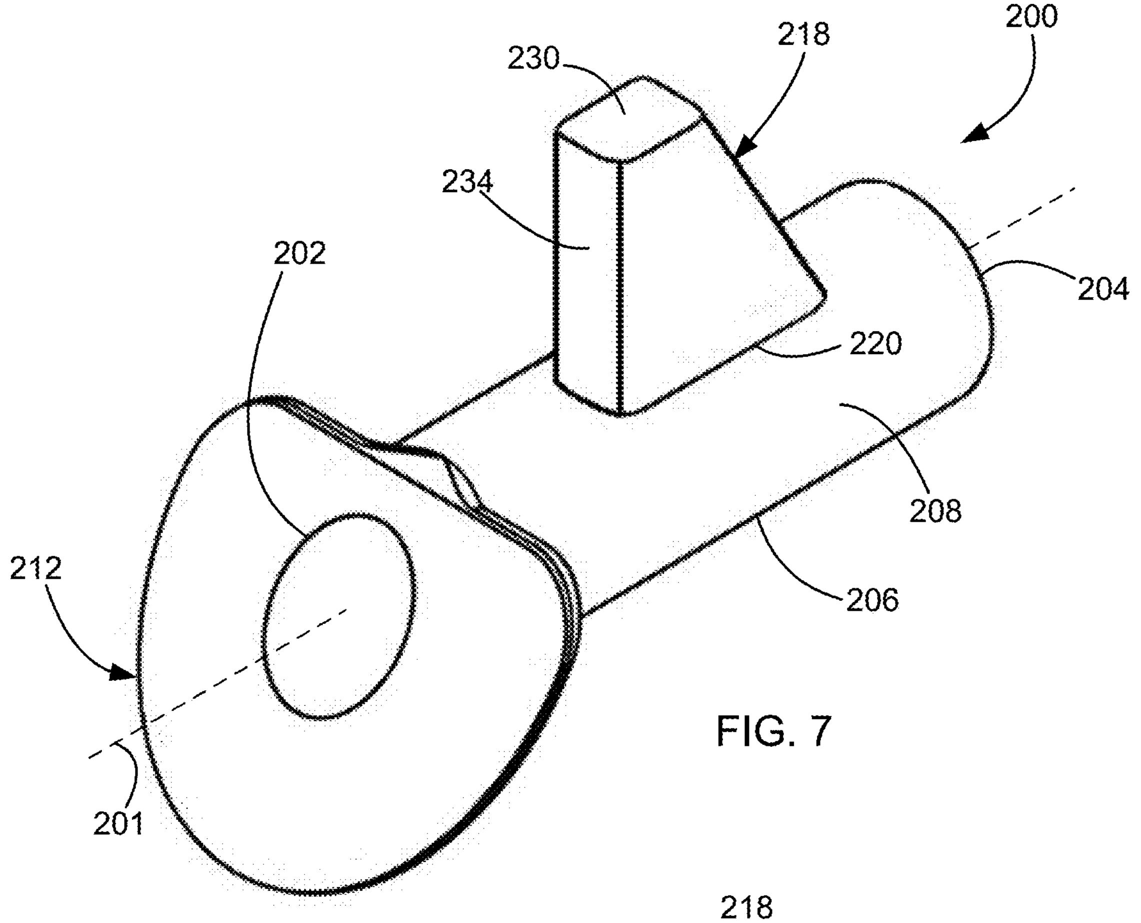
FIG. 7 illustrates a perspective view of a ventilation tube according to another embodiment.
Figure 8:
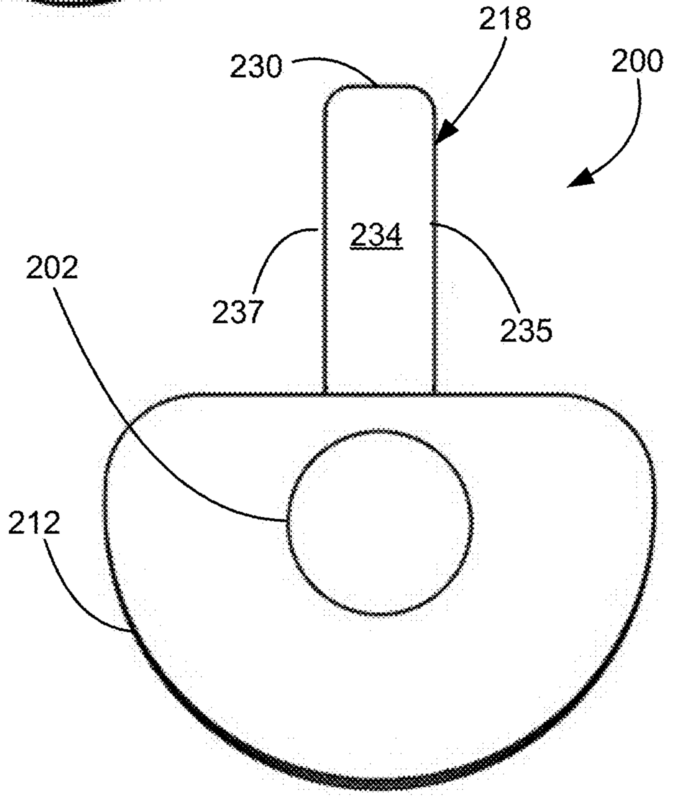
FIG. 8 illustrates a medial end view of FIG. 7.
Figure 9:
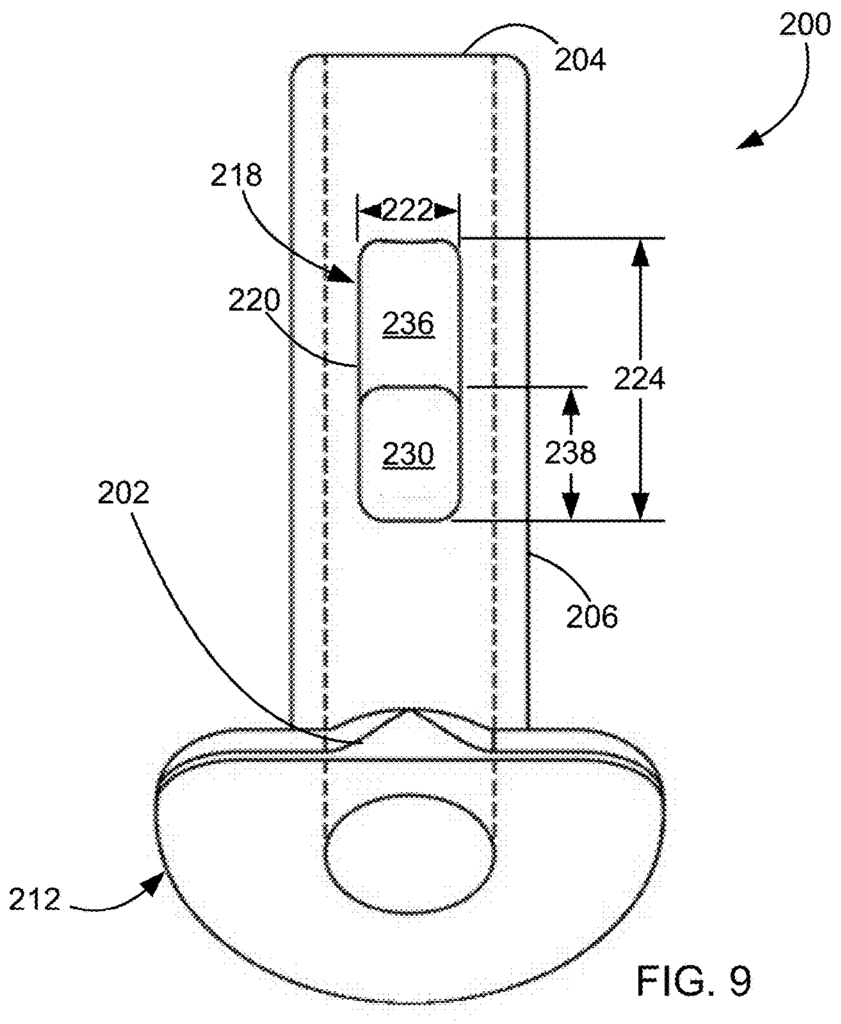
FIG. 9 illustrates a top view of FIG. 7.
Figure 10:
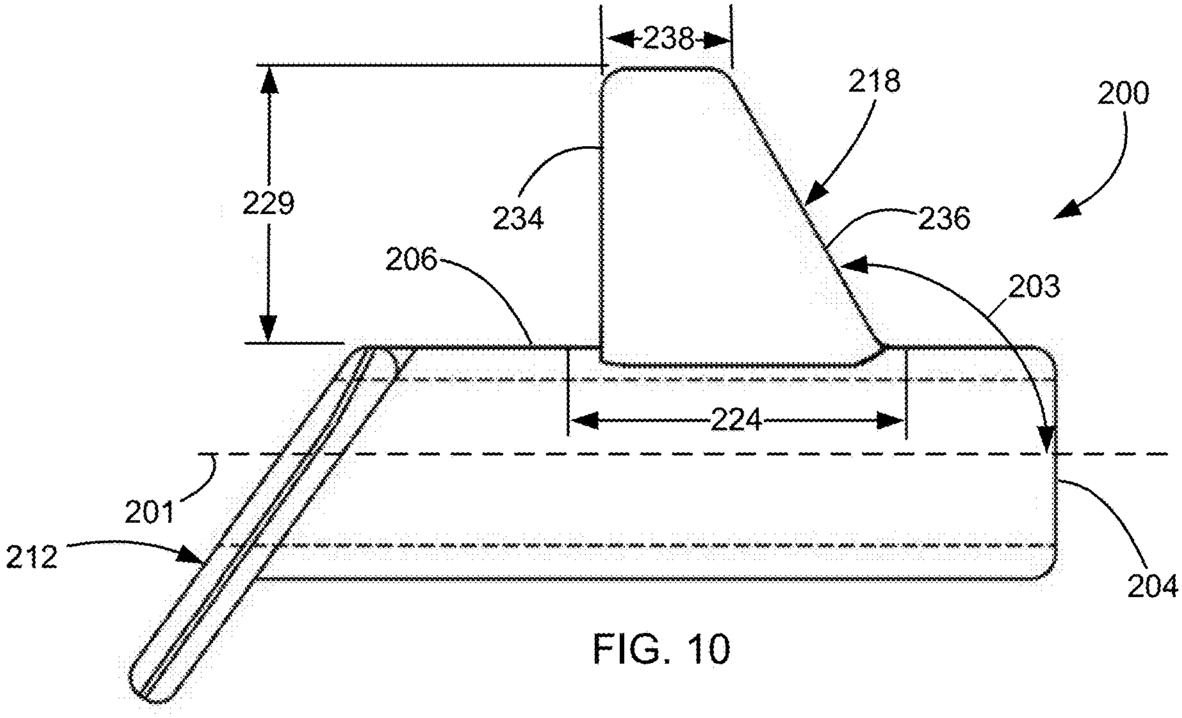
FIG. 10 illustrates a right side view of FIG. 7.

FIG. 7 illustrates a perspective view of a ventilation tube 200 according to an embodiment. FIG. 8 illustrates a medial end view, FIG. 9 illustrates a top view, and FIG. 10 illustrates a side view of ventilation tube 200. Ventilation tube 200 is similar to ventilation tube 100 including a similar hollow body 206 oriented along a central axis 201 and medial flange 212, however, the geometry of lateral tab 218 is somewhat different. Lateral tab 218 protrudes and extends from a base end 220 that is coupled to outer facing surface 208 and terminates at a free end 230. The entirety of lateral tab 218 has a width 222 (FIG. 9). Base end 220 includes a length 224 (FIG. 9) that extends lengthwise along outer facing surface 208 of hollow body 206. Base end 220 is located between and spaced apart from medial end 202 (and medial flange 212) and lateral end 204.

Lateral tab 218 includes a height 229 (FIG. 10), which is the distance between base end 220 and free end 230. Still further, lateral tab 218 includes a medial-facing side 234, a lateral-facing side 236, a right side 235 and a left side 237. Lateral tab 218 forms a solid body defined by base end 220, free end 230, medial facing side 234, lateral-facing side 236, right side 235 and left side 237. Medial-facing side 234 may be substantially perpendicular to outer facing surface 208 of hollow body 206, while lateral-facing side 236 angles from free end 230 to outer facing surface 208 of hollow body 206. In particular, free end 230 has a planar surface and includes a length 238 (FIG. 10) that may be less than length 224 of base end 220. Lateral-facing side 236 connects free end 230 to base end 220 and may be oriented at an angle 203 from central axis 201 that is greater than 90 degrees and less than 180 degrees. In one embodiment, angle 203 may be about 119 degrees.

Ventilation tube 200 is deployed in a membrane in the same way that ventilation tube 100 is deployed in a membrane. In particular, a clinician uses lateral tab 218 as a visual indicator. As long as the clinician can visualize lateral tab 218, then tube 200 has not been overly inserted. A clinician may also use lateral tab 218 as a haptic feedback indicator. Lateral tab 218 includes a geometry that has longitudinal stiffness. In particular, length 224 and lateral-facing side 236 provide flange or tab 218 with longitudinal stiffness. This mechanical resistance in the form of stiffness is felt by the clinician upon medial-facing side 234 contacting membrane 22. Such haptic feedback prevents over insertion and under insertion of tube 200.

Figure 11:
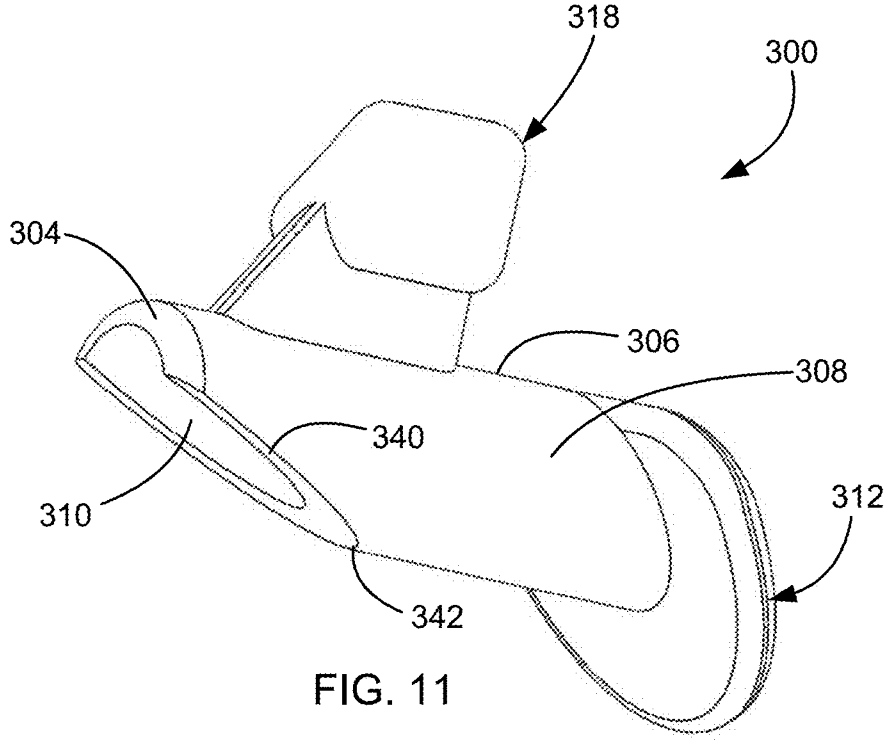
FIG. 11 illustrates a perspective view of a ventilation tube according to another embodiment.
Figure 12:
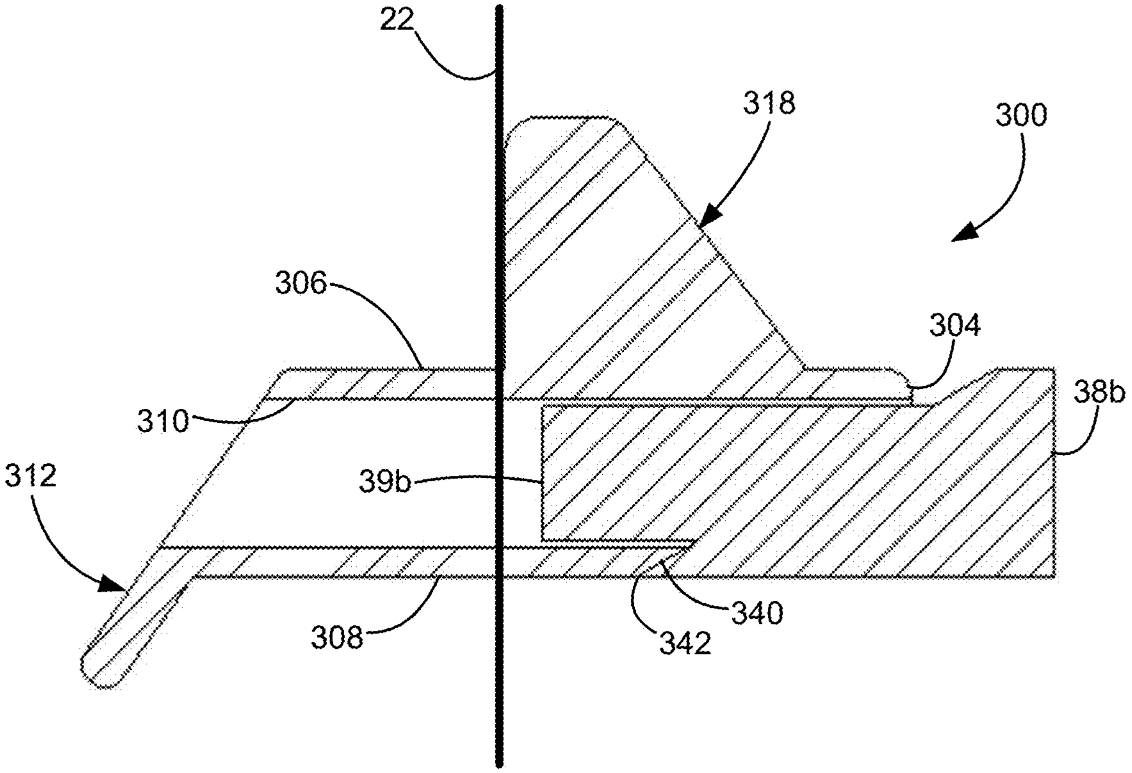
FIG. 12 illustrates a section view of the ventilation tube illustrated in FIG. 11 being inserted into a membrane of a human body with a positioning rod also illustrated in section that is configured to be used during tube deployment according to an embodiment.

FIG. 11 illustrates a perspective view of a ventilation tube 300 according to another embodiment. FIG. 12 illustrates a section view of ventilation tube 300 being inserted into a membrane 22 with a positioning rod also illustrated in section that is configured to be used in deployment according to an embodiment. Ventilation tube 300 is similar to ventilation tube 100 including having a similar lateral flange or tab 318 and medial flange 312, however, the geometry of lateral end 304 and hollow body 306 is different. Hollow body 306 includes a geometry that reduces the overall effective lumen length. Reducing the overall effective lumen length of hollow body 306 of tube 300 makes it easier to visualize through the lumen and clear plugging if it occurs in the lumen. In particular, lateral end 304 of ventilation tube 300 includes a bevel 340. Bevel 340 is a sloping surface that originates at lateral end 304 and terminates at a terminating end 342 that intersects with outer facing surface 308 of hollow body 306.

Under one embodiment, a positioning rod **38*b* with a different geometry than the geometry of positioning rod 38*a* is provided to insert ventilation tube 300. Rather than distal end 39*b* of positioning rod 38*b* having a blunt end surface area as is the case in FIGS. 6A-6C, positioning rod 38*b* and distal end 39*b* provide greater control when holding ventilation tube 300 in place during insertion and prevents tube 300 from twisting or collapsing during insertion. As illustrated in FIG. 12, a portion of distal end 39*b* is located inside the lumen of hollow body 306. In other words, a portion of distal end 39*b* is surrounded by inner facing surface 310 of hollow body 306. A remaining portion of distal end 39*b* includes a bevel end so as to mate with or contact bevel 340 including terminating end 342 that intersects with outer facing surface 308 of hollow body 306. In another embodiment, distal end 39*b* may include a bevel without a support portion that is surrounded by inner facing surface 310 of hollow body 306**.

Figure 13:
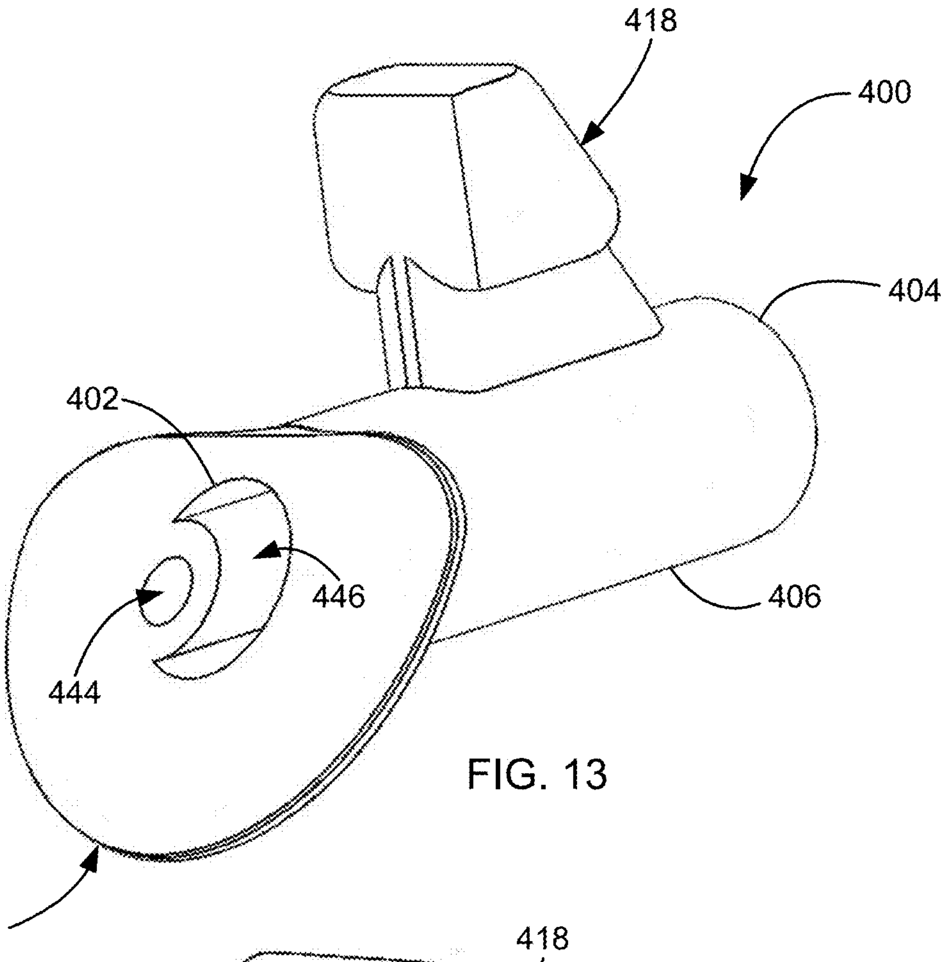
FIG. 13 illustrates a first perspective view of a ventilation tube according to another embodiment.
Figure 14:
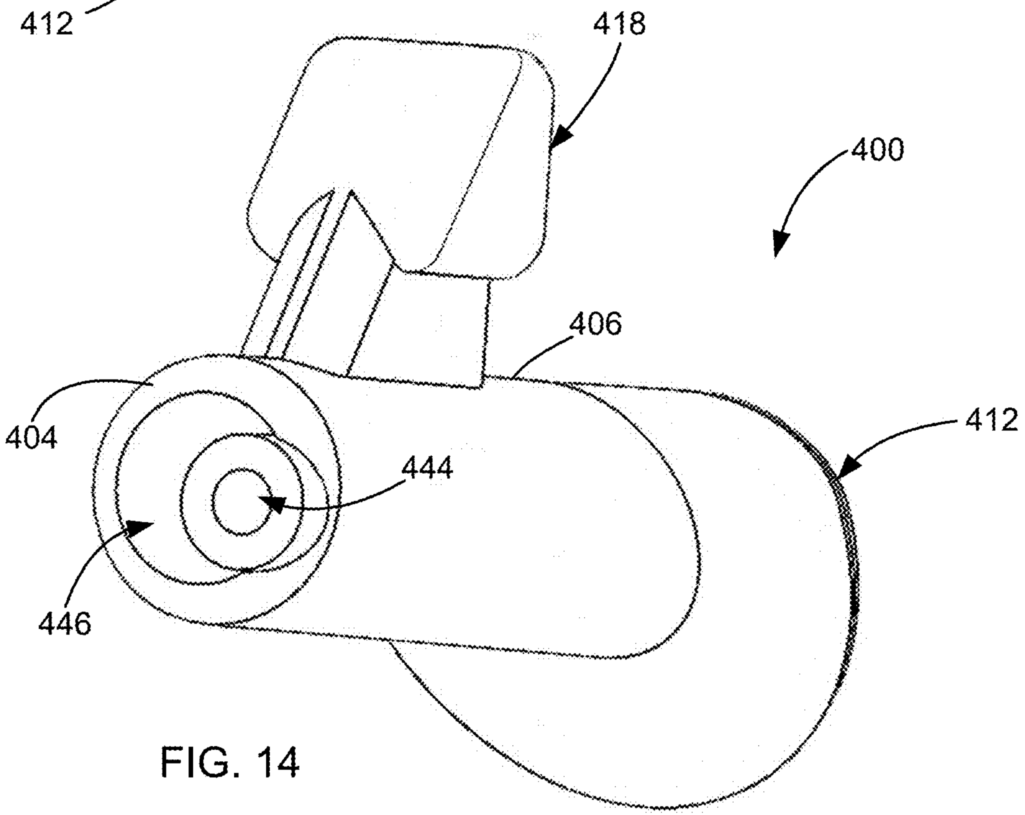
FIG. 14 illustrates a second perspective view of the ventilation tube in FIG. 13.

FIG. 13 illustrates a first perspective view of a ventilation tube 400 according to another embodiment. FIG. 14 illustrates a second perspective view of ventilation tube 400. Ventilation tube 400 is similar to ventilation tube 100 including having a similar lateral tab 418 and medial flange 412, however, the lumen of hollow body 406 is different. Hollow body 406 of tube 400 includes two or more passages along the lumen. In FIGS. 13 and 14, tube 400 includes a first lumen 444 and a second lumen 446. First lumen 444 and second lumen 446 extend from medial end 402 to lateral end 404 with second lumen 446 having a larger opening through hollow body 406 than first lumen 444. First lumen 444 is configured to house a wick, while second lumen 446 is configured to remain open to maintain an air passage. The wick is included to deliver liquid to the middle ear including therapeutics.

Figure 15:
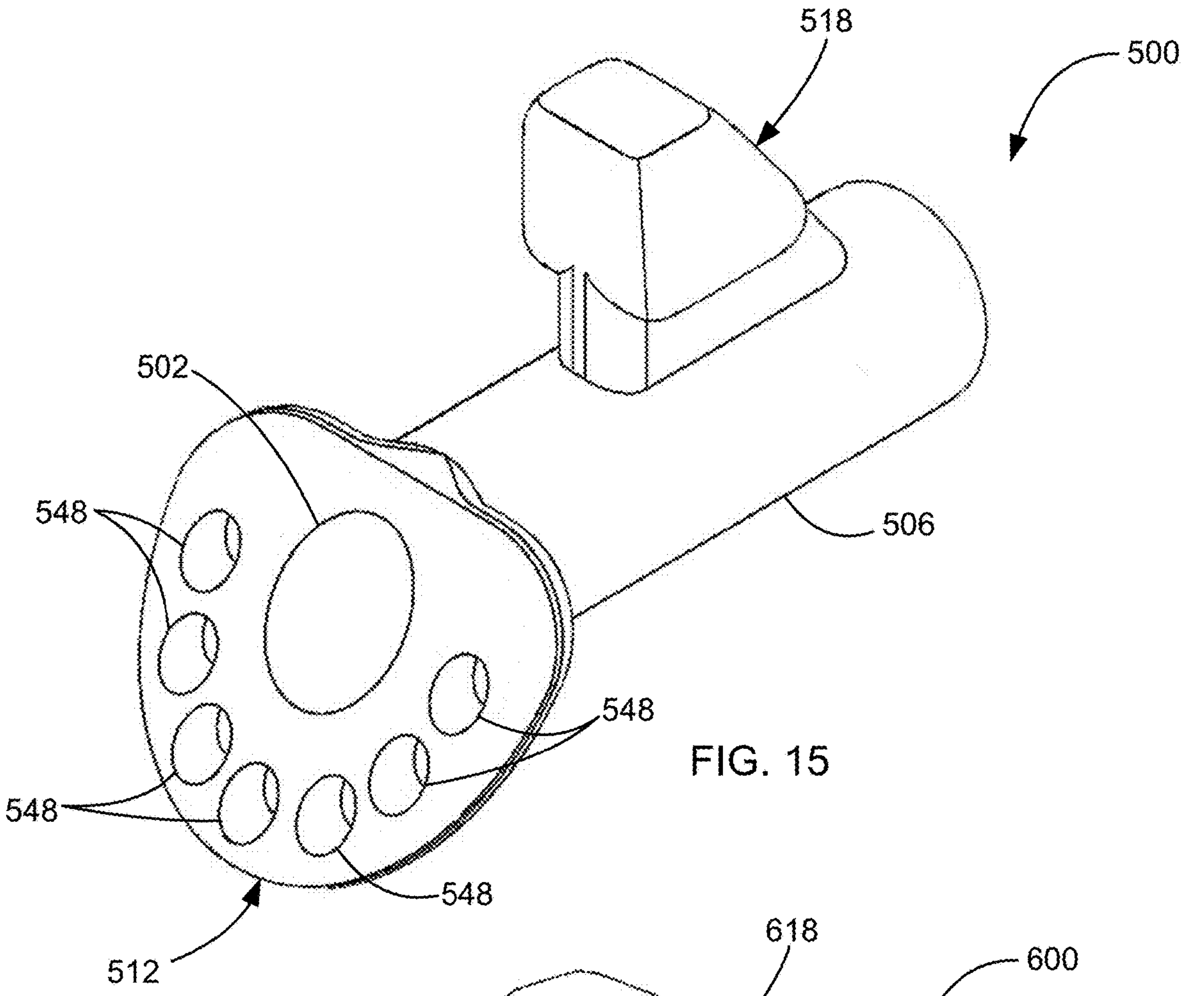
FIG. 15 illustrates a perspective view of a ventilation tube according to another embodiment.

FIG. 15 illustrates a perspective view of a ventilation tube 500 according to another embodiment. Ventilation tube 500 is similar to ventilation tube 100 including having a similar lateral tab 518 and hollow body 506, however, medial flange 512 is different. Medial flange 512 includes a plurality of spaced apart apertures 548. Apertures 548 are located between medial end 502 of hollow body 506 and curved edge 516. Apertures 548 provide medial flange 512 with more flexibility and capability of collapsing into a small space. This may allow cutting sheath 36 to be made with a smaller diameter than that which is illustrated in FIGS. 6A-6C. While material removed from medial flange 512 is in the form of circular apertures 548, the material removed from medial flange 512 may be of any shape or size and do not need to be equally sized, as long as mass of medial flange 512 and therefore tube 500 is removed.

Figure 16:
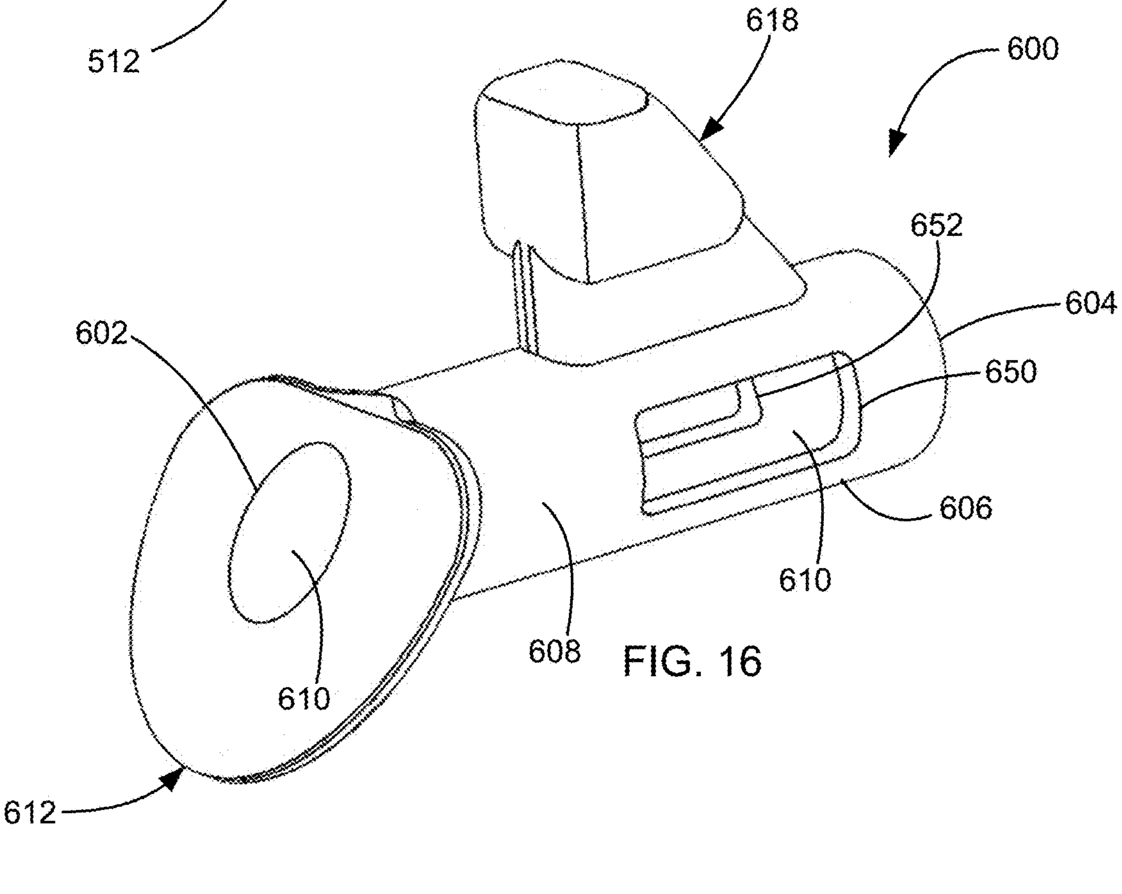
FIG. 16 illustrates a perspective view of a ventilation tube according to another embodiment.

FIG. 16 illustrates a perspective view of a ventilation tube 600 according to another embodiment. Ventilation tube 600 is similar to ventilation tube 100 including having a similar lateral tab 618 and medial flange 612, however, hollow body 606 is different. Hollow body 606 includes a pair of opposing openings 650 and 652 that extend between outer facing surface 608 and inner facing surface 610. Openings 650 and 652 are spaced apart from medial end 602 and lateral end 604, but are located closer to lateral end 604 than medial end 602. Like bevel 340 of ventilation tube 300, openings 650 and 652 reduce the overall effective lumen length. Reducing the overall effective lumen length of hollow body 606 makes it easier to visualize along the lumen and clear plugging if it occurs in the lumen.

Figure 17:
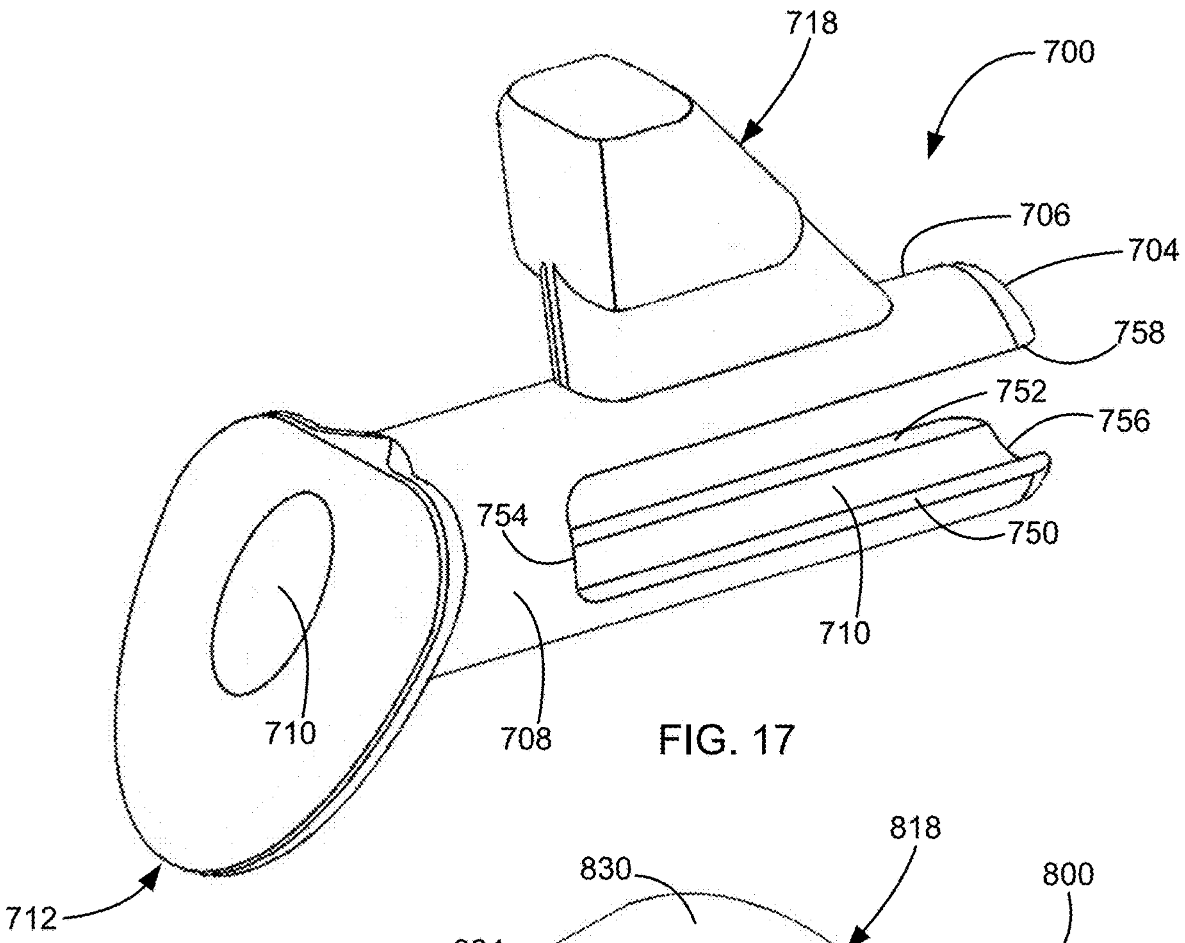
FIG. 17 illustrates a perspective view of a ventilation tube according to another embodiment.

FIG. 17 illustrates a perspective view of a ventilation tube 700 according to another embodiment. Ventilation tube 700 is similar to ventilation tube 600 including having a similar lateral tab 718 and medial flange 712, however, hollow body 706 is somewhat different. Hollow body 706 includes a pair of opposing slots 750 and 752 that extend between outer facing surface 708 and inner facing surface 710 and extend from medial ends 754 (medial end of slot 752 not shown) and terminating ends 756 and 758. Terminating ends 756 and 758 are located at lateral end 704. In other words, slots 750 and 752 are in communication with lateral end 704. Like bevel 340 of ventilation tube 300 and openings 650 and 652 of ventilation tube 600, slots 750 and 752 reduce the overall effective lumen length. Reducing the overall effective lumen length of hollow body 706 makes it easier to visualize and clear plugging in the lumen.

Figure 18:
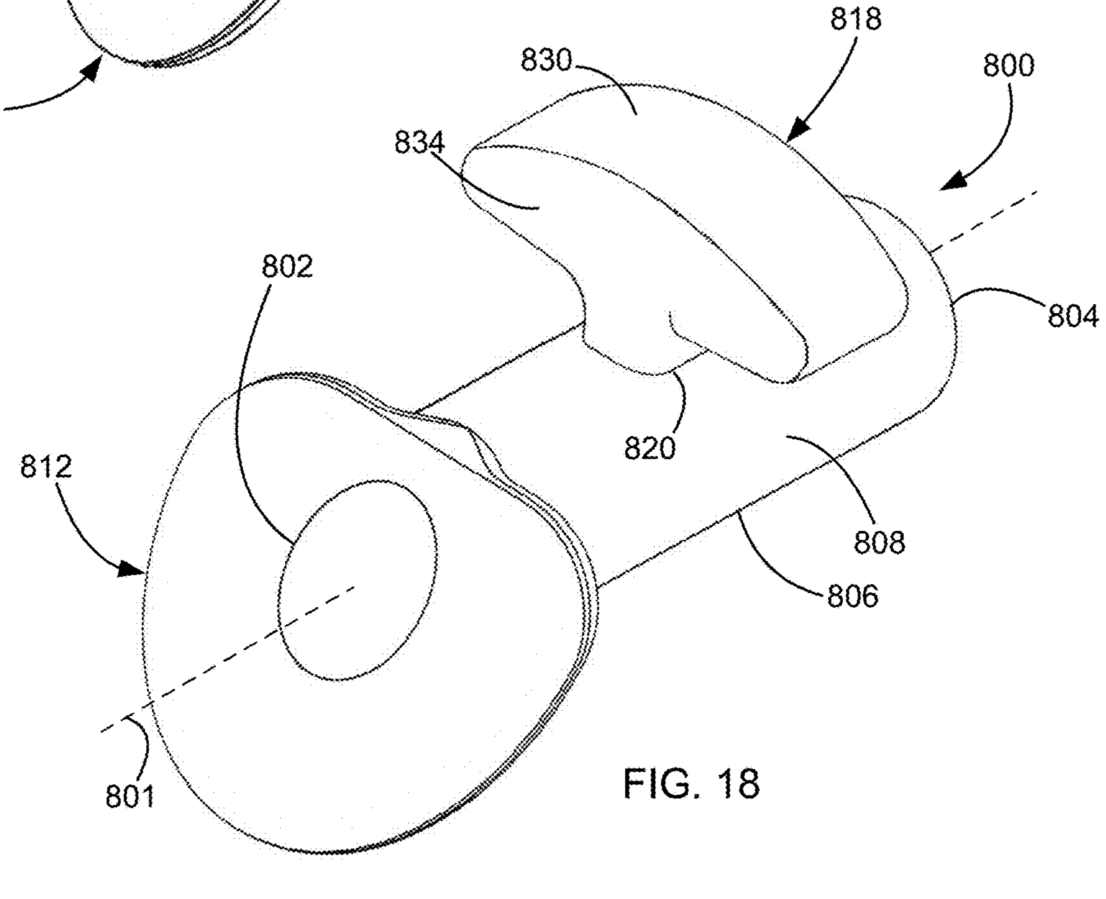
FIG. 18 illustrates a perspective view of a ventilation tube according to another embodiment.
Figure 19:
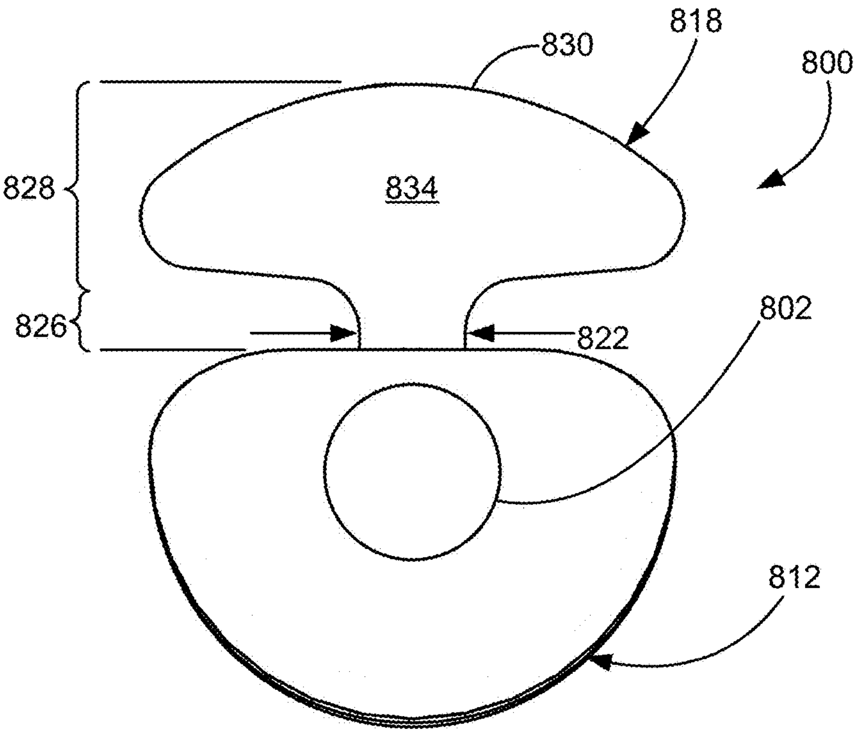
FIG. 19 illustrates a medial end view of FIG. 18.
Figure 20:
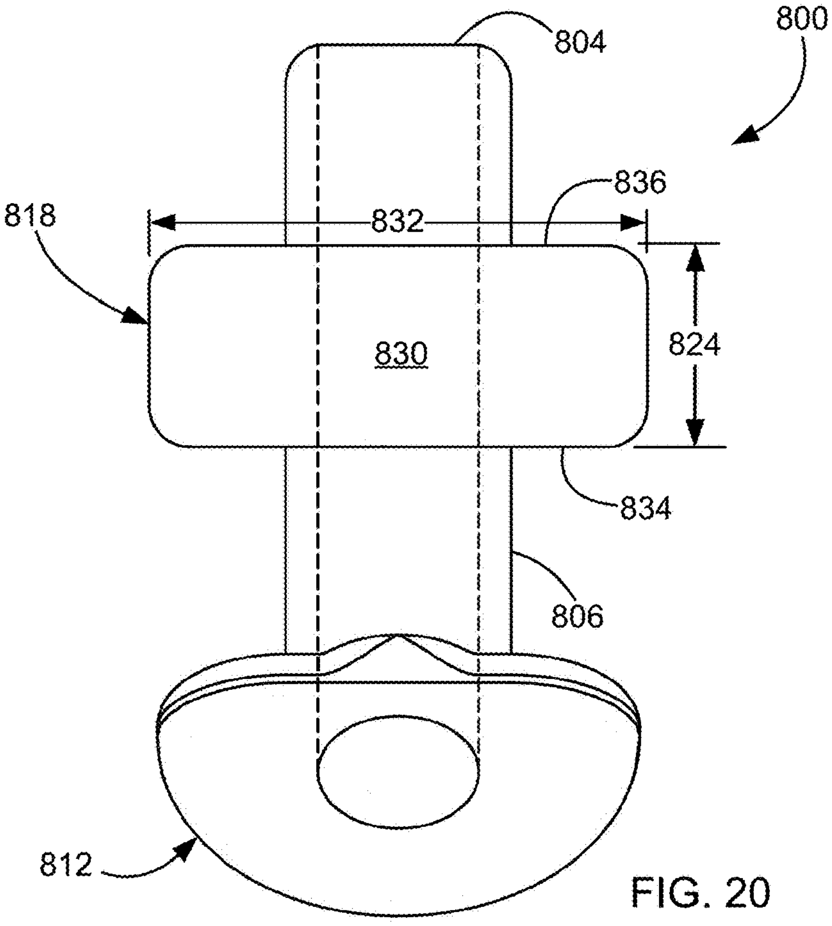
FIG. 20 illustrates a top view of FIG. 18.
Figure 21:
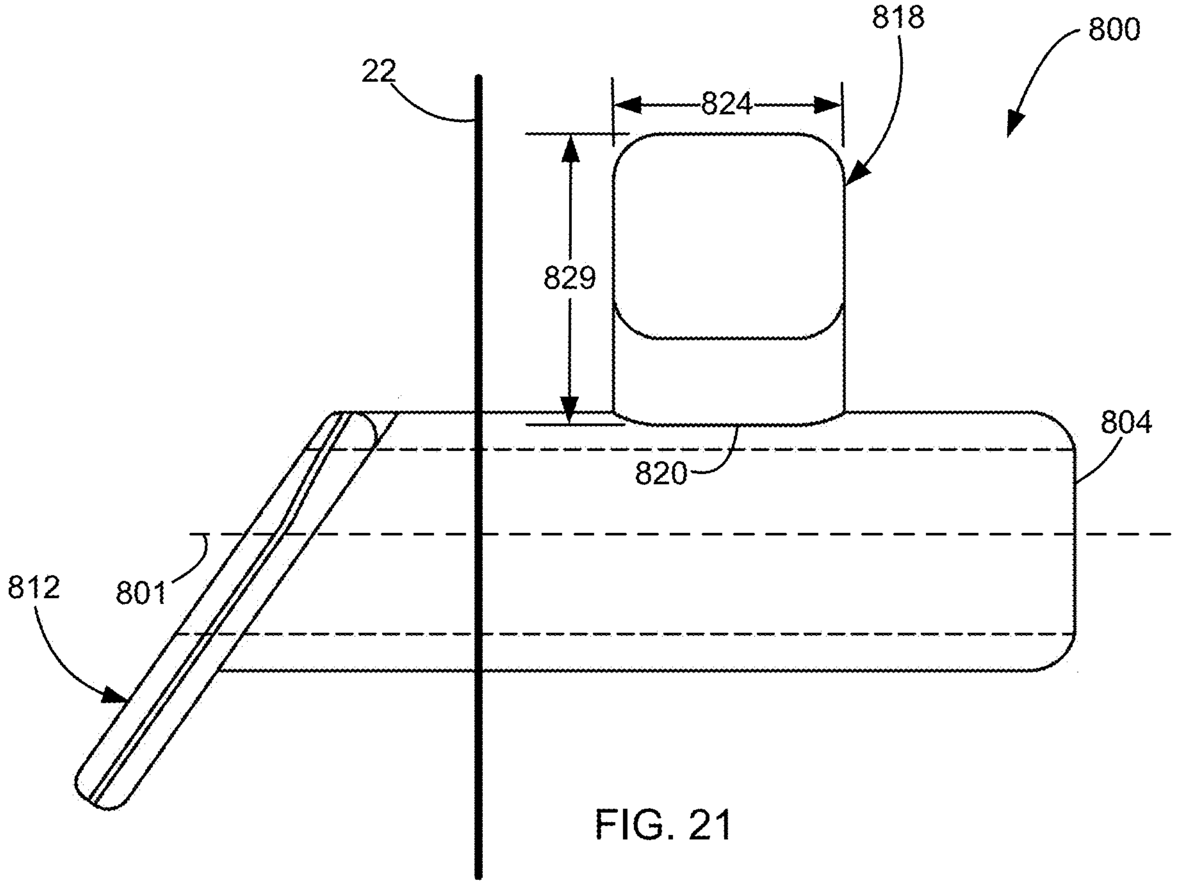
FIG. 21 illustrates a right side view of the ventilation tube illustrated in FIG. 18 as deployed in a membrane of a human body.
Figure 22:
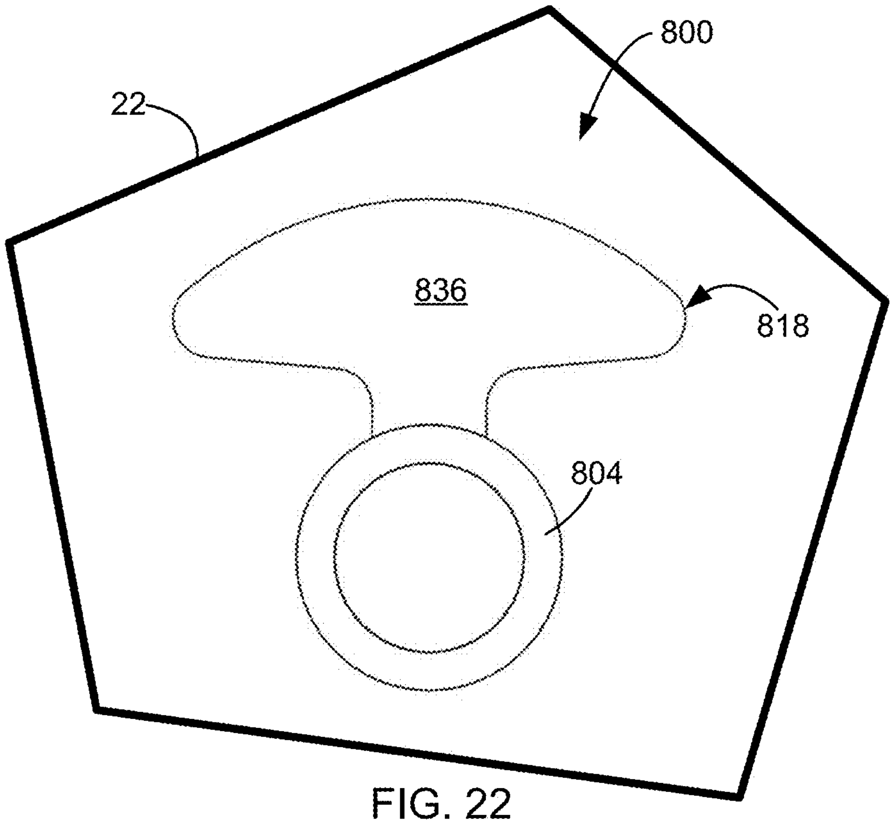
FIG. 22 illustrates a lateral end view of the ventilation tube illustrated in FIG. 21.

FIG. 18 illustrates a perspective view of a ventilation tube 800 according to an embodiment. FIG. 19 illustrates a medial end view, FIG. 20 illustrates a top view and FIG. 21 illustrates a side view and FIG. 22 illustrates a lateral end view of ventilation tube 800 as inserted into membrane 22. Ventilation tube 800 is similar to ventilation tube 100 including a similar hollow body 806 oriented along a central axis 801 and medial flange 812, however, the geometry of lateral tab 818 is different. While lateral tab 818 protrudes and extends from a base end 820 that is coupled to outer facing surface 808 and terminates at a free end 830 like lateral tab 118, lateral tab 818 has a fan-type shape and not a pillar-type shape.

Rather than free end 830 having a planar surface, free end 830 has a curved surface. Like lateral tab 118, lateral tab 818 has a lower portion 826 (FIG. 19) and an upper portion 828 (FIG. 19). Together lower and upper portions 826 and 828 encompass a height 829 (FIG. 21) of lateral tab 818, height 829 being the distance between base end 820 and free end 830. Upper portion 828 includes a first width 832 (FIG. 20) and lower portion 826 includes a second width 822 (FIG. 19). First width 832 of upper portion 828 is greater than second width 822 of lower portion 826 such that lower portion 826 may pass through the slot in a cutting sheath, such as the slot in cutting sheath 36 of FIGS. 6A-6C, and upper portion 828 is positioned to provide greater visibility outwardly from the cutting sheath, such as cutting sheath 36 of FIGS. 6A-6C. In particular, width 832 of upper portion 828 is greater than a width of hollow body 806 and greater than a width of the cutting sheath, such as cutting sheath 36 of FIGS. 6A-6C.

Still further, lateral tab 818 includes a medial-facing side 834 and a lateral-facing side 836. Medial-facing side 834 and lateral-facing side 836 are substantially perpendicular to central axis 801 of hollow body 806. Lateral tab 818 includes a length 824 (FIG. 20) that extends lengthwise along outer facing surface 808 of hollow body 806. Length 824 of lateral tab 818 is located between and spaced apart from medial end 802 (and medial flange 812) and lateral end 804. Length 824 of lateral tab 818 provides haptic feedback (e.g., mechanical resistance) when lateral tab 818 contacts membrane 22 to prevent over insertion. In a deployed state, as is illustrated in FIGS. 21 and 22, medial flange 812 is unfolded and lateral tab 818 is located lateral to membrane 22. Both medial flange 812 and lateral tab 818 are configured to hold tube 800 in membrane 22. FIG. 21 illustrates ventilation tube 800 deployed in tympanic membrane 22, while FIG. 22 illustrates a lateral end view of ventilation tube 800 deployed in tympanic membrane 22.

Figure 23:
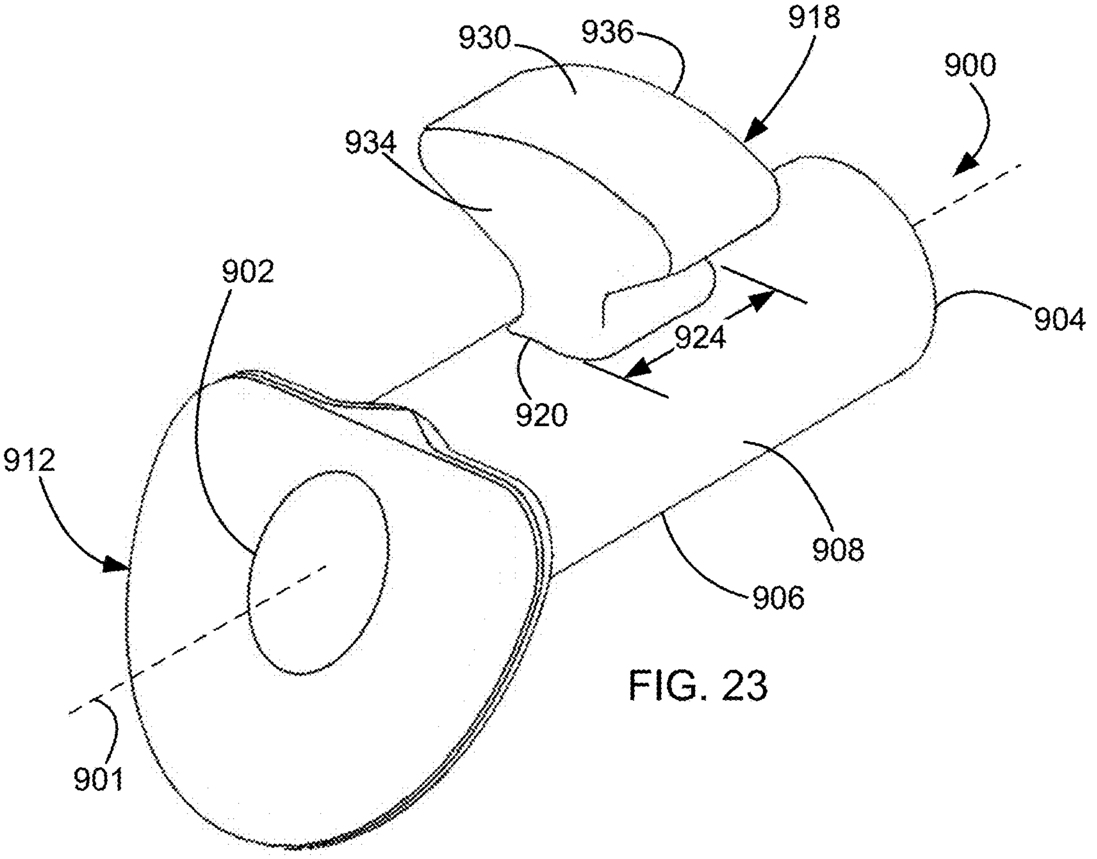
FIG. 23 illustrates a perspective view of a ventilation tube according to another embodiment.
Figure 24:
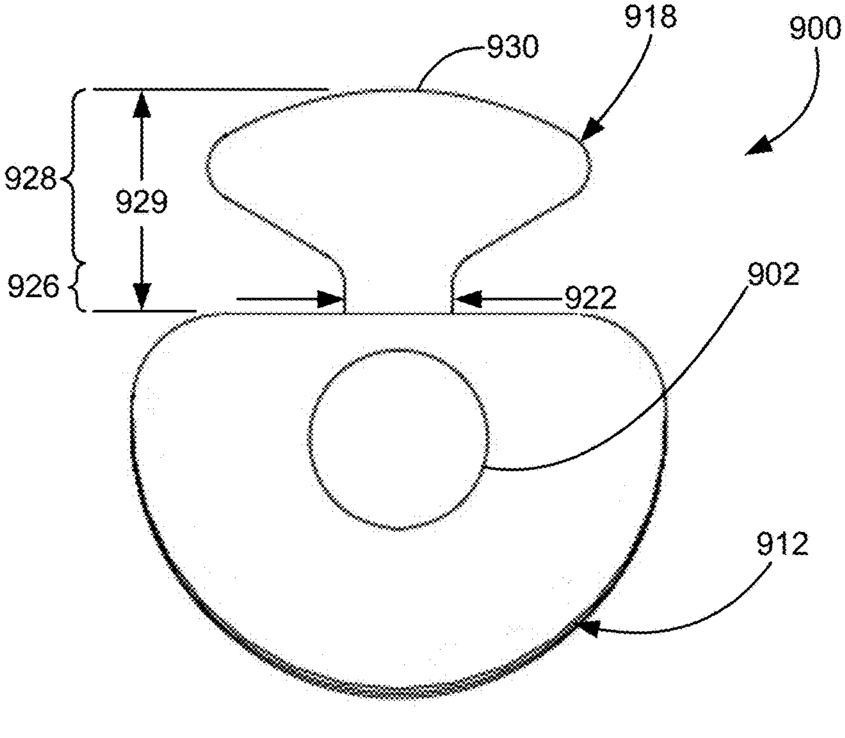
FIG. 24 illustrates a medial end view of FIG. 23.

FIG. 23 illustrates a perspective view of a ventilation tube 900 according to an embodiment. FIG. 24 illustrates a medial end view of ventilation tube 900. Ventilation tube 900 is similar to ventilation tube 800 including a similar hollow body 906 oriented along a central axis 901 and medial flange 912 and fan-type lateral tab 918, however, the geometry of lateral tab 918 is somewhat different. Whereas lateral tab 818 includes close to a 90 degree angle between lower portion 826 and upper portion 828, lateral tab 918 includes an angle between lower portion 926 and upper portion 928 that is greater than 90 degrees and greater than the angle between lower portion 826 and upper portion 828 of lateral tab 818.

Like lateral tab 818, lateral tab 918 includes a curved free end 930. Together lower and upper portions 926 and 928 encompass a height 929 (FIG. 24) that is the distance between base end 920 and free end 930. Lower portion 926 includes width 922 and upper portion 928 includes a width 932. Width 922 of lower portion 926 is less than width 932 of upper portion 928 such that lower portion 926 may pass through the slot in cutting sheath 36 and upper portion 928 is positioned to provide greater visibility outwardly from cutting sheath 36.

Still further, flange or tab 918 includes a medial-facing side 934 and a lateral-facing side 936. Medial-facing side 934 and lateral-facing side 936 are substantially perpendicular to central axis 901 of hollow body 906. However, it should be realized that medial-facing side 934 and lateral-facing side 936 may also be angled relative to central axis 901. Lateral tab 918 includes a length 924 that extends lengthwise along outer facing surface 908 of hollow body 906. Length 924 of lateral tab 918 is located between and spaced apart from medial end 902 (and medial flange 912) and lateral end 904. Length 924 of flange or tab 918 provides haptic feedback (e.g., mechanical resistance) when lateral tab 918 contacts membrane 22 to prevent over insertion.

Figure 25:
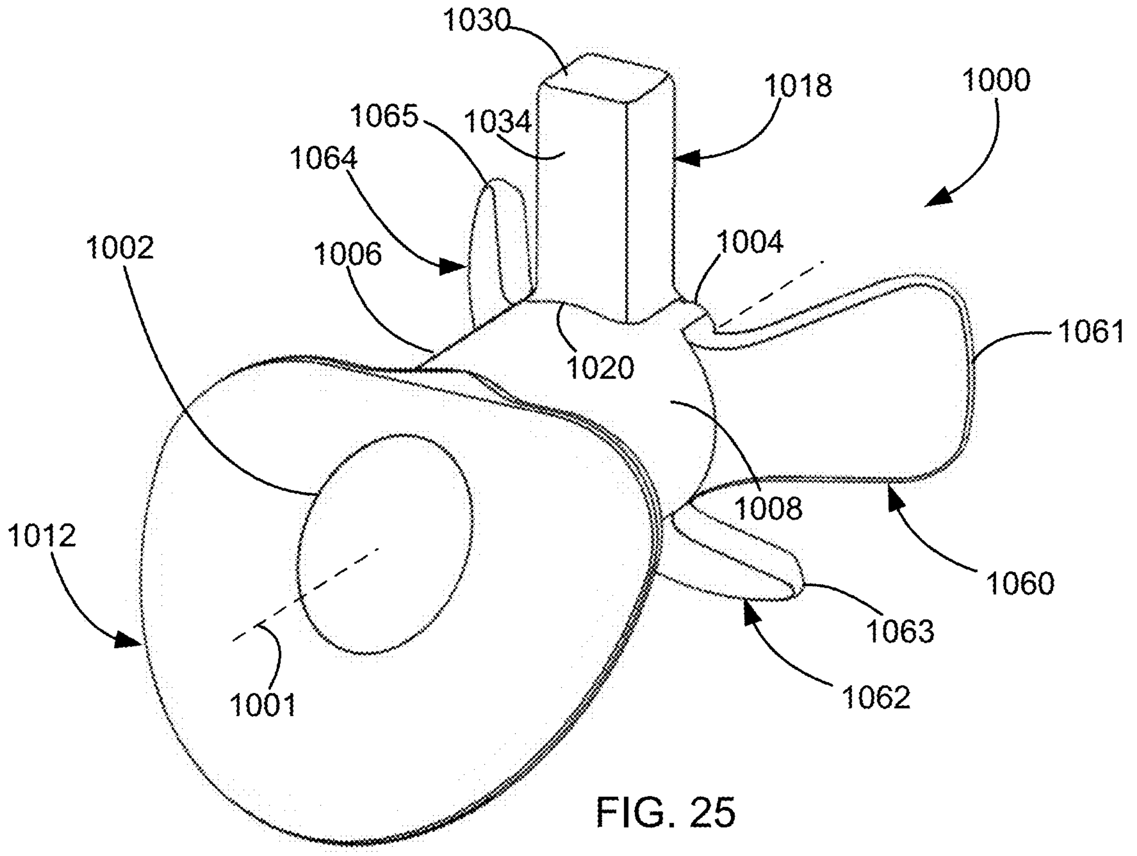
FIG. 25 illustrates a perspective view of a ventilation tube according to another embodiment.
Figure 26:
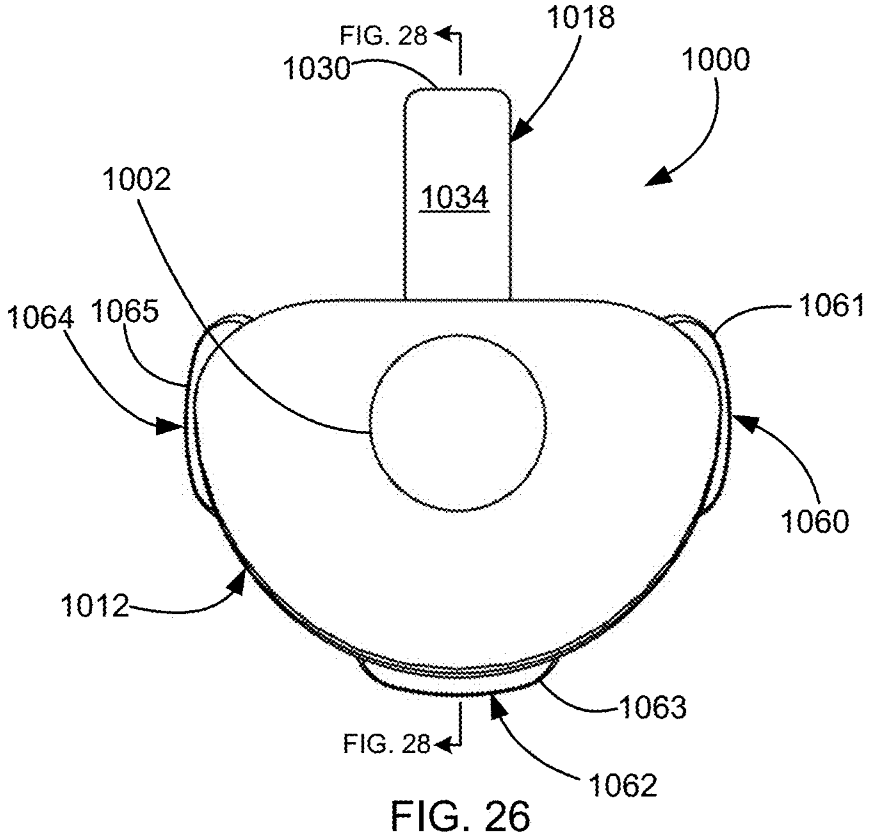
FIG. 26 illustrates a medial end view of the ventilation tube of FIG. 25.
Figure 27:
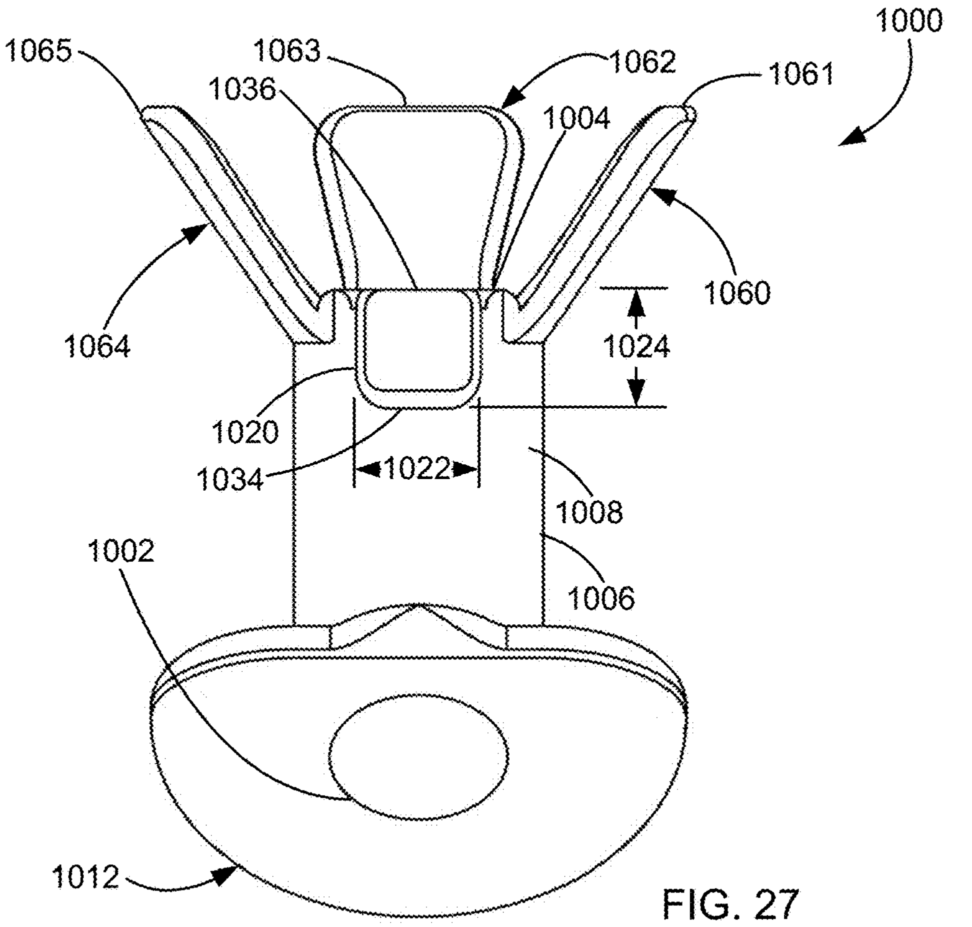
FIG. 27 illustrates a top view of the ventilation tube of FIG. 25.
Figure 28:
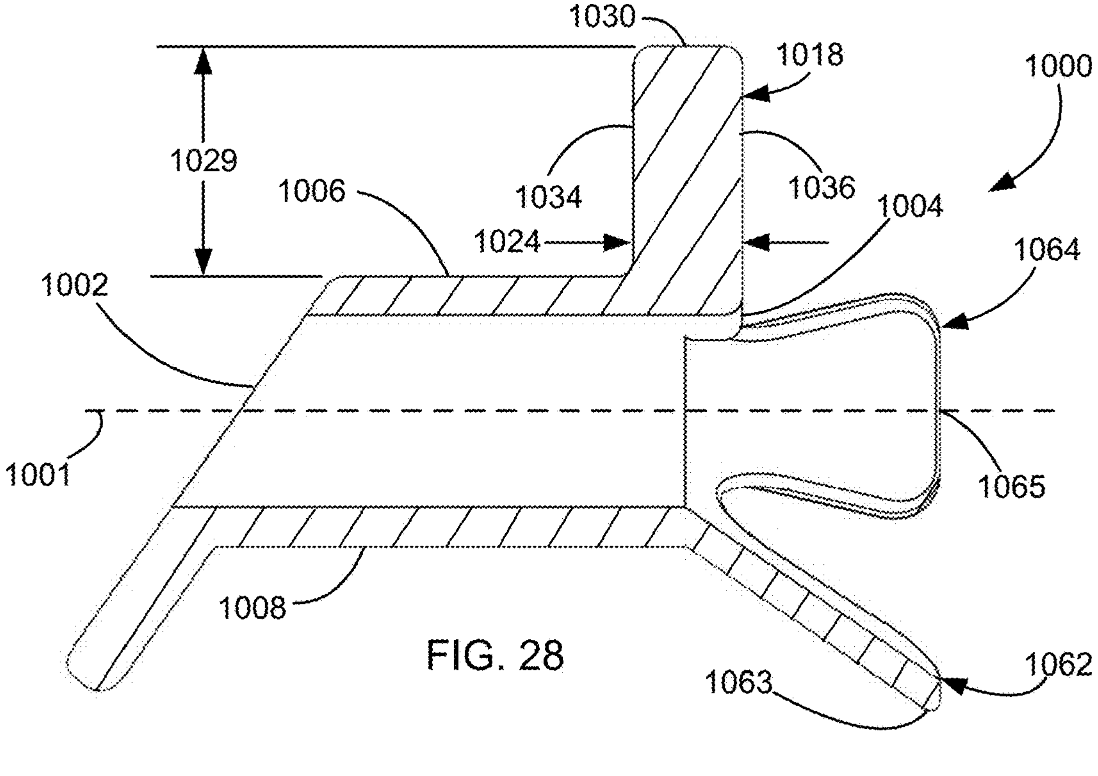
FIG. 28 illustrates a section view of tube of FIG. 25 taken through the section line in FIG. 26.

FIG. 25 illustrates a perspective view of a ventilation tube 1000 according to an embodiment. FIG. 26 illustrates a medial end view, FIG. 27 illustrates a top view and FIG. 28 illustrates a section view of ventilation tube 1000 taken through the section line in FIG. 26. Ventilation tube 1000 includes a medial end 1002, a lateral end 1004 and a hollow body 1006 oriented along a central axis 1001 that extends from medial end 1002 to lateral end 1004. Ventilation tube 1000 is similar to previously described ventilation tubes including having a beveled medial end 1002 and medial flange 1012, however, the geometry of lateral tab 1018 is different than previously described ventilation tubes. A lateral tab 1018 protrudes and extends from a base end 1020 that is coupled to outer facing surface 1008 of hollow body 1006 and terminates at a free end 1030 to encompass a height 1029. Lateral tab 1018 has a pillar-type shape including having a width 1022 and a length 1024 that are substantially the same. Also different from previously described ventilation tubes, lateral tab 1018 is located between and spaced apart from medial end 1002 (and medial flange 1012), but is located adjacent to lateral end 1004. Still further, lateral tab 1018 includes a medial-facing side 1034 and a lateral-facing side 1036. Medial-facing side 1034 and lateral-facing side 1036 are substantially perpendicular to central axis 1001 of hollow body 1006.

It should be understood that lateral tab 1018 is configured as shown in FIGS. 25-28 whether or not ventilation tube 1000 has been inserted into a membrane 22 of the body or not. In other words, lateral tab 1018 is configured in a deployed state whether ventilation tube 1000 is deployed in membrane 22 or not. Ventilation tube 1000 further includes a plurality of lateral flanges including a first lateral flange 1060, a second lateral flange 1062 and a third lateral flange

1064. Each of first, second and third lateral flanges 1060, 1062 and 1064 protrude and extend from lateral end 1004. First, second and third lateral flanges 1060, 1062 and 1064 are different from lateral tab 1018. First, second and third lateral flanges 1060, 1062 and 1064 have different undeployed states and deployed states. FIGS. 25-28 illustrate flanges 1060, 1062 and 1064 in a deployed state. More specifically, free ends 1061, 1063 and 1065 are located outwardly from outer facing surface 1008 of hollow body 1006, while FIGS. 29A and 29B (discussed below) illustrate flanges 1060, 1062 and 1064 in an undeployed state.

Figure 29A:
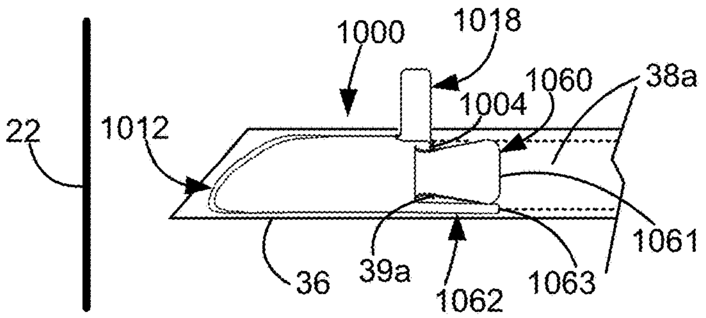
FIGS. 29A-29E illustrate the ventilation tube illustrated in FIGS. 25-28 being deployed in a membrane of a human body.

FIGS. 29A-29E illustrate ventilation tube 1000 of FIGS. 25-28 being deployed in a membrane of a body, such as tympanic membrane 22. In FIG. 29A, ventilation tube 1000 is positioned in a cutting sheath 36 in an undeployed state. In this undeployed state, medial flange 1012 is folded or deformed inwardly to reside inside cutting sheath 36. Lateral tab 1018 protrudes through a slot in cutting sheath 36. The width of the slot in cutting sheath 36 is large enough to accommodate width 1022 of lateral tab 1018. First, second and third lateral flanges 1060, 1062 and 1064 are folded or deformed inwardly to reside inside cutting sheath 36. A positioning rod 38*a* is also located inside cutting sheath 36. In one embodiment, distal end 39*a* of positioning rod 38*a* (shown in broken lines) is positioned adjacent lateral end 1004 and internal located internal to lateral flanges 1060, 1062 and 1064. In another embodiment and not illustrated, a distal end 39*a* of positioning rod 38*a* is positioned adjacent to free ends 1061, 1063 and 1065 of lateral flanges 1060, 1062 and 1064. In yet another embodiment and not illustrated, a distal end 39*a* of positioning rod 38*a* may be shaped to be positioned adjacent to lateral end 1004 and adjacent to free ends 1061, 1063 and/or 1065.

Figure 29B:
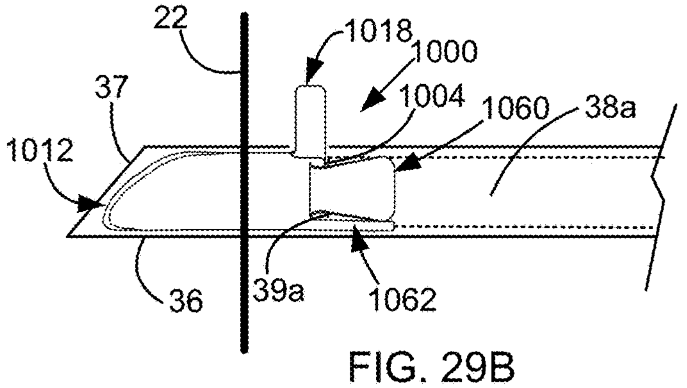

In FIG. 29B, a cutting edge 37 of cutting sheath 36 is advanced through membrane 22 by a clinician to make an incision in membrane 22. Distal end 39*a* of positioning rod 38*a* is held in place against lateral end 1004 or free ends 1061, 1063 and/or 1065 of lateral flanges 1060, 1062 and 1064 to keep tube 1000 in an undeployed state inside of cutting sheath 36. While incising membrane 22, a clinician receives both visual and haptic feedback to ensure ventilation tube 1000 is not being overly inserted or under inserted. In particular, a clinician uses lateral tab 1018 as a visual indicator. As long as the clinician can visualize lateral tab 1018, then tube 1000 has not been overly inserted. A clinician may also use lateral tab 1018 as a haptic feedback indicator. In regards to haptic feedback, a clinician may feel medial-facing side 1034 of lateral tab 1018 contacting membrane 22 as illustrated in FIG. 29B. Such haptic feedback prevents over insertion and under insertion of tube 100.

Figure 29C:
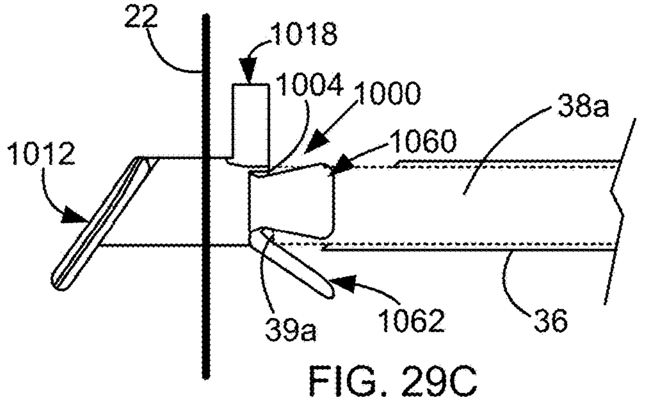
Figure 29D:
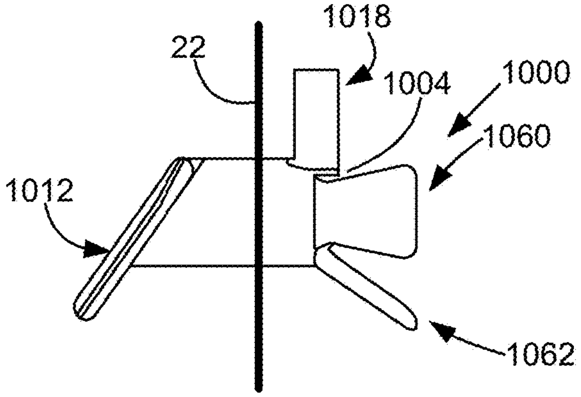
Figure 29E:
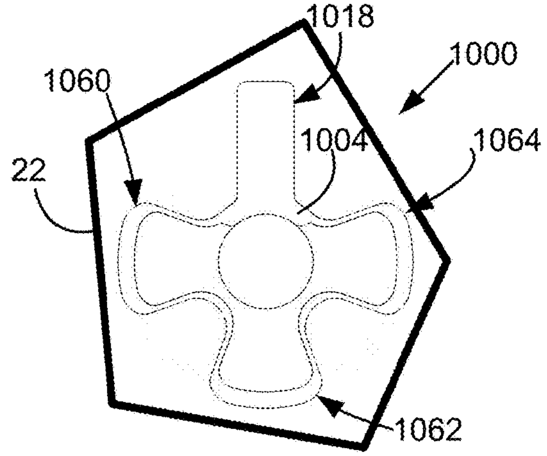

In FIG. 29C, cutting sheath 36 is retracted from around ventilation tube 1000 to deploy tube 1000 into a deployed state, while positioning rod 38*a* holds tube 100 in place. In a deployed state, as is illustrated in FIGS. 29D and 29E, medial flange 1012 is unfolded and is positioned medially to membrane 22, lateral tab 118 remains unchanged and located laterally to membrane 22 and first, second and third lateral flanges 1060, 1062 and 1064 are unfolded and located laterally to membrane 22. Medial flange 1012, lateral tab 1018 and first, second and third lateral flanges 1060, 1062 and 1064 are configured to hold tube 1000 in membrane 22. FIG. 29D illustrates ventilation tube 1000 deployed in tympanic membrane 22, and FIG. 29E illustrates a lateral end view of ventilation tube 1000 deployed in tympanic membrane 22.

The presence of lateral flanges 1060, 1062 and 1064 on ventilation tube 1000 rather than a longer hollow body effectively shortens the lumen length compared to previously described ventilation tubes. This means ventilation tube 1000 is less likely to get plugged because the shortened hollow body 1006 is easier to see through to visualize a plug and the "conical" cross section makes it easier to remove or clear plugs. For example, squeezing a conical-shaped part (when the part is made of a flexible materials such as silicone) is more effective at ejecting the plug as opposed to a plug in a lumen with a longer cylindrical lumen. In addition, lateral flanges 1060, 1062 and 1064 increase the resistance of tube medialization. In other words, lateral flanges 1060, 1062, and 1064 prevent ventilation tube 1000 from migrating inside the middle ear of the patient.

Figure 30:
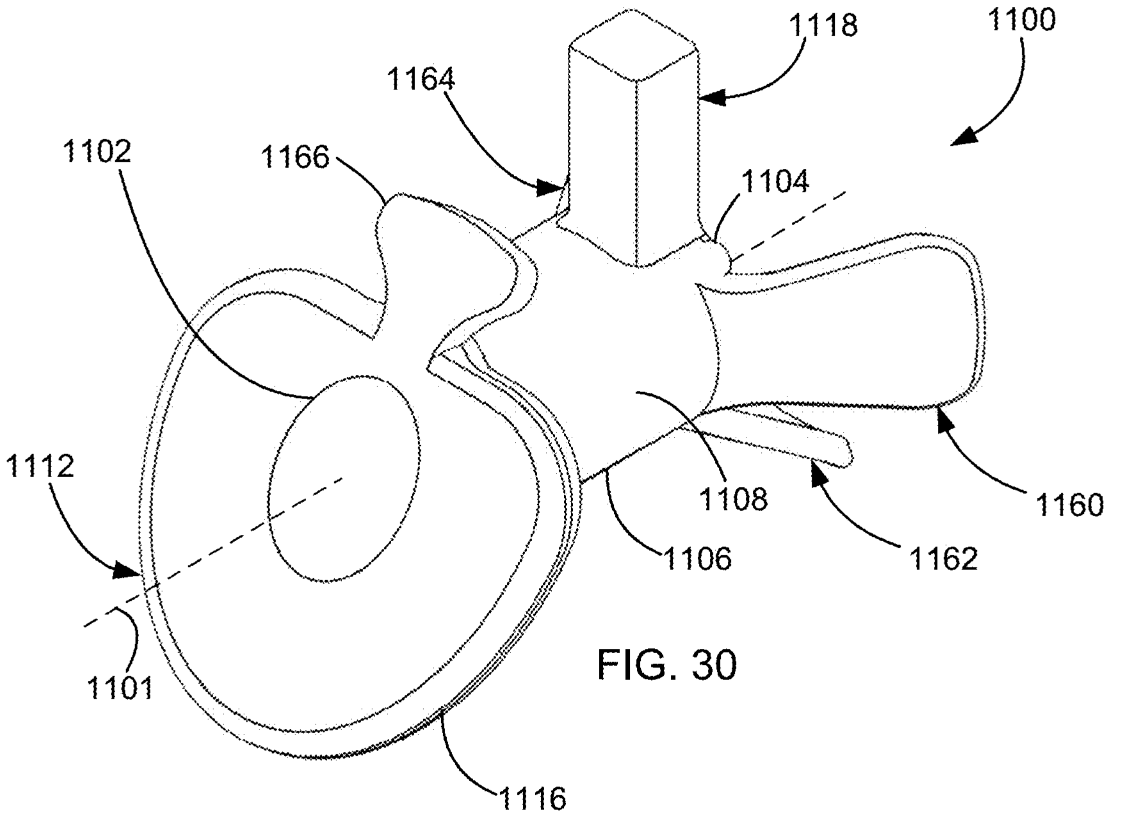
FIG. 30 illustrates a perspective view of a ventilation tube according to yet another embodiment.
Figure 31:
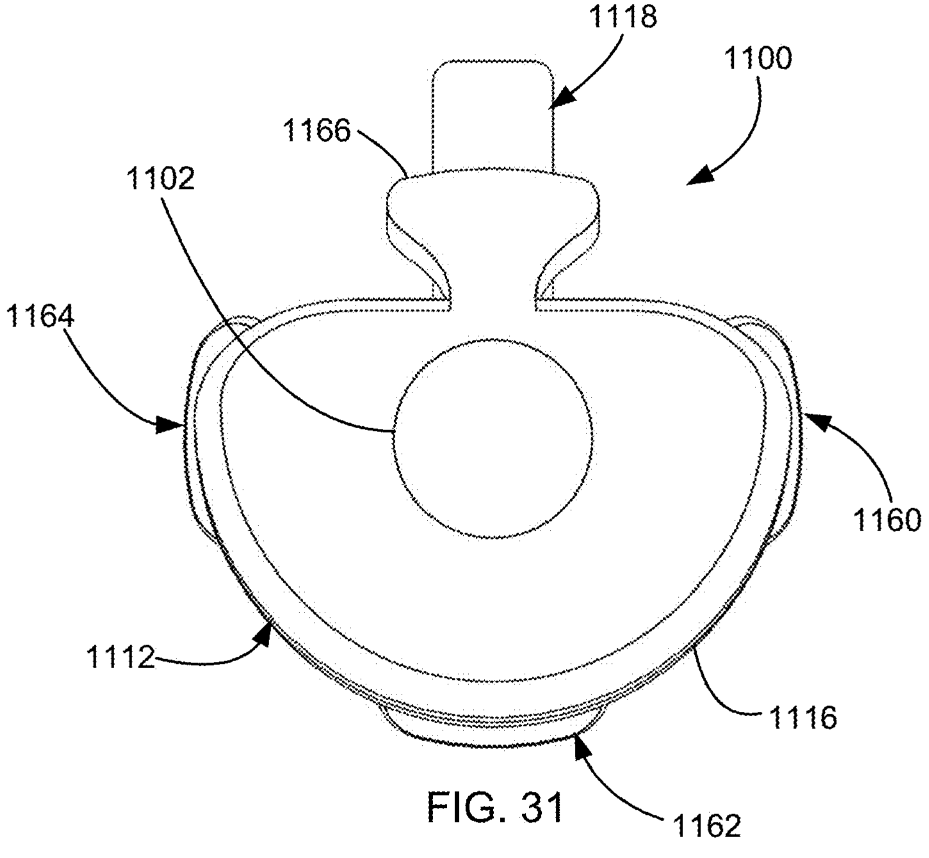
FIG. 31 illustrates medial end view of FIG. 30.
Figure 32:
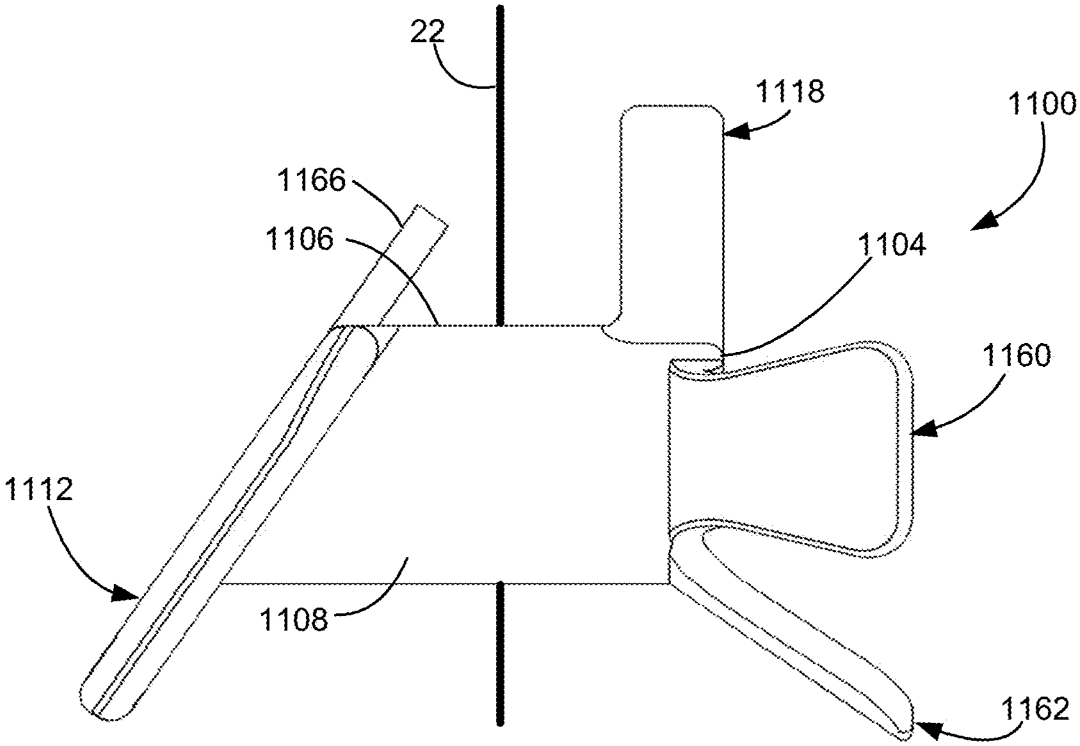
FIG. 32 illustrates a right side view of the ventilation tube illustrated in FIG. 29 as deployed in a membrane of a human body.
Figure 33:
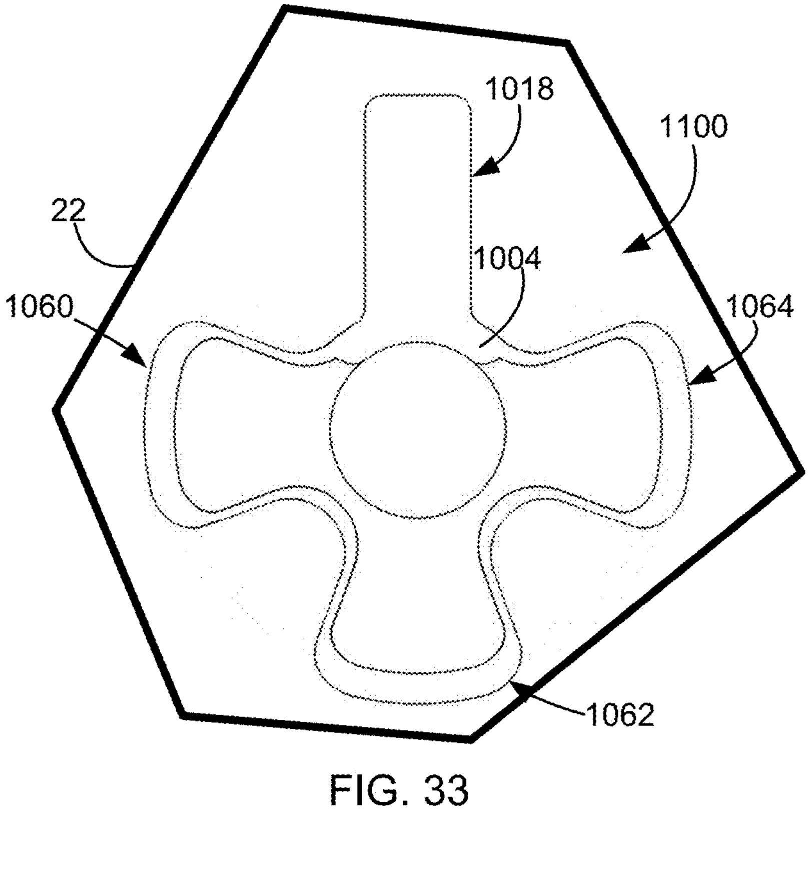
FIG. 33 illustrates a lateral end view of the ventilation tube illustrated in FIG. 31.

FIG. 30 illustrates a perspective view of a ventilation tube 1100 according to an embodiment. FIG. 31 illustrates a medial end view of ventilation tube 1100, FIG. 32 illustrates a side view and FIG. 33 illustrates a lateral end view of ventilation tube 1100 as inserted into membrane 22. Ventilation tube 1100 is similar to ventilation tube 1000 including a similar hollow body 1106 that is oriented along a central axis 1101, a lateral tab 1118 and first, second and third lateral flanges 1160, 1162 and 1164, however, medial flange 1112 is different. While medial flange 1112 follows the beveled angle of medial end 1102, has a portion of medial flange 1112 that is in alignment with outer facing surface 1108 of hollow body 1106 (giving medial flange 1112 the appearance of having a flat edge) and a remaining portion of medial flange 1112 that extends outwardly from outer facing surface 1108 (along a curved edge 1116), medial flange 1112 further includes a medial visualization tab 1166. Medial visualization tab 1166 extends or protrudes from the portion of medial flange 1112 that is in alignment with outer facing surface 1108 (or the flat edge). Furthermore, medial visualization tab 1166 is in alignment with lateral flange or tab 1118.

In the FIGS. 30-33 embodiment, not only does lateral tab 1118 protrude through a slot in cutting sheath 36 before ventilation tube 1100 is deployed, but medial visualization tab 1166 also protrudes through the slot in cutting sheath 36, while the curved edge 1116 of medial flange 1112 is folded inside cutting sheath 36. Medial visualization tab 1166 is made of a flexible material and is thin enough so that when the incision in membrane 22 is excised by the cutting edge of cutting sheath 36, visualization tab 116 is easily insertable through the incised incision. Therefore, when medial visualization tab 1166 is no longer visible to the clinician, this lack of sighting of the medial visualization tab 1166 is indicative of medial flange 1112 being in the correct location in the middle ear of the patient and ventilation tube 1100 being inserted to a sufficient depth.

Figure 34:
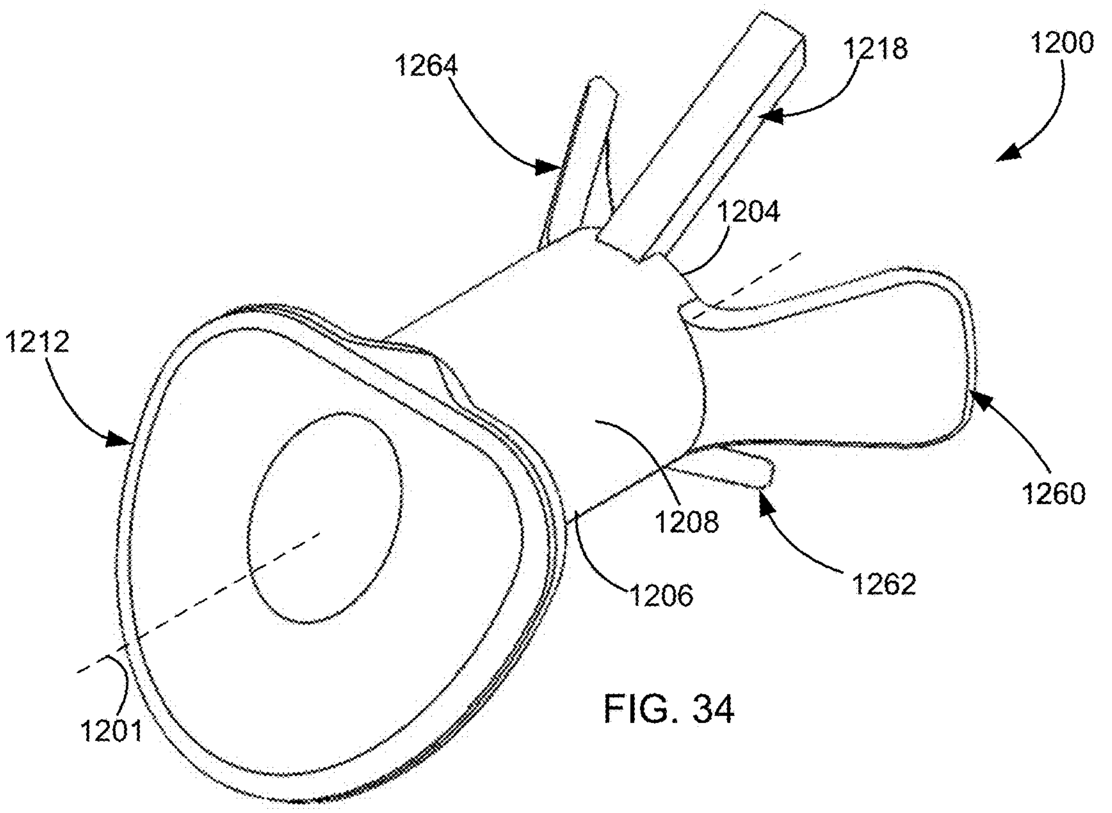
FIG. 34 illustrates a perspective view of a ventilation tube according to yet another embodiment.
Figure 35:
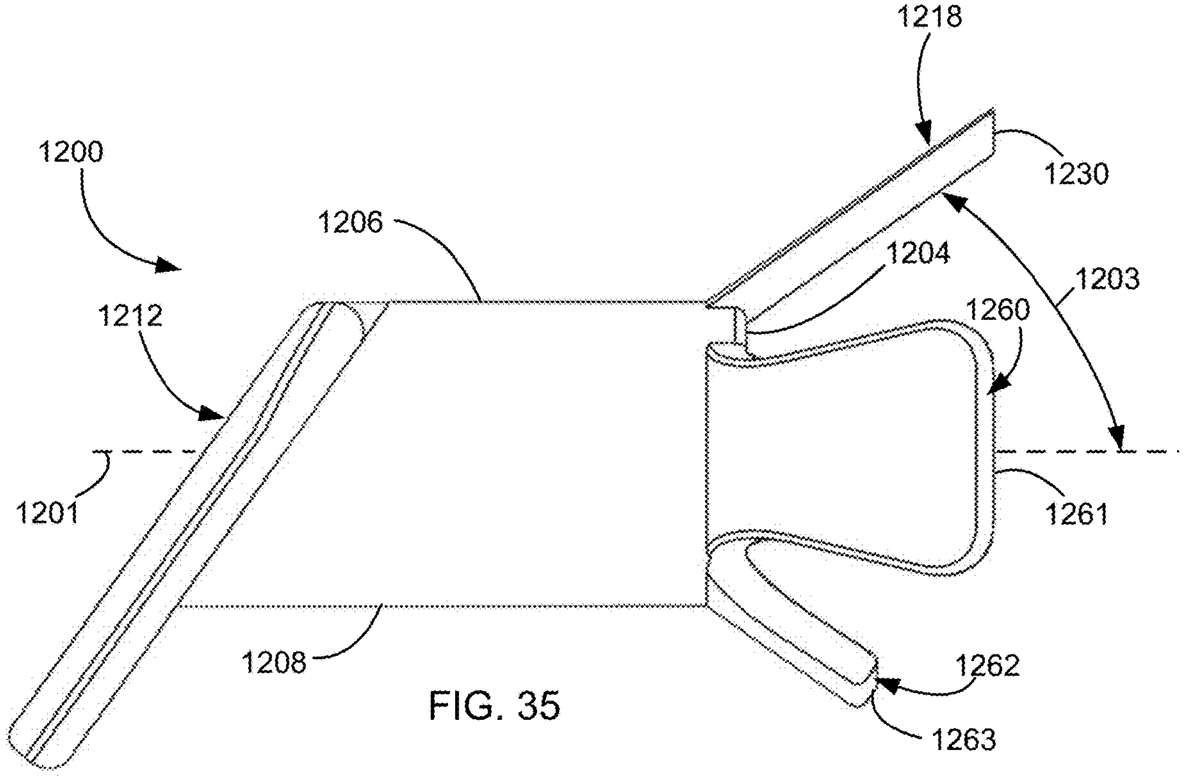
FIG. 35 illustrates a right side view of the ventilation tube of FIG. 34.

FIG. 34 illustrates a perspective view and FIG. 35 illustrates a side view of a ventilation tube 1200 according to an embodiment. Ventilation tube 1200 is similar to ventilation tube 1100 including a similar hollow body 1206, medial flange 1212 and first, second and third lateral flanges 1260, 1262 and 1264, however, at least lateral tab 1218 is different. Rather than lateral tab 1218 being substantially perpendicular to a central axis 1201 of hollow body 1206, lateral tab 1218 is oriented at an angle that is less than 90 degrees from the central axis of hollow body 1206. As illustrated in FIGS. 34 and 35, first lateral flange or tab 1218 is oriented at an angle 1203 that is approximately 45 degrees from central axis 1201 of hollow body 1206. Each of flanges 1260, 1262 and 1264 are also oriented at an angle from central axis 1201, which may be the same or different than angle 1203. In one embodiment, all flanges 1260, 1262, 1264 and 1218 are oriented at angle 1203 from central axis 1201.

In another difference, while first, second and third lateral flanges 1260, 1262 and 1264 have a similar shape and orientation as illustrated in the FIGS. 25-33 embodiments, lateral flanges 1260, 1262 and 1264 may vary in thickness and in length. As illustrated in FIG. 35, a length (extending from lateral end 1204 to free end 1263) of lateral flange 1262 is less than a length (extending from lateral end 1204 to free end 1261) of lateral flange 1260. Furthermore, a length of lateral tab 1218 may also include a length that is different from the lengths of lateral flanges 1260, 1262 and 1264. As illustrated in FIG. 35, a length of lateral tab 1218 (extending from lateral end 1204 to free end 1230) is greater than the length of either flange 1262 or flange 1264.

Figure 36:
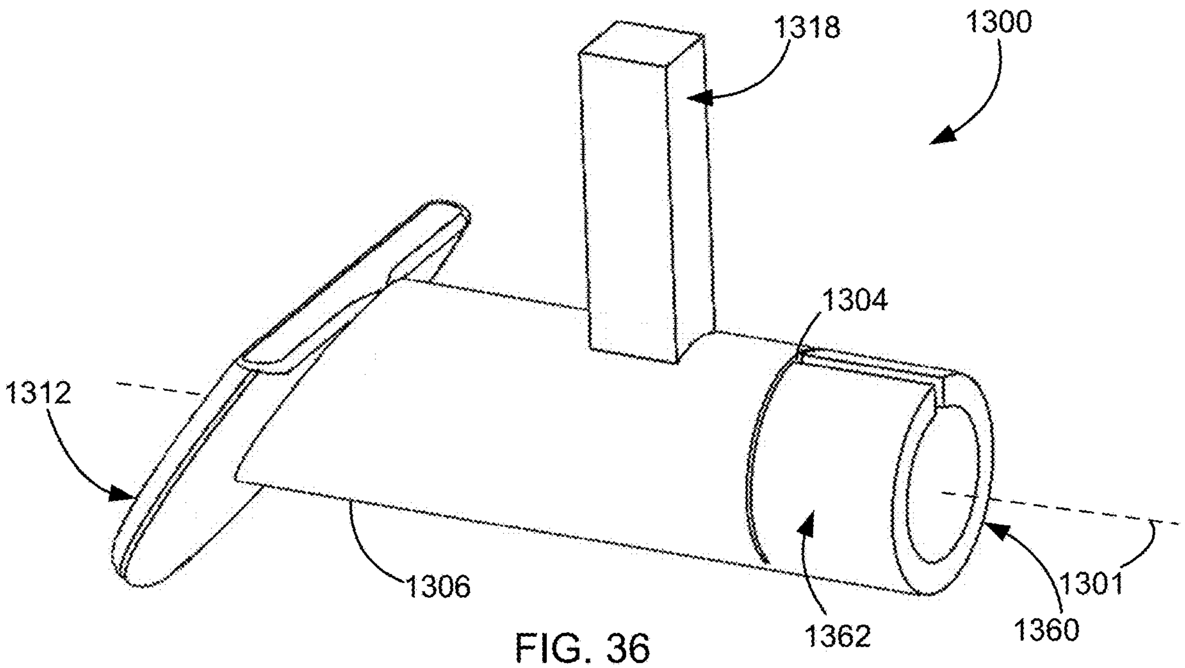
FIG. 36 illustrates a first perspective view of a ventilation tube in an undeployed state according to an embodiment.
Figure 37:
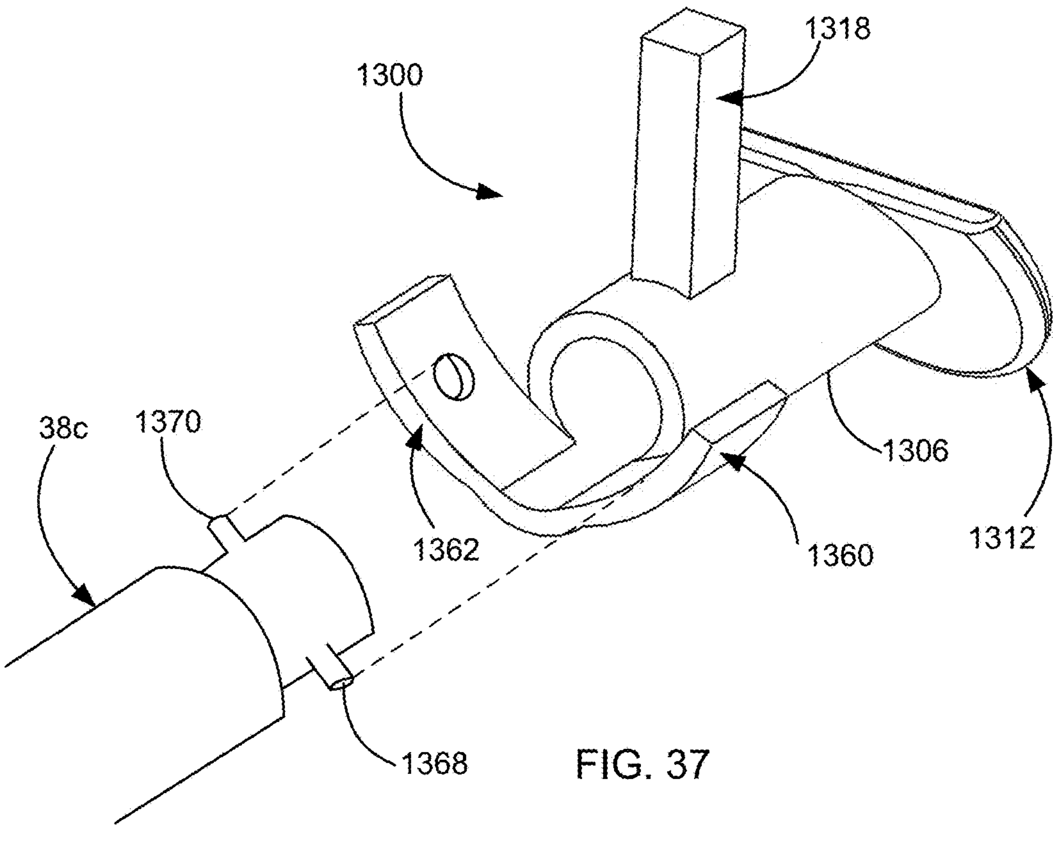
FIG. 37 illustrates a second perspective view of the ventilation tube in FIG. 36 in a deployed state according to an embodiment.

FIG. 36 illustrates a first perspective view of a ventilation tube 1300 in an undeployed state according to an embodiment, and FIG. 37 illustrates a second perspective view of ventilation tube 1300 in a deployed state showing a distal portion of a positioning rod 38*c* according to an embodiment. Ventilation tube 1300 is similar to ventilation tube 1000 including a similar hollow body 1306, medial flange 1312 and lateral tab 1318, however, lateral flanges located at lateral end 1304 are different. As illustrated in the undeployed state in FIG. 35, first and second lateral flanges 1360 and 1362 are rolled up and oriented around lateral end 1304 or about a central axis 1301 of hollow body 1306. While FIG. 36 illustrates two flanges 1360 and 1362, more flanges are possible.

In the deployed state illustrated in FIG. 37, first and second lateral flanges 1360 and 1362 unroll upon the cutting sheath being retracted. To enable a positioning rod to function, FIG. 36 illustrates an embodiment of positioning rod 38*c* showing a pair of nubs 1368 and 1370 that would mate with apertures in second and third lateral flanges 1360 and 1362. Nubs 1368 and 1370 are configured to hold flanges 1360 and 1362 rolled up in a cutting sheath and keep ventilation tube 1300 in place upon retraction of the cutting sheath. Upon retracting of the cutting sheath, lateral flanges 1360 and 1362 would unfold and be released from nubs 1368 and 1370 of positioning rod 38*c* so that the positioning rod 38*c* may be removed.

In the embodiment illustrated in FIGS. 36 and 37, hollow body 1306 includes a long lumen length for ease of insertion into a membrane. However, upon deployment of lateral flanges 1360 and 1362, the effective length of the lumen decreases. As discussed above, a shorter lumen length reduces drainage that is exiting through the lumen from plugging and makes it easier to visualize and clear plugging in the lumen.

Figure 38:
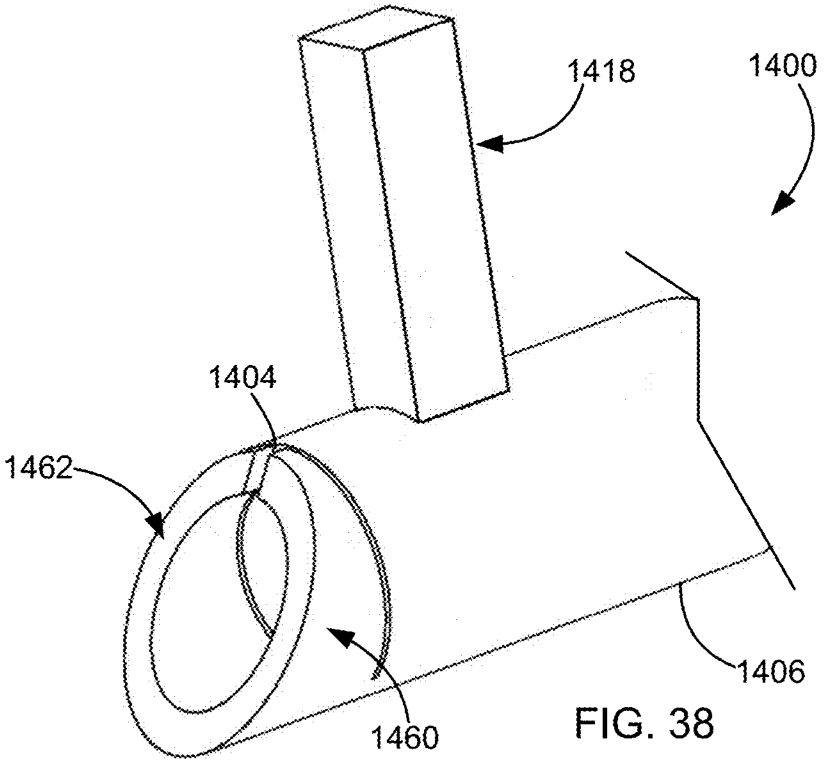
FIG. 38 illustrates a first perspective view of a ventilation tube in an undeployed state according to an embodiment.
Figure 39:
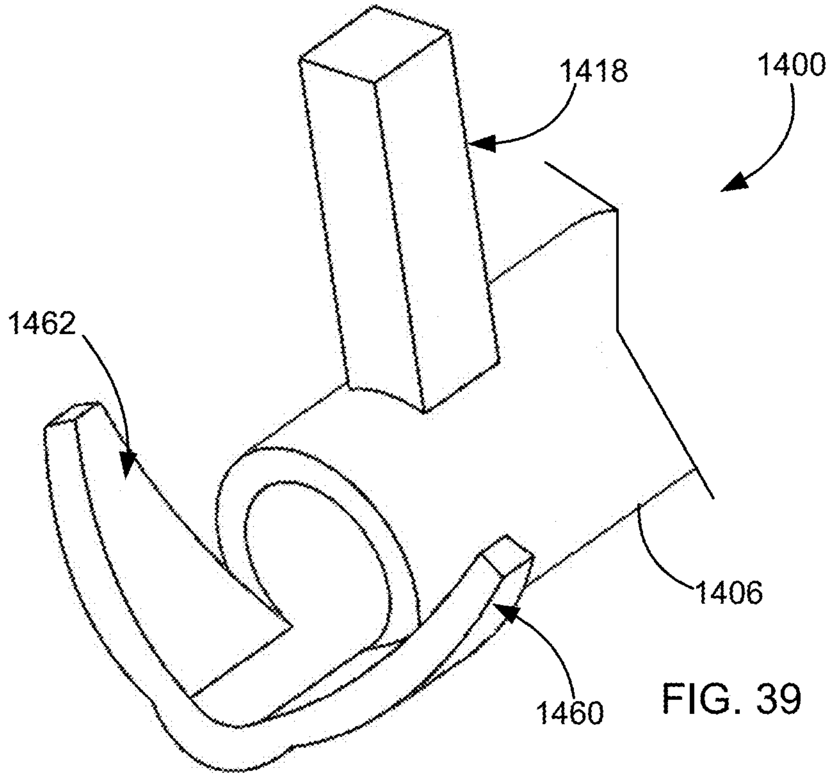
FIG. 39 illustrates a second perspective view of the ventilation tube in FIG. 38 in a deployed state according to an embodiment.

FIG. 38 illustrates a first perspective view of a ventilation tube 1400 in an undeployed state according to an embodiment, and FIG. 39 illustrates a second perspective view of ventilation tube 1400 in a deployed state according to an embodiment. Ventilation tube 1400 is similar to ventilation tube 1300 including a similar hollow body 1406 and lateral tab 1418. However, the medial flange is comprised of first medial flange 1460 and second medial flange 1462. Rather than first medial flange 1460 and second medial flange 1462 folding up axially in the undeployed state, the free ends of first medial flange 1460 and second medial flange 1462 are rolled up around a central axis of hollow body 1406. In this embodiment, the medial flange geometry in the undeployed state can match the beveled geometry of a cutting sheath, without increasing the depth of insertion needed to position the medial flange fully behind the TM during insertion.

Figure 40:
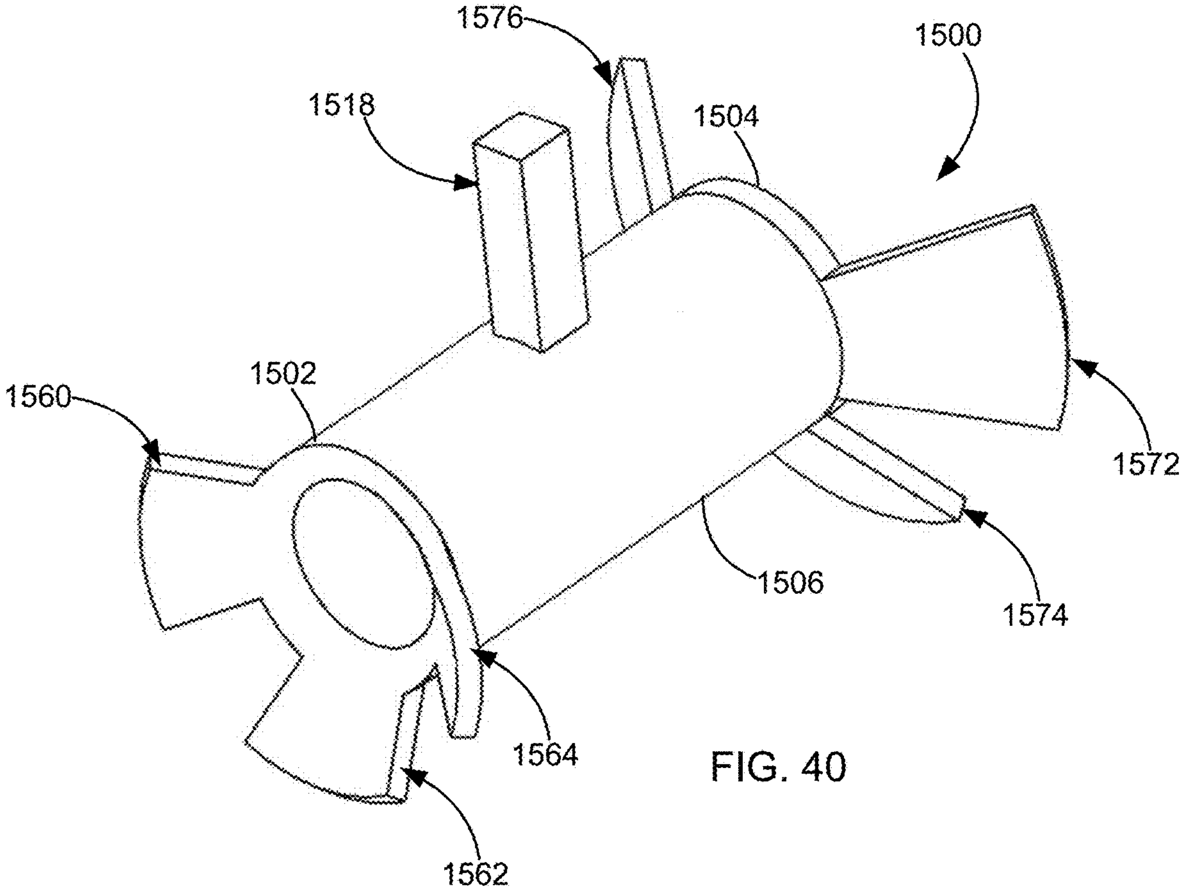
FIG. 40 illustrates a perspective view of a ventilation tube according to yet another embodiment.
Figure 41:
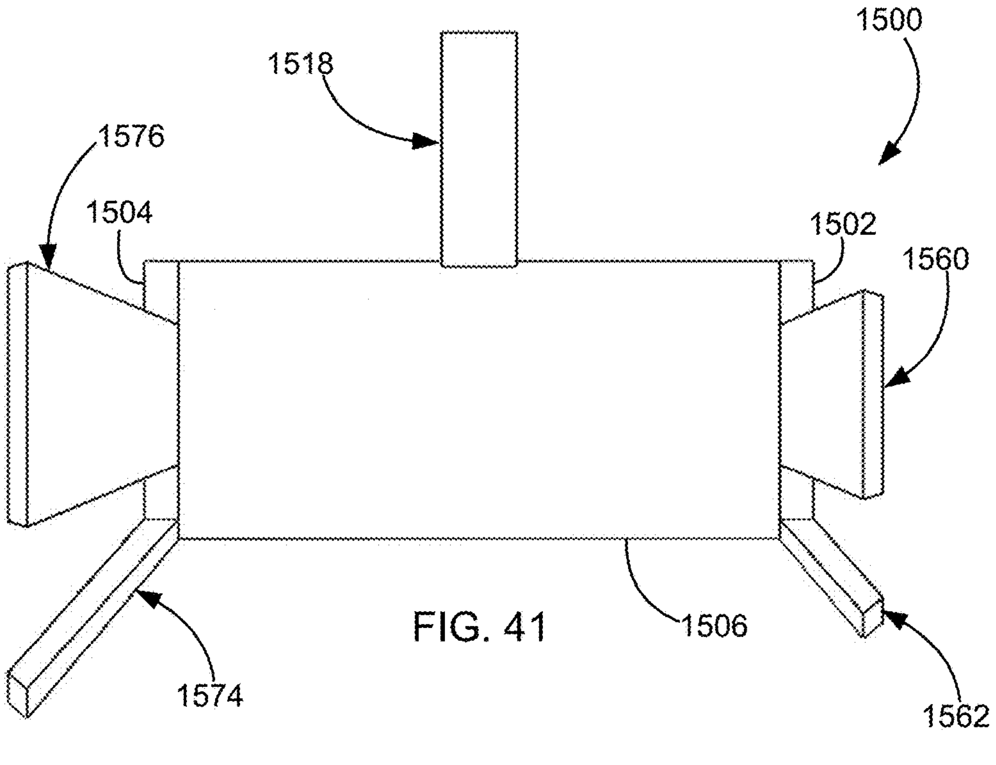
FIG. 41 illustrates a right side view of the ventilation tube of FIG. 40.

FIG. 40 illustrates a perspective view and FIG. 41 illustrates a side view of a ventilation tube 1500 in a deployed state according to an embodiment. Tube 1500 is constructed to be a reversible tube. More specifically, similar flange geometry is located on both ends 1502 and 1504, such that end 1502 may be either a lateral end or a medial end and end 1504 may be either a lateral end or a medial end. A tab 1518 extends from outer facing surface 1508 of hollow body 1506 and may, under one embodiment, be located in the middle of hollow body 1506. Each end 1502 and 1504 includes a plurality of flanges 1560, 1562, 1564, 1572, 1574 and 1576, where flanges 1560, 1562 and 1564 at end 1502 are similar to the flanges 1572, 1574 and 1576 at end 1504. However, under one embodiment and as illustrated in FIGS. 40 and 41, flanges 1560, 1562 and 1564 at end 1402 include a length (extending from end 1402 to free ends) that is less than a length (extending from end 1504 to free ends) of flanges 1572, 1574 and 1576 at end 1504. In this way, either the longer or shorter flanges may be chosen to be placed medial to membrane 22.

Figure 42:
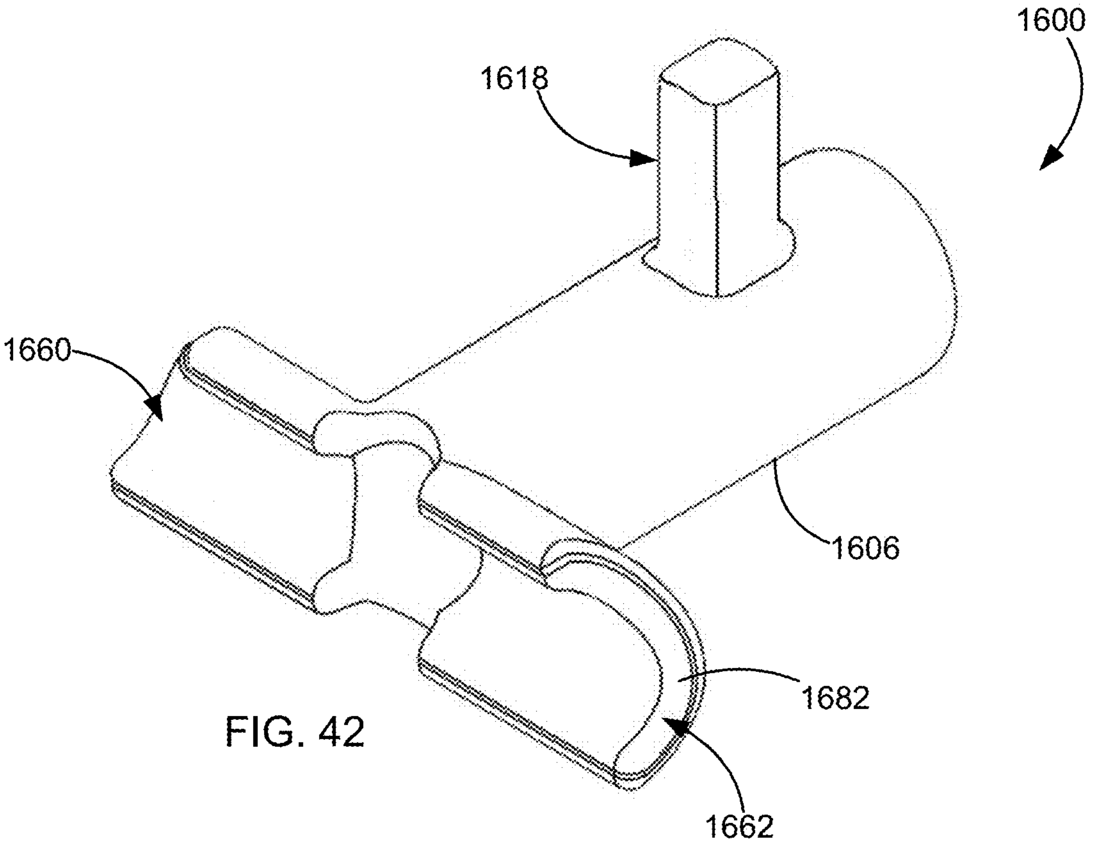
FIG. 42 illustrates a perspective view of a ventilation tube according to yet another embodiment.
Figure 43:
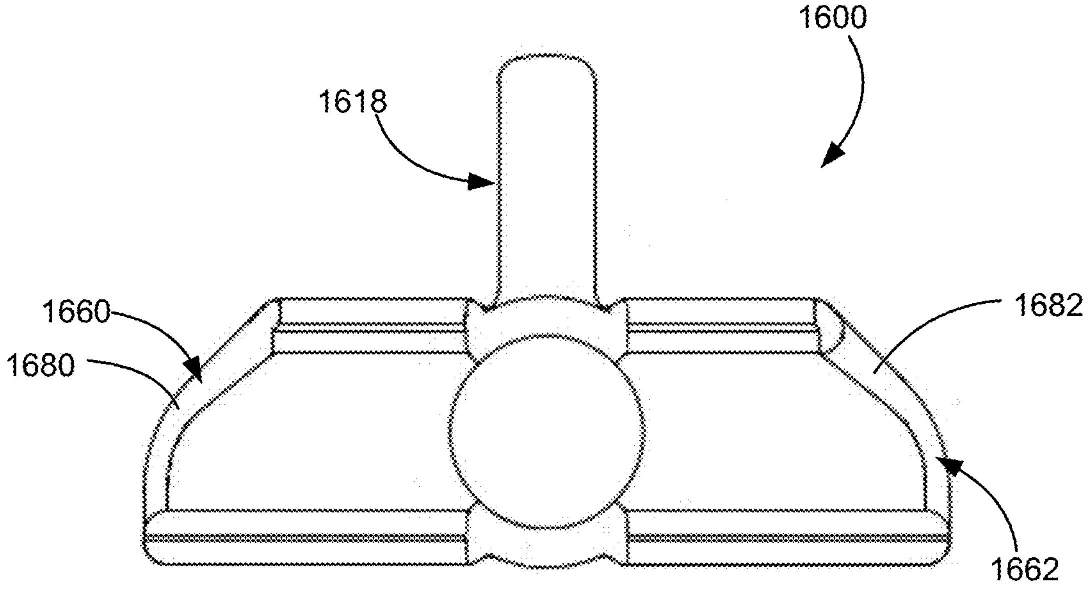
FIG. 43 illustrates a medial end view of the ventilation tube of FIG. 42.

FIG. 42 illustrates a perspective view and FIG. 43 illustrates a medial end view of a ventilation tube 1600 in a deployed state according to an embodiment. Ventilation tube 1600 is a style of tube referred to as a T-tube. T-tube 1600 includes a hollow body 1606 having a pair of medial flanges 1660 and 1662 that are to be located medial to membrane 22. T-tube 1600 also includes lateral tab 1618 similar to lateral tabs 1018, 1118, 1318, 1418 and 1518 in previously described embodiments. Lateral tab 1618 is be located lateral to membrane 22 and configured to be a visual marker so that T-tube 1600 is not over-inserted. However, it should be realized that any of the lateral tabs discussed in previous embodiment may be used with the medial flanges 1660 and 1662 including, for example, tabs 118, 218, 318, 818 and 918.

Figure 44:
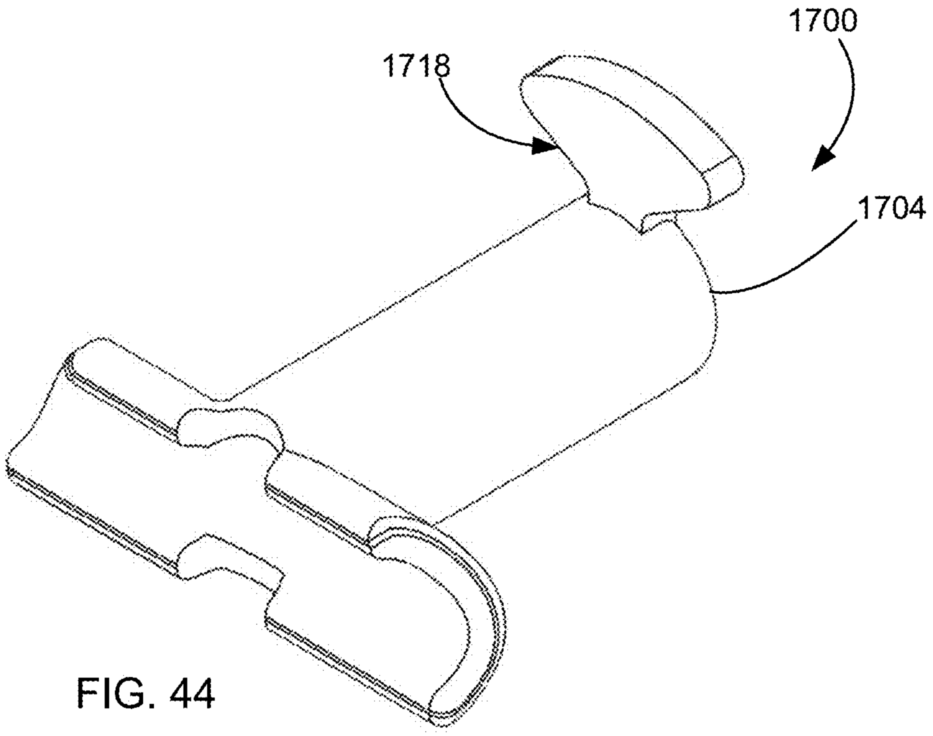
FIG. 44 illustrates a perspective view of a ventilation tube according to yet another embodiment.

As illustrated in FIGS. 42 and 43, medial flanges 1660 and 1662 include bevel ends 1680 and 1682 so as to interface with the beveled end of the cutting edge of cutting sheath 36. Beveled ends 1680 and 1682 minimize the depth of penetration past membrane 22 that is needed to allow medial flanges 1660 and 1662 to unfold after cutting sheath 36 is retracted. FIG. 44 illustrates a perspective view of a ventilation tube 1700 according to another embodiment. While ventilation tube 1700 is similar to ventilation tube 1600, ventilation tube 1700 includes a lateral tab 1718 that has a fan-type geometry and is located at lateral end 1704.

Figure 45:
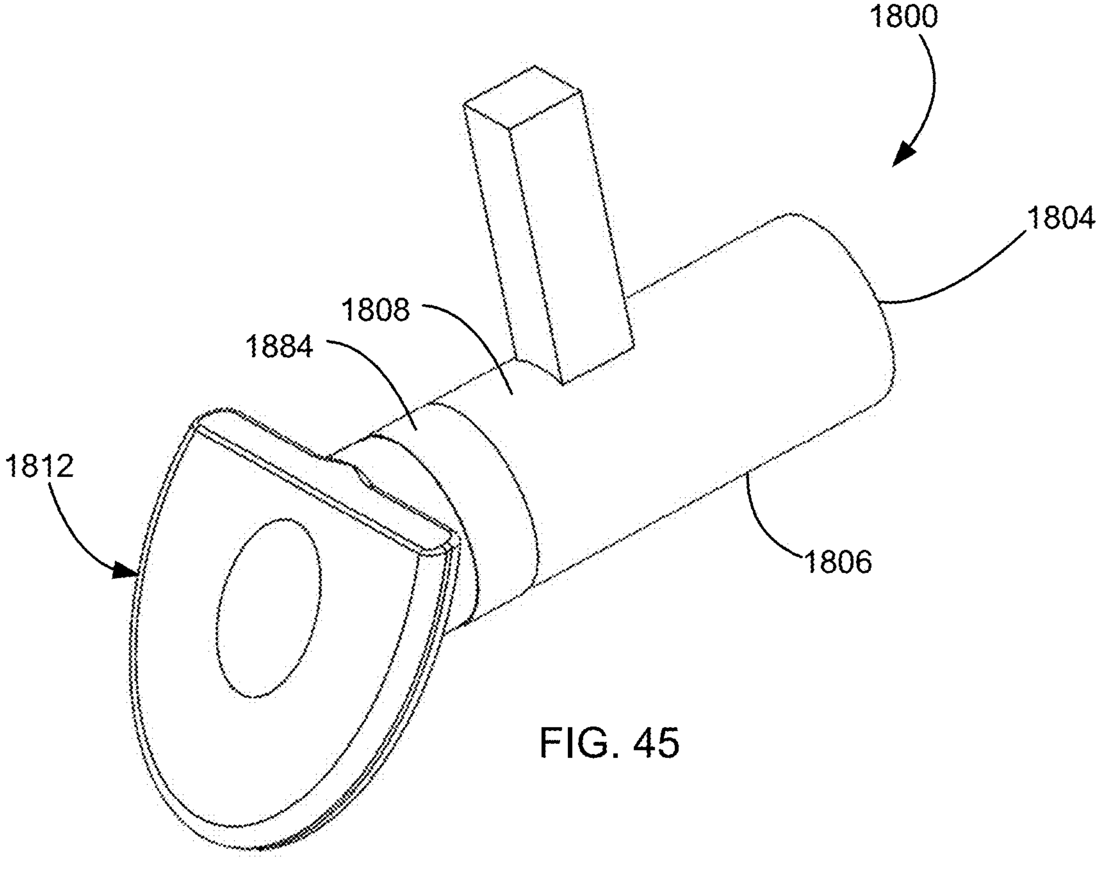
FIG. 45 illustrates a perspective view of a ventilation tube according to yet another embodiment.

FIG. 45 illustrates a perspective view of yet another ventilation tube 1800 that includes texture, color or any other visual feature located on outer facing surface 1808 of hollow body 1806 to distinguish the relative locations along hollow body 1806 to medial flange 1812. In FIG. 45, ventilation tube 1800 includes an area 1884 that covers a circumferential area of hollow body 1806. Area 1884 may be a color band that is different than another color or colors of ventilation tube 1800, it may have a different texture than other textures of ventilation tube 1800 or it could represent a contrast area to show where two colors join or meet. In other words medial flange and medial end comprise a first color and the area between circumferential area 1884 and lateral end 1804 are a different color and circumferential area 1884 includes a third color that is the results of the first color joining or meeting the second color.

Figure 46:
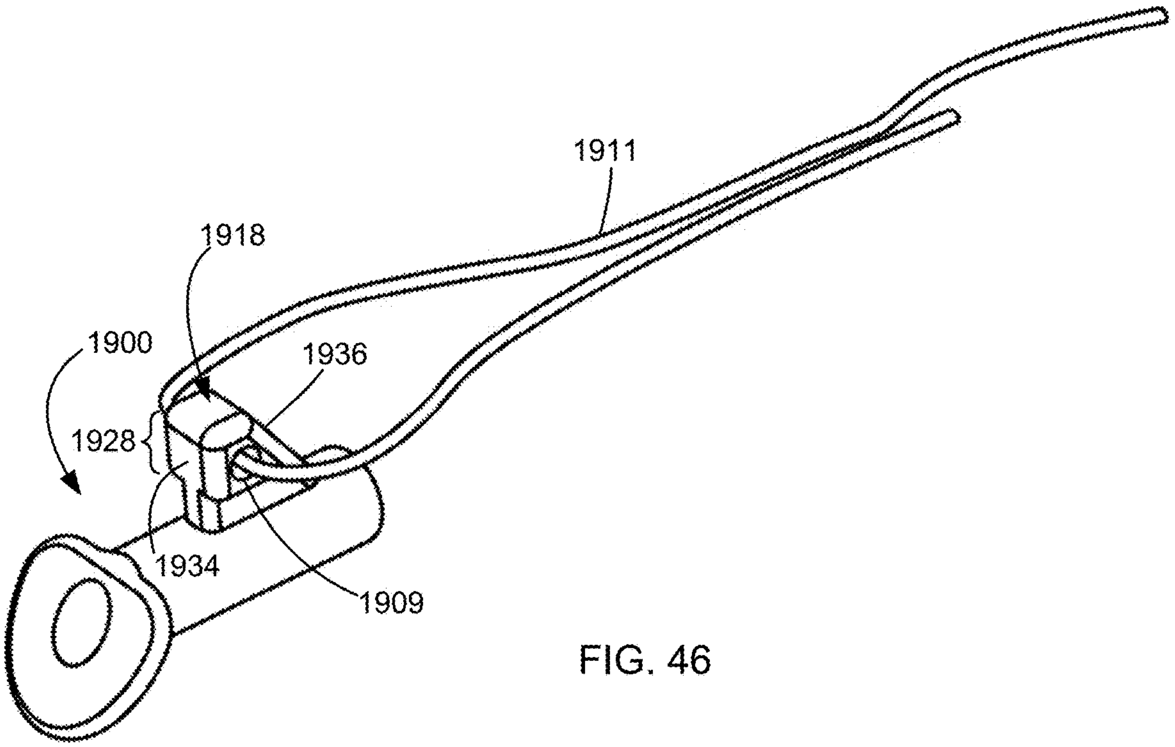
FIG. 46 illustrates a perspective view of a ventilation tube according to yet another embodiment.
Figure 47:
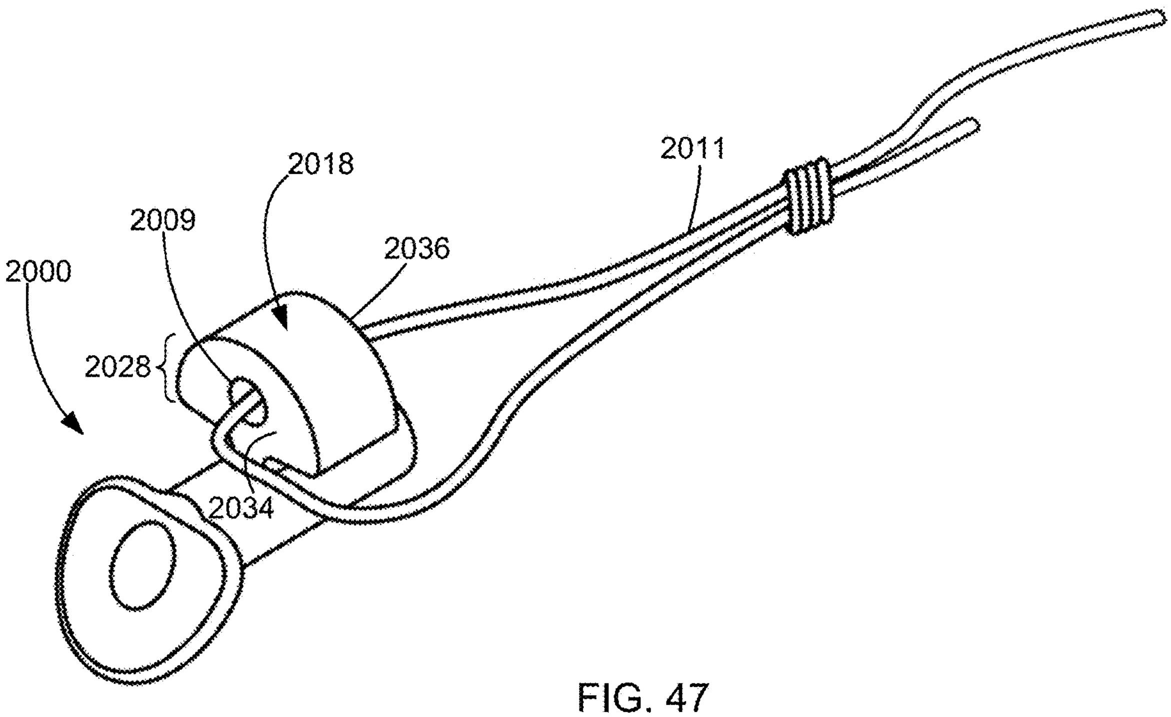
FIG. 47 illustrates a perspective view of a ventilation tube according to yet another embodiment.

FIGS. 46 and 47 illustrate perspective views of ventilation tubes 1900 and 2000 according to more embodiments. Ventilation tubes 1900 and 2000 are similar to ventilation tubes 100 and 800, but each of ventilation tubes 1900 and 2000 further include an aperture 1909 and 2009. Aperture 1909 of ventilation tube 1900 extends from a left-facing side of an upper portion 1928 to a right-facing side of upper portion 1928 of a lateral tab 1918. Aperture 2009 of ventilation tube 2000 extends from a medial-facing side 2034 to a lateral-facing side 2036 of an upper portion 2028 of lateral tab 2018. In FIG. 46, a tether 1911 is provided that interfaces with an element of ventilation tube 1900, such as aperture 1909 in lateral tab 1918. In FIG. 47, a tether 2011 is provided that interfaces with an element of ventilation tube 2000, such as aperture 2009 in lateral tab 2018. In FIGS. 46 and 47, tethers 1911 and 2011 are looped through apertures 1909 and 2009, respectively, and extend laterally such that a user or clinician may grasp both loose ends of tethers 1911 or 2011 and pull tube 1900 or 2000 laterally. For example, if tube 1900 or 2000 is inserted too deeply into the middle ear, the user may grasp and pull tether 1911 or 2011 to correctly position tube 1900 or 2000. In FIG. 46, ends of tether 1911 are free so that the user may grasp one of the free ends and pull it laterally, allowing the other free end to pass through aperture 1909 to easily remove tether 1911. In FIG. 47, tether 201 includes a closed loop, for example, by tying the two ends to form a knot. However, other ways of creating a closed loop are possible including welding and heat bonding such that tether 2011 may be cut to allow the user to remove tether 2011 from tube 2000 after tube 2000 is correctly positioned.

Figure 48:
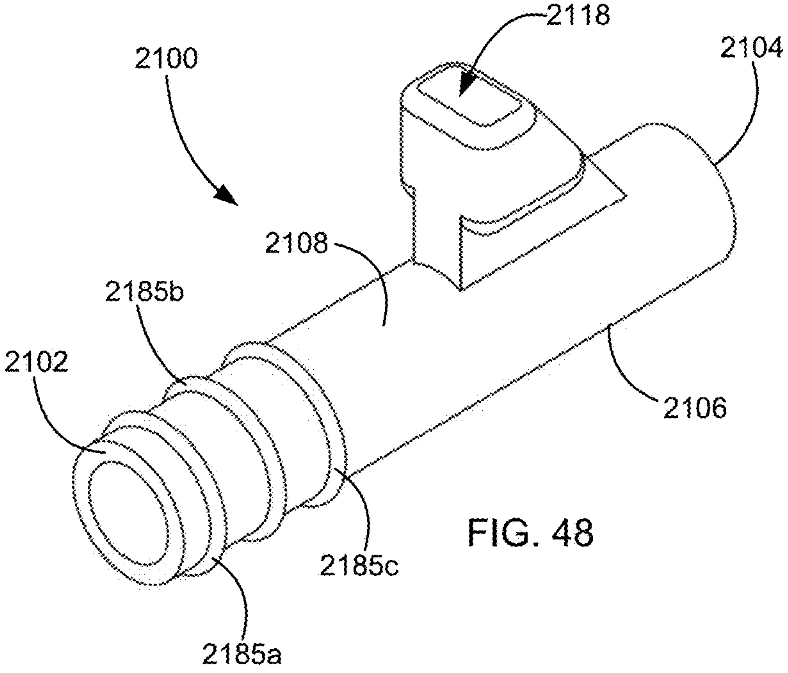
FIGS. 48-50 illustrates perspective, medial end and side views of a ventilation tube according to another embodiment.
Figure 49:
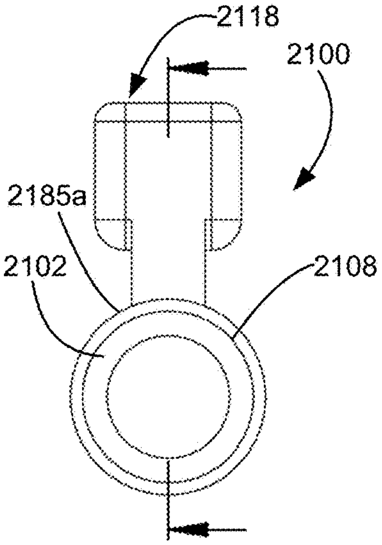
Figure 50:
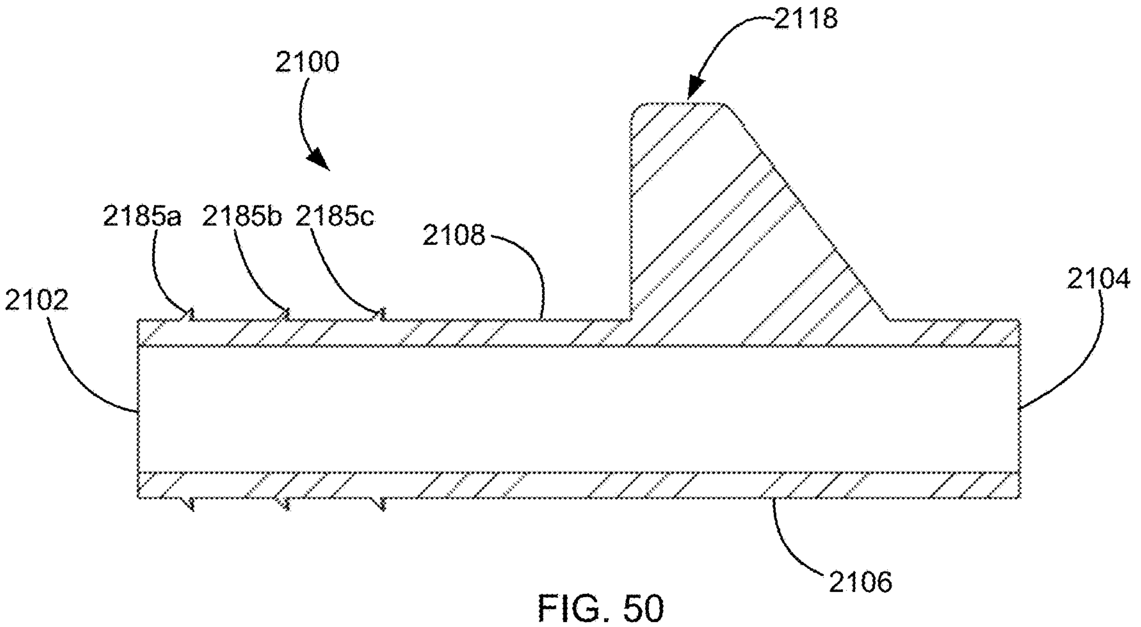

FIG. 48 illustrates a perspective view of a ventilation tube 2100 according to another embodiment. FIG. 49 illustrates a medial end view and FIG. 50 illustrates a section view of ventilation tube 2100. Ventilation tube 2100 includes a hollow body 2106 having a medial end 2102, a lateral end 2104 and a lateral tab 2118 that extends from an outer facing surface 2108 of hollow body 2106. While lateral tab 2118 is similar to lateral tab 118 of ventilation tube 100, ventilation tube 2100 does not include at least one medial flange or at least one lateral flange. In addition, while medial end 2102 is illustrated as being a squared end (e.g. substantially perpendicular to an outer surface of hollow body 2106), in other embodiments medial end 2102 is beveled like medial end 102 of tube 100. Ventilation tube 2100 includes at least one surface feature 2185 located on an outer facing surface of hollow body 2106. In the FIG. 48 embodiment, the at least one surface feature 2185 is located on outer surface of hollow body 2106 between medial end 2102 and lateral tab 2118. As illustrated, ventilation tube 2100 includes at least one continuous rib 2185*a*, 2185*b*, 2185*c* that protrudes from outer facing surface 2108 of hollow body 2106 and extends about a circumference of the outer facing surface of the hollow body. While ventilation tube 2100 illustrates three continuous ribs, it should be recognized that any number of continuous ribs may protrude from outer facing surface 2108 including a single continuous rib. Ribs 2185*a-c* increase friction on outer facing surface 2108 of hollow body 2106 to keep ventilation tube 2100 in place upon insertion into a membrane.

Figure 51:
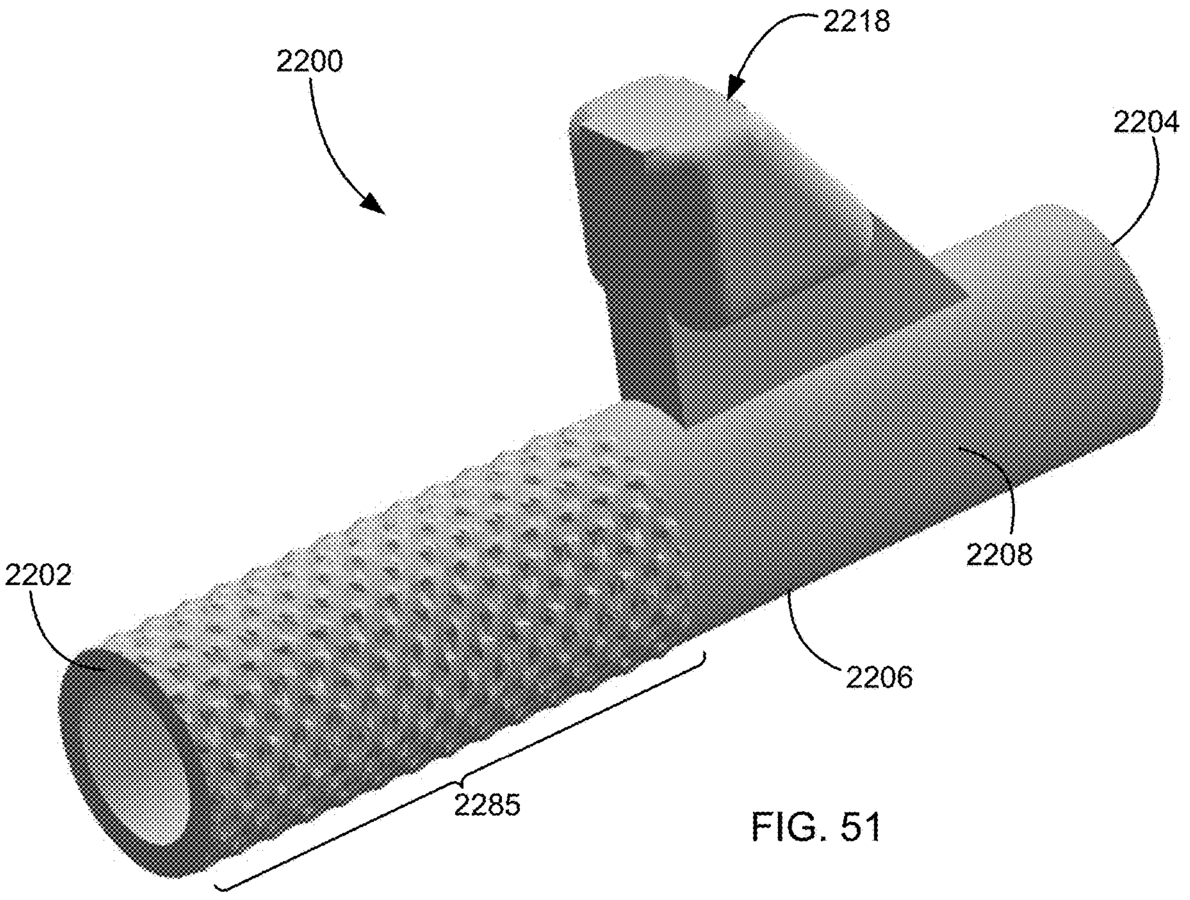
FIG. 51 illustrates a perspective view of a ventilation tube according to another embodiment.

FIG. 51 illustrates a perspective view of a ventilation tube 2200 according to another embodiment. Ventilation tube is similar to ventilation tube 2100 including a hollow body 2206 having a medial end 2202, a lateral end 2204 and a lateral tab 2218 that extends from an outer facing surface 2208 of hollow body 2206. Ventilation tube 2200 includes at least one surface feature 2285 located on an outer facing surface of hollow body 2206. In the FIG. 51 embodiment, the at least one surface feature 2285 is located on an area of outer facing surface 2208 of hollow body 2106 between medial end 2202 and lateral tab 2218. As illustrated, the at least one surface feature 2285 includes surface roughness on a surface area about a circumference of outer facing surface 2208 of hollow body 2206. For example, surface roughness 2285 may extend from medial end 2204 and terminate before lateral tab 2218. However, other surface area locations of surface roughness between medial end 2204 and lateral tab 2218 are possible.

Figure 52:
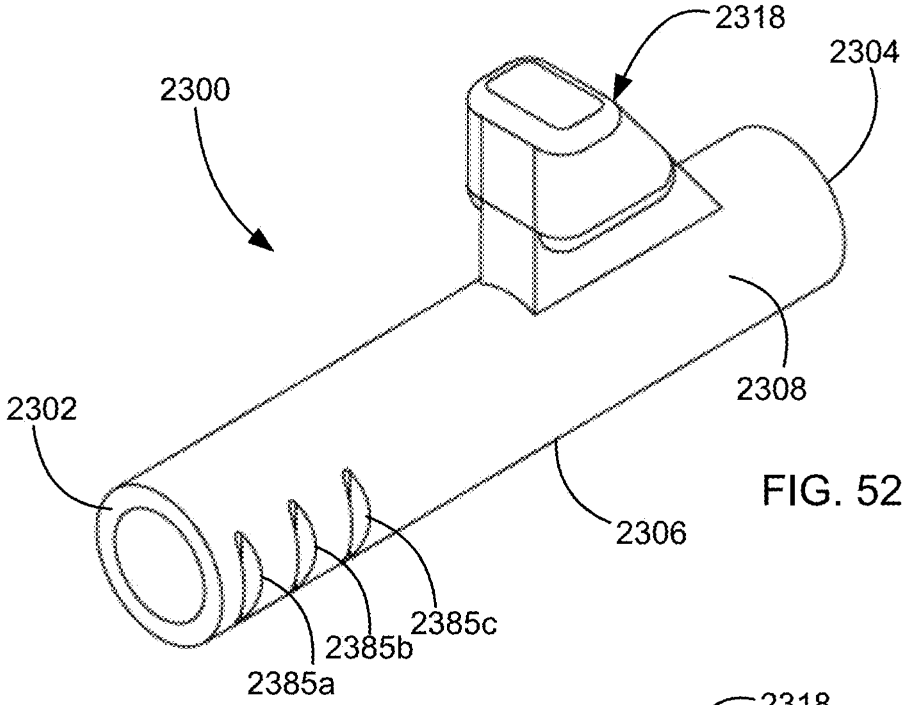
FIGS. 52-54 illustrates perspective, side and top views of a ventilation tube according to another embodiment.
Figure 53:
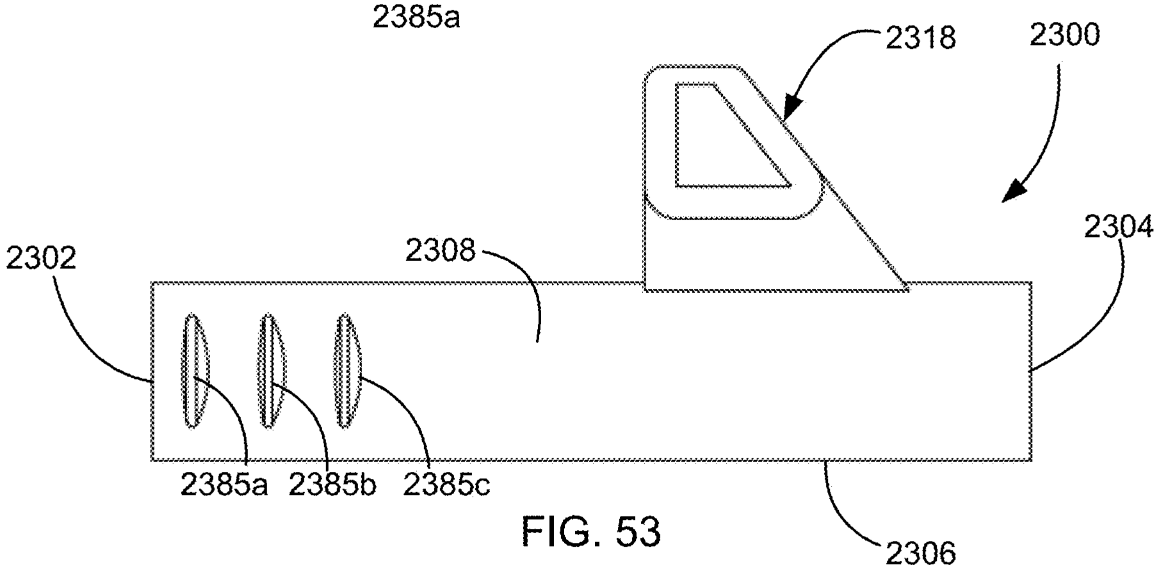
Figure 54:
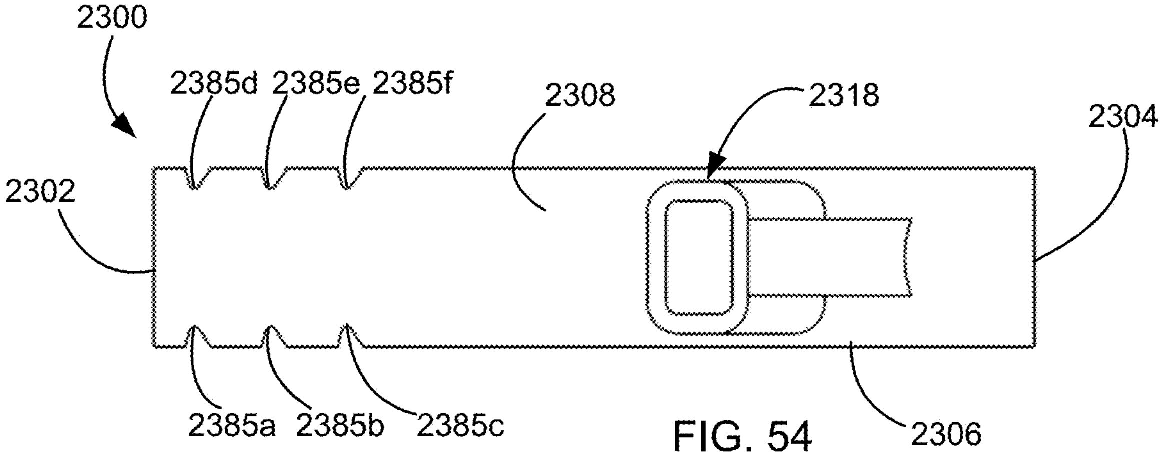

FIG. 52 illustrates a perspective view of a ventilation tube 2300 according to another embodiment. FIG. 53 illustrates a side view and FIG. 54 illustrates a top view of ventilation tube 2300. Ventilation tube 2300 is similar to ventilation tube 2100 including a hollow body 2306 having a medial end 2302, a lateral end 2304 and a lateral tab 2318 that extends from an outer facing surface 2308 of hollow body 2306. Ventilation tube 2300 includes at least one surface feature 2385 located on outer facing surface 2308 of hollow body 2306. In the FIG. 52 embodiment, the at least one surface feature 2385 is located on outer facing surface 2308 of hollow body 2306 between medial end 2302 and lateral tab 2318. As illustrated, ventilation tube 2300 includes at least one groove 2385*a*, 2385*b*, 2385*c*, 2385*d*, 2385*e*, 2385*f* that is recessed from outer facing surface 2308 of hollow body 2306 and extends partially about a circumference of the outer facing surface of the hollow body. While ventilation tube 2300 illustrates six partial grooves where each of three partial grooves oppose each other three, it should be recognized that any number of partial grooves may be recessed from outer facing surface 2308. Grooves 2385*a-f* increase friction on outer facing surface 2308 of hollow body 2306 to keep ventilation tube 2300 in place upon insertion into a membrane.

Figure 55:
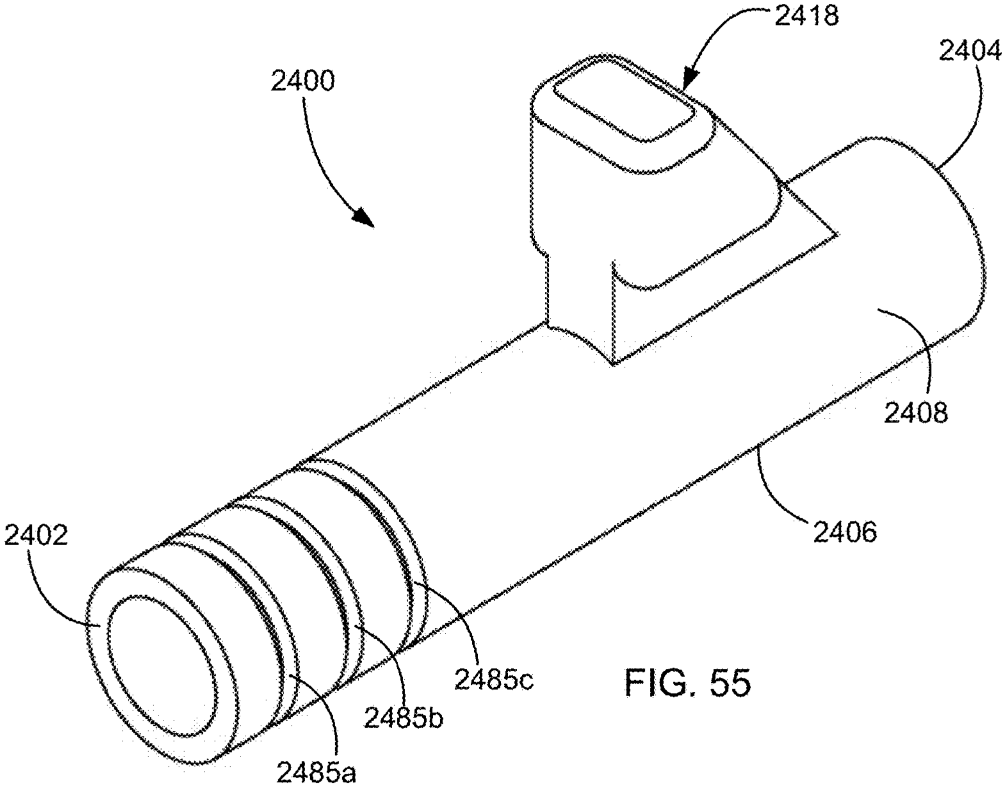
FIGS. 55-56 illustrates perspective and side view of a ventilation tube according to another embodiment.
Figure 56:
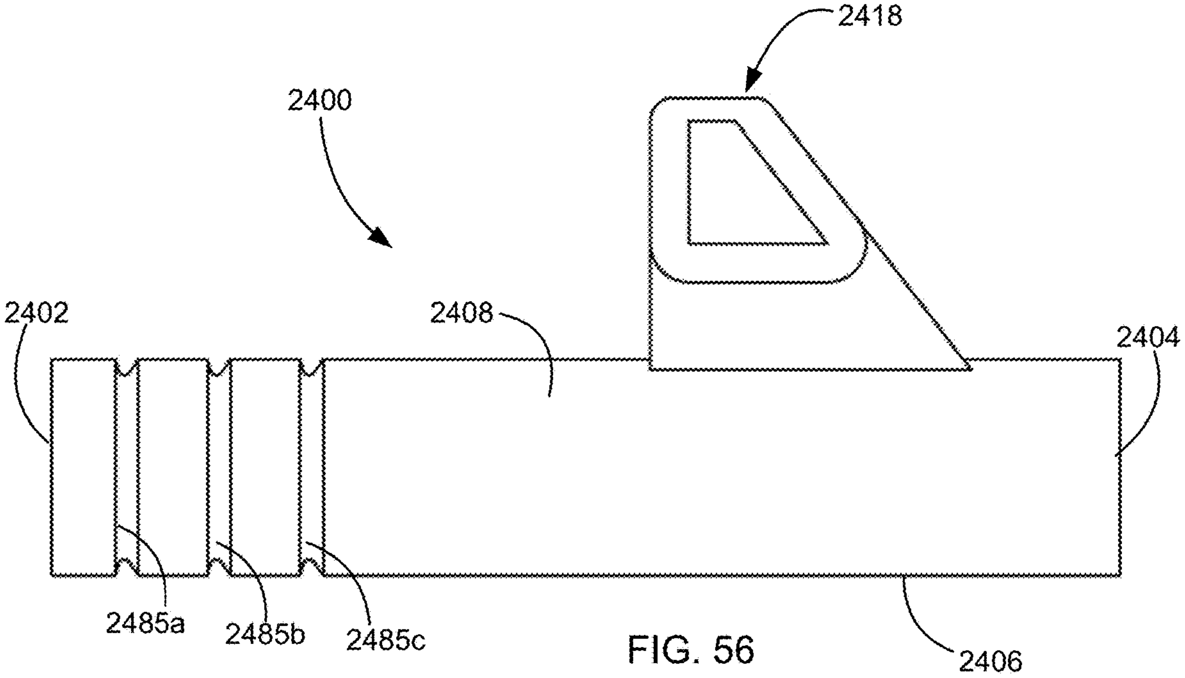

FIG. 55 illustrates a perspective view of a ventilation tube 2400 according to another embodiment. FIG. 56 illustrates a side view of ventilation tube 2400. Ventilation tube 2400 is similar to ventilation tube 2100 including a hollow body 2406 having a medial end 2402, a lateral end 2404 and a lateral tab 2418 that extends from an outer facing surface 2408 of hollow body 2406. Ventilation tube 2400 includes at least one surface feature 2485 located on outer facing surface 2408 of hollow body 2406. In the FIG. 55 embodiment, the at least one surface feature 2485 is located on outer facing surface 2408 of hollow body 2406 between medial end 2402 and lateral tab 2418. As illustrated, ventilation tube 2400 includes at least one continuous groove 2485*a*, 2485*b*, 2485*c* that is recessed from outer facing surface 2408 of hollow body 2406 and extends about a circumference of the outer facing surface of the hollow body. While ventilation tube 2400 illustrates three continuous grooves, it should be recognized that any number of continuous grooves may be recessed from outer facing surface 2408. Grooves 2485*a-f* increase friction on outer facing surface 2408 of hollow body 2406 to keep ventilation tube 2400 in place upon insertion into a membrane.

Although elements have been shown or described as separate embodiments above, portions of each embodiment may be combined with all or part of other embodiments described above. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A ventilation tube comprising:

a hollow body oriented along a central axis and having an inner facing wall, an outer facing wall, a medial end and a lateral end, the hollow body including a length that extends from the medial end to the lateral end; and a lateral tab including a base end, a free end, a medial facing side that faces the medial end of the hollow body and a lateral facing side that faces the lateral end of the hollow body, the lateral tab being coupled to the outer facing wall of the hollow body and extending outwardly from the outer facing wall from the base end to the free end;

wherein the base end of the lateral tab has a first length that extends lengthwise along the hollow body and wherein the free end includes a second length, the first length of the base end of the lateral tab being greater than the second length of the free end of the lateral tab; and wherein the medial facing side of the lateral tab extends from the base end to the free end for a first distance and the lateral facing side of the lateral tab extends from the base end to the free end for a second distance, the first distance being less than the second distance.

2. The ventilation tube of claim 1, wherein the lateral tab further comprises a right side and an opposing left side, wherein the lateral tab forms a solid body defined by the base end, the free end, the medial facing side, the lateral facing side, the right side and the left side.

3. The ventilation tube of claim 2, wherein the lateral facing side is oriented at an angle from the central axis of the hollow body that is greater than 90 degrees and less than 180 degrees.

4. The ventilation tube of claim 1, wherein the lateral tab further comprise a lower portion having the base end and an upper portion having the free end, wherein the upper portion of the lateral tab includes a first width and the lower portion of the lateral tab includes a second width, the first width of the upper portion being greater than the second width of the lower portion and less than a width of the hollow body.

5. The ventilation tube of claim 1, further comprising at least one medial flange located at the medial end of the hollow body.

6. The ventilation tube of claim 5, wherein the ventilation tube comprises an undeployed state and a deployed state, wherein in the undeployed state, the at least one medial flange is configured to be folded in towards the hollow body and the lateral tab is configured to extend outwardly from the outer facing surface of the hollow body, and wherein in the deployed state the at least one medial flange unfolds so that at least portions of the at least one medial flange extend outwardly from the outer facing surface of the hollow body and the lateral tab remains unchanged between the undeployed state and the deployed state.

7. A ventilation tube comprising:

a hollow body oriented along a central axis and having an inner facing wall, an outer facing wall, a medial end and a lateral end, the hollow body including a length that extends from the medial end to the lateral end; and a lateral tab including a base end, a free end, a medial facing side that faces the medial end, a lateral facing side that faces the lateral end, a right side and an opposing left side, the lateral tab being coupled to the outer facing wall of the hollow body and extending outwardly from the outer facing wall to the free end, and wherein the lateral tab includes a lower portion having the base end and an upper portion having the free end, the upper portion of the lateral tab including a first width that extends from the right side to the left side of the lateral tab and the lower portion including a second width that extends from the right side to the left side of the lateral tab, wherein the first width of the upper portion of the lateral tab is greater than the second width of the lower portion of the lateral tab and greater than a width of the hollow body.

8. The ventilation tube of claim 7, wherein the base end of the lateral tab comprises a first length that extends lengthwise along the hollow body and the free end of the lateral tab comprises a second length, the first length of the base end of the lateral tab being greater than the second length of the free end of the lateral tab.

9. The ventilation tube of claim 7, wherein the lateral tab forms a solid body defined by the base end, the free end, the medial facing side, the lateral-facing side, the right side and the left side.

10. The ventilation tube of claim 9, wherein the lateral-facing side is oriented at an angle relative to the central axis of the hollow body that is greater than 90 degrees and less than 180 degrees.

11. The ventilation tube of claim 7, wherein the second width of the lower portion of the lateral tab is less than a width of the hollow body.

12. The ventilation tube of claim 7, wherein the lateral tab comprises a length that extends lengthwise along the hollow body, wherein the length of the lateral tab is greater than the second width of the lateral tab.

13. The ventilation tube of claim 12, wherein the medial-facing side and the lateral facing side being substantially perpendicular to the central axis of the hollow body.

14. The ventilation tube of claim 7, wherein the free end of the lateral tab comprises a curved surface.

15. The ventilation tube of claim 7, further comprising at least one medial flange located at the medial end of the hollow body.

16. The ventilation tube of claim 15, wherein the ventilation tube comprises an undeployed state and a deployed state, wherein in the undeployed state, the at least one medial flange is configured to be folded in towards the hollow body and the lateral tab is configured to extend outwardly from the outer facing surface of the hollow body, and wherein in the deployed state the at least one medial flange unfolds so that at least portions of the at least one medial flange extend outwardly from the outer facing surface of the hollow body and the lateral tab remains unchanged between the undeployed state and the deployed state.

17. A ventilation tube comprising:

a hollow body oriented along a central axis and having an inner facing wall, an outer facing wall, a medial end and a lateral end, the hollow body including a length that extends from the medial end to the lateral end;

at least one medial flange located at the medial end of the hollow main body;

a lateral tab including a base end, a free end, a medial facing side that faces the medial end of the hollow body and a lateral facing side that faces the lateral end of the hollow body, wherein the lateral tab is coupled to the outer facing wall of the hollow body, and extending outwardly from the outer facing wall from the base end to the free end and wherein the lateral facing side of the lateral tab is oriented at an angle relative to the central axis of the hollow body that is greater than 90 degrees and less than 180 degrees; and wherein in an undeployed state the at least one medial flange is folded in towards the hollow body while the lateral tab protrudes outwardly from the outer facing surface of the hollow body and wherein in a deployed state the at least one medial flange unfolds so that at least portions of the medial flange extend outwardly from the outer facing surface of the hollow body and the lateral tab remains unchanged between the undeployed state and the deployed state.

18. The ventilation tube of claim 1, wherein the lateral tab is located between and spaced apart from the medial end and the lateral end.

19. The ventilation tube of claim 7, wherein the lateral tab is located between and spaced apart from the medial end and the lateral end.

20. The ventilation tube of claim 17, wherein the lateral tab is located between and spaced apart from the medial end and the lateral end.

* * * * *